US008541230B2

(12) United States Patent
Barnett et al.

(10) Patent No.: US 8,541,230 B2
(45) Date of Patent: Sep. 24, 2013

(54) POLYNUCLEOTIDES ENCODING ANTIGENIC HIV TYPE C POLYPEPTIDES, POLYPEPTIDES AND USES THEREOF

(75) Inventors: Susan W. Barnett, San Francisco, CA (US); Jan Zur Megede, San Francisco, CA (US)

(73) Assignee: Novartis Vaccines and Diagnostics, Inc, Emeryville, CA (US)

(*) Notice: Subject to any disclaimer, the term of this patent is extended or adjusted under 35 U.S.C. 154(b) by 11 days.

(21) Appl. No.: 13/108,900

(22) Filed: May 16, 2011

(65) Prior Publication Data

US 2011/0236469 A1 Sep. 29, 2011

Related U.S. Application Data

(63) Continuation of application No. 12/215,189, filed on Jun. 25, 2008, now Pat. No. 7,943,375, which is a continuation of application No. 09/475,704, filed on Dec. 30, 1999, now abandoned.

(60) Provisional application No. 60/152,195, filed on Sep. 1, 1999, provisional application No. 60/114,495, filed on Dec. 31, 1998.

(51) Int. Cl.
*A61K 48/00* (2006.01)
*C12N 15/74* (2006.01)
*A01N 63/00* (2006.01)

(52) U.S. Cl.
USPC ... 435/320.1; 536/23.1; 424/93.2; 424/93.21; 424/184.1; 424/185.1; 514/44 R

(58) Field of Classification Search
None
See application file for complete search history.

(56) References Cited

U.S. PATENT DOCUMENTS 4,652,639 A 3/1987 Stabinsky
4,861,707 A 8/1989 Ivanoff et al.
RE33,653 E 7/1991 Mark et al.
5,032,510 A 7/1991 Kovacevic et al.
5,082,767 A 1/1992 Hatfield et al.
5,128,319 A 7/1992 Arlinghaus
5,130,247 A 7/1992 Kniskern et al.
5,156,949 A 10/1992 Luciw et al.
5,174,666 A 12/1992 Martinez et al.
5,256,767 A 10/1993 Salk et al.
5,304,472 A 4/1994 Bass et al.
5,364,773 A 11/1994 Paoletti et al.
5,419,900 A 5/1995 Lane et al.
5,470,720 A 11/1995 Helting et al.
5,503,833 A 4/1996 Redmond et al.
5,550,280 A 8/1996 Dao-Cong et al.
5,622,705 A 4/1997 Morrow
5,637,677 A 6/1997 Greene et al.
5,665,569 A 9/1997 Ohno
5,665,720 A 9/1997 Young et al.
5,670,152 A 9/1997 Weiner et al.
5,683,864 A 11/1997 Houghton et al.
5,686,078 A 11/1997 Becker et al.
5,688,688 A 11/1997 Luciw et al.
5,693,755 A 12/1997 Buonagurio et al.
5,712,088 A 1/1998 Houghton et al.
5,714,596 A 2/1998 Houghton et al.
5,728,520 A 3/1998 Weiner et al.
5,738,852 A 4/1998 Robinson et al.
5,741,492 A 4/1998 Hurwitz et al.
5,750,373 A 5/1998 Garrard et al.
5,766,845 A 6/1998 Weiner et al.
5,786,464 A 7/1998 Seed
5,792,459 A 8/1998 Haigwood
5,795,737 A 8/1998 Seed et al.
5,797,870 A 8/1998 March et al.
5,817,637 A 10/1998 Weiner et al.
5,830,697 A 11/1998 Sikic et al.
5,837,242 A 11/1998 Holliger et al.
5,837,818 A 11/1998 Buonagurio et al.
5,840,313 A 11/1998 Vahlne et al.
5,846,546 A 12/1998 Hurwitz et al.
5,853,736 A 12/1998 Becker et al.
5,858,646 A 1/1999 Kang et al.
5,858,675 A 1/1999 Hillman et al.
5,859,193 A 1/1999 Devare et al.
5,866,320 A 2/1999 Rovinski et al.
5,871,747 A 2/1999 Gengoux-Sedlik et al.
5,876,724 A 3/1999 Girard et al.
5,876,731 A 3/1999 Sia et al.
5,879,907 A 3/1999 Aberg et al.
5,879,925 A 3/1999 Rovinski et al.
5,889,176 A 3/1999 Rovinski et al.
5,932,445 A 8/1999 Lal et al.
5,951,975 A 9/1999 Falo, Jr. et al.

(Continued)

FOREIGN PATENT DOCUMENTS

EP 0187041 7/1986
EP 0199301 10/1986

(Continued)

OTHER PUBLICATIONS

Adams et al. (1987). "The Expression of Hybrid HIV:Ty Virus-like Particles in Yeast," *Nature* 329:68-70.
Anderson (1998). "Human gene protein," *Nature* 392:25-30.
André et al. (Feb. 1998). "Increased Immune Response Elicited by DNA Vaccination with a Synthetic gp120 Sequence with Optimized Codon Usage," *J Virol.* 72(2):1497-1503.
Arthur, et al. (1987). "Serological Responses in Chimpanzees Inoculated with Human Immunodeficiency Virus Glycoprotein (Gp 120) Subunit Vaccine," *Proc Natl Acad Sci USA* 84(23):8583-8587.
*ATCC catalog of cell lines and hybridomas*. 7th edition, (1992) Maryland, pp. 70, 79, 148, 150, 158, 164, 194, 299, 308, and 456.
Attwood (2000). *Science* 290(5491): 471-473.
Azevedo et al. (1999). "Main Features of DNA-Based Immunization Vectors," *Braz J Med Biol Res.* 32(2):147-153.
Baker et al. (1991). "Structures of Bovine and Human Papillomaviruses. Analysis by Cryoelectron Microscopy and Three-dimensional Image Reconstruction," *Biophys. J.* 60:1445-1456.

(Continued)

*Primary Examiner* — Janice Li
(74) *Attorney, Agent, or Firm* — Regina Bautista; Helen Lee

(57) ABSTRACT

The present invention relates to polynucleotides encoding immunogenic HIV type C Gag- and/or Env-containing polypeptides. Uses of the polynucleotides in applications including DNA immunization, generation of packaging cell lines, and production of Gag- and/or Env-containing proteins are also described.

44 Claims, 6 Drawing Sheets

(56) References Cited

U.S. PATENT DOCUMENTS

| | | | |
|---|---|---|---|
| 5,955,342 | A | 9/1999 | Rovinski et al. |
| 5,965,726 | A | 10/1999 | Pavlakis et al. |
| 5,972,596 | A | 10/1999 | Pavlakis et al. |
| 5,990,091 | A | 11/1999 | Tartaglia et al. |
| 6,000,587 | A | 12/1999 | Sackett et al. |
| 6,001,977 | A | 12/1999 | Chang et al. |
| 6,004,763 | A | 12/1999 | Gengoux et al. |
| 6,025,125 | A | 2/2000 | Rovinski et al. |
| 6,060,273 | A | 5/2000 | Dirks et al. |
| 6,060,587 | A | 5/2000 | Weiner et al. |
| 6,063,384 | A | 5/2000 | Morrow et al. |
| 6,074,636 | A | 6/2000 | Nichols |
| 6,080,408 | A | 6/2000 | Rovinski et al. |
| 6,087,486 | A | 7/2000 | Weiner et al. |
| 6,090,388 | A | 7/2000 | Wang |
| 6,093,800 | A | 7/2000 | Reiter et al. |
| 6,096,505 | A | 8/2000 | Selby et al. |
| 6,099,847 | A | 8/2000 | Tobin et al. |
| 6,114,148 | A | 9/2000 | Seed et al. |
| 6,132,973 | A | 10/2000 | Lal et al. |
| 6,139,833 | A | 10/2000 | Burgess et al. |
| 6,139,843 | A | 10/2000 | Rubinstein et al. |
| 6,140,059 | A | 10/2000 | Schawaller et al. |
| 6,146,635 | A | 11/2000 | Cano et al. |
| 6,172,201 | B1 | 1/2001 | Weiner et al. |
| 6,174,666 | B1 | 1/2001 | Pavlakis et al. |
| 6,214,804 | B1 | 4/2001 | Felgner et al. |
| 6,280,989 | B1 | 8/2001 | Kapitonov et al. |
| 6,291,157 | B1 | 9/2001 | Rovinski et al. |
| 6,291,664 | B1 | 9/2001 | Pavlakis et al. |
| 6,316,253 | B1 | 11/2001 | Innis et al. |
| 6,331,404 | B1 | 12/2001 | Berman et al. |
| 6,391,632 | B1 | 5/2002 | Dubensky, Jr. et al. |
| 6,489,542 | B1 | 12/2002 | Corbin et al. |
| 6,541,248 | B1 | 4/2003 | Kingsman et al. |
| 6,602,705 | B1 | 8/2003 | Barnett et al. |
| 6,610,476 | B1 | 8/2003 | Chang et al. |
| 7,211,659 | B2 | 5/2007 | zur Megede et al. |
| 2003/0138453 | A1 | 7/2003 | O'Hagan et al. |

FOREIGN PATENT DOCUMENTS

| | | | |
|---|---|---|---|
| EP | 0242216 | | 10/1987 |
| EP | 0314317 | | 5/1989 |
| EP | 0449116 | A1 | 10/1991 |
| EP | 0617132 | | 9/1994 |
| WO | WO-86/03224 | | 6/1986 |
| WO | WO-87/02775 | | 5/1987 |
| WO | WO-88/00471 | | 1/1988 |
| WO | WO-88/10300 | | 12/1988 |
| WO | WO-89/01940 | | 3/1989 |
| WO | WO-89/02277 | | 3/1989 |
| WO | WO-89/02922 | | 4/1989 |
| WO | WO-89/03222 | | 4/1989 |
| WO | WO-90/00556 | | 1/1990 |
| WO | WO-90/02568 | | 3/1990 |
| WO | WO-90/03984 | | 4/1990 |
| WO | WO-90/10230 | | 9/1990 |
| WO | WO-90/10438 | | 9/1990 |
| WO | WO-90/11092 | | 10/1990 |
| WO | WO-90/11359 | | 10/1990 |
| WO | WO-90/12094 | | 10/1990 |
| WO | WO-90/15141 | | 12/1990 |
| WO | WO-91/04273 | | 4/1991 |
| WO | WO-91/06319 | | 5/1991 |
| WO | WO-91/07425 | | 5/1991 |
| WO | WO-91/07510 | | 5/1991 |
| WO | WO-91/13360 | | 9/1991 |
| WO | WO-91/13906 | | 9/1991 |
| WO | WO-91/15238 | A1 | 10/1991 |
| WO | WO-91/15328 | | 10/1991 |
| WO | WO-91/15512 | | 10/1991 |
| WO | WO-91/16926 | | 11/1991 |
| WO | WO-91/18928 | | 12/1991 |
| WO | WO-91/19803 | | 12/1991 |
| WO | WO-92/03475 | | 3/1992 |
| WO | WO-92/04046 | | 3/1992 |
| WO | WO-92/05799 | | 4/1992 |
| WO | WO-93/02102 | | 2/1993 |
| WO | WO-93/04090 | | 3/1993 |
| WO | WO-93/08836 | | 5/1993 |
| WO | WO-93/14789 | | 8/1993 |
| WO | WO-93/20212 | | 10/1993 |
| WO | WO-93/21346 | | 10/1993 |
| WO | WO-93/23569 | | 11/1993 |
| WO | WO-94/04574 | | 3/1994 |
| WO | WO-94/07922 | | 4/1994 |
| WO | WO-94/11523 | | 5/1994 |
| WO | WO-94/13804 | | 6/1994 |
| WO | WO-94/15621 | | 7/1994 |
| WO | WO-94/16060 | | 7/1994 |
| WO | WO-94/16737 | | 8/1994 |
| WO | WO-94/18221 | | 8/1994 |
| WO | WO-94/20141 | | 9/1994 |
| WO | WO-94/20640 | | 9/1994 |
| WO | WO-94/22477 | | 10/1994 |
| WO | WO-94/26293 | | 11/1994 |
| WO | WO-94/29339 | | 12/1994 |
| WO | WO-95/03407 | | 2/1995 |
| WO | WO-95/04818 | | 2/1995 |
| WO | WO-95/11317 | | 4/1995 |
| WO | WO-95/11701 | | 5/1995 |
| WO | WO-95/24485 | | 9/1995 |
| WO | WO-95/25124 | | 9/1995 |
| WO | WO-95/27505 | | 10/1995 |
| WO | WO-95/29700 | | 11/1995 |
| WO | WO-95/33206 | | 12/1995 |
| WO | WO-95/33835 | | 12/1995 |
| WO | WO-96/02273 | | 2/1996 |
| WO | WO-96/02557 | | 2/1996 |
| WO | WO-96/04382 | | 2/1996 |
| WO | WO-96/09066 | | 3/1996 |
| WO | WO-96/09318 | | 3/1996 |
| WO | WO-96/09378 | | 3/1996 |
| WO | WO-96/16178 | | 5/1996 |
| WO | WO-96/20732 | | 7/1996 |
| WO | WO-96/23509 | | 8/1996 |
| WO | WO-96/25177 | | 8/1996 |
| WO | WO-96/30523 | | 10/1996 |
| WO | WO-96/40290 | | 12/1996 |
| WO | WO-97/03198 | | 1/1997 |
| WO | WO-97/11605 | | 4/1997 |
| WO | WO-97/26009 | | 7/1997 |
| WO | WO-97/31115 | | 8/1997 |
| WO | WO-97/48370 | | 12/1997 |
| WO | WO-98/08539 | | 3/1998 |
| WO | WO-98/12207 | | 3/1998 |
| WO | WO-98/26075 | | 6/1998 |
| WO | WO-98/34640 | | 8/1998 |
| WO | WO-98/41536 | | 9/1998 |
| WO | WO-98/41645 | | 9/1998 |
| WO | WO-98/43182 | | 10/1998 |
| WO | WO-98/48843 | | 11/1998 |
| WO | WO-98/59074 | | 12/1998 |
| WO | WO-99/02694 | | 1/1999 |
| WO | WO-99/06599 | | 2/1999 |
| WO | WO-99/09412 | | 2/1999 |
| WO | WO-99/12416 | | 3/1999 |
| WO | WO-99/13864 | | 3/1999 |
| WO | WO-99/16883 | | 4/1999 |
| WO | WO-99/33346 | | 7/1999 |
| WO | WO-99/41397 | | 8/1999 |
| WO | WO-99/41398 | | 8/1999 |
| WO | WO-99/52463 | | 10/1999 |
| WO | WO-99/53960 | | 10/1999 |
| WO | WO-99/67395 | | 12/1999 |
| WO | WO-00/08043 | | 2/2000 |
| WO | WO-00/15819 | | 3/2000 |
| WO | WO-00/18929 | | 4/2000 |
| WO | WO-00/21556 | | 4/2000 |
| WO | WO-00/29561 | | 5/2000 |
| WO | WO-00/39302 | | 7/2000 |
| WO | WO-00/39303 | | 7/2000 |
| WO | WO-00/39304 | | 7/2000 |
| WO | WO-00/44926 | | 8/2000 |

| | | |
|---|---|---|
| WO | WO-00/65076 | 11/2000 |
| WO | WO-00/66179 | 11/2000 |
| WO | WO-00/67761 | 11/2000 |
| WO | WO-00/67787 | 11/2000 |
| WO | WO-00/71561 | 11/2000 |
| WO | WO-01/02607 | 1/2001 |
| WO | WO-01/12223 | 2/2001 |
| WO | WO-01/16342 | 3/2001 |
| WO | WO-01/19958 | 3/2001 |
| WO | WO-01/21270 | 3/2001 |
| WO | WO-01/26681 | 4/2001 |
| WO | WO-01/29225 | 4/2001 |
| WO | WO-01/36614 | 5/2001 |
| WO | WO-01/42308 | 6/2001 |
| WO | WO-01/43693 | 6/2001 |
| WO | WO-01/45748 | 6/2001 |
| WO | WO-01/46408 | 6/2001 |
| WO | WO-01/47955 | 7/2001 |
| WO | WO-01/54701 | 8/2001 |
| WO | WO-01/54719 | 8/2001 |
| WO | WO-01/60393 | 8/2001 |
| WO | WO-01/60838 | 8/2001 |
| WO | WO-03/004620 | 1/2003 |
| WO | WO-03/020876 | 3/2003 |

OTHER PUBLICATIONS

Baker et al. (2001). *Science*, 294:93-96.
Barnett et al. (1999). "DNA vaccines coming of age," *Annual Rep. Med Chem*, pp. 149-158.
Barnett et al. (Jun. 2001). "The ability of an oligomeric human immunodeficiency virus type 1 (HIV-1) envelope antigen to elicit neutralizing antibodies against primary HIV-1 isolates is improved following partial deletion of the second hypervariable region," *J Virol.* 75(12):5526-40.
Barr, et al. (1987). "Antigenicity and Immunogenicity of Domains of the Human Immunodeficiency Virus (HIV) Envelope Polypeptide Expressed in the Yeast *Saccharomyces cerevisiae," Vaccine* 2(2):90-101.
Barre-Sinoussi et al. (1983). "Isolation of a T-Lymphotropic Retrovirus from a Patient at Risk for Acquired Immune Deficiency Syndrome (AIDS)," *Science* 220:868-871.
Barrett, et al. (1989). "Large-scale production and purification of a vaccinia recombinant-derived HIV-1 gp160 and analysis of its immunogenicity," *AIDS Res Hum Retroviruses* 5(21):159-71.
Beard, W. A. et al. (1996). "Role of the "Helix Clamp" in HIV-I Reverse Transcriptase Catalytic Cycling as Revealed by Alanine-Scanning Mutagenesis," *Journal Of Biological Chemistry* 271(21):12213-12220.
Berger, P.B. (1995). "New Directions in Research: Report from the 10th International Conference on AIDS," *Canadian Medical Association Journal* 152(12):1991-1995.
Berman, et al. (1988). "Human Immunodeficiency Virus Type 1 Challenge of Chimpanzees Immunized with Recombinant Envelope Glycoprotein gp 120," *Proc Natl Acad Sci USA* 85(14):5200-5204.
Berman, et al. (1989). "Expression and Immunogenicity of the Extracellular Domain of the Human Immunodeficiency Virus Type 1 Envelope Glycoprotein, gp 160," *J Virol.* 63(8):3489-3498.
Birx and Redfield, (1991). "HIV Vaccine Therapy," *Int J Immunopharmacol.* 13(1):129-132.
Bolognesi et al. (1994). "NIH conference, HIV vaccine development: a progress report," *Ann. Int. Med.* 8(7):603-611.
Bolognesi, D.P. (1989). "Progress in Vaccines Against AIDS," *Science* 246:1233-1234.
Borrow, et al. (1994). "Virus-Specific CD8 + Cytotoxic T-Lymphocyte Activity Associated with Control of Viremia in Primary Human Immunodeficiency Virus Type 1 Infection," *J Virol.* 68(9):6103-6110.
Borsetti et al., (1998). "The C-terminal half of the human immunodeficiency virus type 1 Gag precursor is sufficient for efficient particle assembly." *Virol.* 72(11):9313-9317.
Bourgault, et al. (1993). "Cytotoxic T-Cell Response and AIDS-Free Survival in Simian Immunodeficiency Virus-Infected Macaques," *AIDS* 7(Suppl 2):S73-S79.
Brown et al. (1994). "Chimeric Parvovirus B19 Capsids for the Presentation of Foreign Epitopes," *Virology* 198:477-488.
Brusic et al. (1998). "Prediction of MHC class II-binding peptides using an evolutionary algorithm and artificial neural network," *Bioinformatics* 14(2):121-30.
Bujacz, G., et al. (1996). "The Catalytic Domain of Human Immunodeficiency Virus Integrase: Ordered Active Site in the F185H Mutant," *FEBS Letters* 398(2-3):175-178.
Burton et al. (1997). "The antibody response in HIV-1 infection" *AIDS* 11(Suppl. A):S87-S98.
Burton et al., (1998). "Why do we not have an HIV vaccine and how can we make one," *Nature Medicine* 4(5):495-497.
Cao et al. (1997) "Replication and neutralization of human immunodeficiency virus type 1 lacking the V1 and V2 variable loops of the gp120 envelope glycoprotein" *J. Virol.* 71(12):9808-9812.
Carmichael et al. (1993). "Quantitative Analysis of the Human Immunodeficiency Virus Type 1 (HIV-1)-specific Cytotoxic T Lymphocyte (CTL) Response at Different Stages of HIV-1 Infection: Differential CTL Responses to HIV-1 and Epstein-barr Virus in Late Disease," *J Exp Med.* 177(2):249-256.
Carter, (1994) "Epitope Mapping of a Protein Using the Geysen (PEPSCAN) Procedure," *Methods Mol. Biol.* 36:207-23.
Chang et al. (Aug. 2000). "Human immunodeficiency virus type 1 subtype E envelope recombinant peptides containing naturally immunogenic epitopes," *J Infect Dis.* 182(2):442-50.
Chazal N. et al. (1994). "Phenotypic Characterization of Insertion Mutants of the Human Immunodeficiency Virus Type 1 Gag Precursor Expressed in Recombinant Baculovirus-infected Cells," *Virology* 68(1): 111-122.
Cheng-Mayer, (1989) "Isolates of human immunodeficiency virus type 1 from the brain may constitute a special group of the AIDS virus," *PNAS USA* 86:8575-8579.
Chu, P et al. (1998). "Retrovirus-mediated gene transfer into human hematopoietic stem cells," *J Mol Med* 76:184-192.
Ciernik et al. (1996). "Induction of Cytotoxic T Lymphocytes and Antitumor Immunity with DNA Vaccines Expressing Single T Cell Epitopes," *J Immunol.* 156(7):2369-2375.
Clavel et al. (1986). "Isolation of a New Human Retrovirus from West African Patients with AIDS," *Science* 233:343-346.
Clavel et al. (1986). "Molecular Cloning and Polymorphism of the Human Immune Deficiency Virus Type 2," *Nature* 324:691-695.
Daar et al. (1991). "Transient High Levels of Viremia in Patients with Primary Human Immunodeficiency Virus Type 1 Infection," *N Engl J Med.* 324(14):961-964.
Dai, L. C., et al. (1992) "Mutation of human immunodeficiency virus type 1 at amino acid 585 on gp41 results in loss of killing by CD8+ A24-restricted cytotoxic T lymphocytes," *J. Virol.* 66(5):3151-3154.
Davenport et al. (1995) "An empirical method for the prediction of T-cell epitopes," *Immunogenetics* 42:392-97.
Davey et al. (1997). "Subcutaneous administration of interleukin-2 in human immunodeficiency virus type 1-infected persons," *J Infect Dis.* 175(4):781-789.
Davies J. F., et al. (1991). "Crystal structure of the ribonuclease H Domain of HIV-1 reverse transcriptase," *Science* 252(5002):86-95.
Deminie et al. (1996). "Evaluation of Reverse Transcriptase and Protease Inhibitors in Two-drug Combinations Against Human Immunodeficiency Virus Replication," *Antimicrob Agents Chemother.* 40(6):1346-1351.
Desai et al. (1986). "Molecular Cloning and Primary Nucleotide Sequence Analysis of a Distinct Human Immunodeficiency Virus Isolate Reveal Significant Divergence in its Genomic Sequence," *Proc. Natl. Acad. Sci. USA* 63:8360-8384.
Desrosiers, R. C., (2004). "Prospects for an AIDS vaccine," *Nat. Med.* 10(3):221-223.
Doe et al. (1994). "Induction of HIV-1 Envelope (gp 120)-Specific Cytotoxic T Lymphocyte Responses in Mice by Recombinant CHO Cell-Derived gp 120 is Enhanced by Enzymatic Removal of N-Linked Glycans," *Eur. J. Immunol.* 24:2369-2376.
Doe, B. and Walker, C.M. (1996). "HIV-1 p24 Gag-Specific Cytotoxic T-Lymphocyte Responses in Mice," *AIDS* 10(7):793-794.
D'Souza et al., (1997). "Evaluation of monoclonal antibodies to human immunodeficiency virus type 1 primary isolates by neutralization assays: performance criteria for selecting candidate antibodies for clinical trials, AIDS Clinical Trials Group Antibody Selection Working Group." *J. Infect. Dis.* 175:1056-1062.

Dyda F., et al. (1994). "Crystal Structure of the Catalytic Domain of HIV-1 Integrase: Similarity to Other Polynucleotidyl Transferases," *Science* 266(5193):1981-1986.
Earl et al. (1989). "Isolate-and Group-specific Immune Responses to the Envelope Protein of Human Immunodeficiency Virus Induced by a Live Recombinant Vaccinia Virus in Macaques," *AIDS Res Hum Retroviruses* 5(1):23-32.
Earl et al., (1990). "Oligomeric structure of the human immunodeficiency virus type 1 envelope glycoprotein" *PNAS USA* 87:648-652.
Earl et al., (1991). "Biological and immunological properties of human immunodeficiency virus type 1 envelope glycoprotein: analysis of proteins with truncations and deletions expressed by recombinant vaccinia viruses" *J. Virol* 65:31-41.
Edelman, R. (1980). "Vaccine Adjuvants." *Rev Infect Dis.* 2(3):370-383.
Engelman, A. et al. (1997). "Structure-based Mutagenesis of the Catalytic Domain of Human Immunodeficiency Virus Type 1 Integrase," *Journal of Virology* 21(5):3507-3514.
Esnouf et al. (1995). "Mechanism of Inhibition of HIV-1 Reverse Transcriptase by Nonnucleoside Inhibitors," *Structural Biology* 2(4):303-306.
Evans et al., (1989). "An Engineered Poliovirus Chimaera Elicits Broadly Reactive Hiv-1 Neutralizing Antibodies," *Nature* 339(6223):385-388.
Faust et al., (1996). "Outpatient Biopsies of the Palatine Tonsil: Access to Lymphoid Tissue for Assessment of Human Immunodeficiency Virus RNA Titers," *Otolaryngol Head Neck Surg.* 114(4):593-598.
Feller & De La Cruz, (1991). "Identifying antigenic T-cell sites," *Nature* 349(6311):720-721.
Fennie et al., (1989). "Model for Intracellular Folding of the Human Immunodeficiency Virus Type 1 gp120," *J Virol.* 63(2):639-646.
Fenoglio, D., et al., (2000). "Natural analogue peptides of HIV-1 gp120 T-helper epitope antagonize response of gp120-specific human CD4 T-cell clones," *J AIDS* 23:1-7.
Ferre et al., (1996). "Combination Therapies Against HIV-1 Infection: Exploring the Concept of Combining Antiretroviral Drug Treatments with HIV-1 Immune-Based Therapies in Asymptomatic Individuals," *AIDS Patient Care STDS* 10(6):357-361.
Fiore et al. (1994). "The biological phenotype of HIV-1 is usually retained during and after sexual transmission" *Virol.* 204:297-303.
Fisher, et al. (1988). "Biologically diverse molecular variants within a single HIV-1 isolate," *Nature* 334:444-447.
Fox et al., (1994). "No Winners Against AIDS," *Bio/Technology* 11(2):128.
Freed, E.O., (1998). "HIV-1 gag proteins: diverse functions in the virus life cycle" *Virology* 251:1-15.
Gamier, L. et al., (1998). "Particle Size Determinants in the Human Immunodeficiency Virus Type 1 Gag Protein," *J Virol*72(6):4667-4677.
Genbank Accession No. AF11 0965 [online]. [Retrieved on Aug. 6, 2008]. Retrieved from the Internet: <http://www.ncbi.nlm.nih.gov/entrez/viewer.fcgi?db=nuccore&id=4324721>.
Genbank Accession No. AF11 0967 [online]. [Retrieved on Aug. 6, 2008]. Retrieved from the Internet: <http://www.ncbi.nlm.nih.gov/entrez/viewer.fcgi?db=nuccore&id=4324723>.
GenBank accession No. AF110968 [online]. [Retrieved on Aug. 6, 2008]. Retrieved from the Internet: <http://www.ncbi.nlm.nih.gov/nuccore/4324724>.
GenBank accession No. AF110975 [online]. [Retrieved on Aug. 6, 2008]. Retrieved from the Internet: <http://www.ncbi.nlm.nih.gov/nuccore/4324731>.
GenBank accession No. M65024 [online]. [Retrieved on Aug. 6, 2008]. Retrieved from the Internet: <http://www.ncbi.nlm.nih.gov/nuccore/328672>.
Gerhold et al. (1996). *BioEssays*, 18(12):973-981.
Geysen et al. (1984). "Use of peptide synthesis to probe viral antigens for epitopes to a resolution of a single amino acid," *Proc. Natl. Acad. Sci. USA* 81:3998-4002.
Goldgur, Y. et al., (1998) "Three New Structures of the Core Domain of HIV-1 Integrase: an Active Site That Binds Magnesium," *Proc. Natl. Acad. Sci. USA* 95(16):9150-9154.
Goudsmit et al., (1988) "Human Immunodeficiency Virus Type 1 Neutralization Epitope with Conserved Architecture Elicits Early Type-specific Antibodies in Experimentally Infected Chimpanzees," *Proc. Nat Acad. Sci. USA* 85:4478-4482.
Greene (1993). "AIDS and the Immune System," *Scientific American* Sep.:99-105.
Griffiths J.C. et al. (1993). "Hybrid Human Immunodeficiency Virus Gag Particles as an Antigen Carrier System: Induction of Cytotoxic T-cell and Humoral Responses by a Gag:V3 Fusion," *J. Virol.* 67(6):3191-3198.
Grimison B. and Laurence, J., (1995). "Immunodominant Epitope Regions of HIV-1 Reverse Transcriptase: Correlations with HIV-1 + Serum IgG Inhibitory to Polymerase Activity and With Disease Progression," *J AIDS and Human Retrovirology* 9(1):58-68.
Gurgo et al., (1988). "Envelope Sequences of Two New United States HIV-1 Isolates," *Virology* 164:531-536.
Gurunathan et al. (1998). "CD40 Ligand/Trimer DNA Enhances Both Humoral and Cellular Immune Responses and Induces Protective Immunity to Infectious and Tumor Challenge," *J Immunol.* 161(9):4563-4571.
Guyander et al., (1987) "Genome Organization and Transactivation of the Human Immunodeficiency Virus Type 2," *Nature* 326:662-669.
Haas et al. (1998). "Cytotoxic T-cell responses to HIV-1 reverse transcriptase, integrase and protease," *AIDS* 12:1427-1436.
Haas et al., (1996). "Codon usage limitation in the expression of HIV-1 envelope glycoprotein," *Current Biology* 6(3):315-324.
Hagensee et al., (1994). "Three-dimensional Structure of Vaccinia Virus-produced Human Papillomavirus Type 1 Capsids," *J. Virol.* 68:4503-4505.
Hahn et al., (1986). "Genetic Variation in HTLV-III/LAV Over Time in Patients with AIDS or at Risk for AIDS," *Science* 232:1548-1553.
Halene, S et al. (Jun. 2000). "Gene Therapy using Hematopoietic Stem Cells: Sisyphus Approaches the Crest," *Human gene therapy* 11:1259-1267.
Hamajima, et al. (1996). "The combination of DNA and peptide vaccines induces strong immunities against HIV-1 in both humoral and CMI," *11th Interactional AIDS Conference*, Vancouver, British Columbia, Jul. 7-12; 11:6 (abstract No. Mo.A.151).
Hammer et al. (1994) "Issues in Combination Antiretroviral Therapy: a Review," *J AIDS* 7(Suppl 2):S24-S37.
Haynes et al. (1996). "Update on the Issues of HIV Vaccine Development," *Ann Med.* 28(1):39-41.
Haynes et al., (1996). "Toward an Understanding of the Correlates of Protective Immunity to HIV Infection" *Science* 271:324-328.
Heeney et al., (1998). "Beta-chemokines and Neutralizing Antibody Titers Correlate with Sterilizing Immunity Generated in HIV-I Vaccinated Macaques," *Proc Natl Acad Sci USA* 95(18):10803-10808.
Heeney et al., (1999). "HIV-1 vaccine-induced immune responses which correlate with protection from SHIV infection: compiled preclinical efficacy data from trials with ten different HIV-1 vaccine candidates," *Immunology Letters* 66:189-195.
Hickman, A. B., et al., (1994). "Biophysical and enzymatic properties of the catalytic Domain of HIV-I integrase," *Journal of Biological Chemistry* 269(46):29279-29287.
Ho et al., (1987). "Human Immunodeficiency Virus Neutralizing Antibodies Recognize Several Conserved Domains on the Envelope Glycoproteins," *J Virol.* 61(6):2024-2028.
Hopp, (1993). "Retrospective: 12 Years of Antigenic Determinant Predictions and More," *Peptide Research* 6:183-90.
Hu et al., (1992). "Protection of macaques against SIV infection by subunit vaccines of SIV envelope glycoprotein gp160," *Science* 255:456-459.
Instructions to Authors, 2008, *J. Virol.* 82(1):1-19.
Jacobo-Molina, A. et al., (1993). "Crystal Structure of Human Immunodeficiency Virus Type 1 Reverse Transcriptase Complexed with Double-stranded DNA at 3.0 A Resolution Shows Bent DNA," *Proc Natl Acad Sci USA* 90(13):6320-6324.
Jameson et al., (1988). "The antigenic index: a novel algorithm for predicting antigenic determinants," *CABIOS* 4(1):1818-1886.
Javaherian et al., (1989). "Principal neutralizing domain of the human immunodeficiency virus type 1 envelope protein" *PNAS* 86:6786-6772.

Jeffs et al., (1996). "Antigenicity of truncated forms of the human immunodeficiency virus type 1 envelope glycoprotein" *J. of Gen. Virol.* 77:1403-1410.
Johnson et al. (1991). *The Journal of Immunology*, 147:1512-13 and 1515-1521.
Johnson, P. R. et al., (1992). "Identification of overlapping HLA class I-restricted cytotoxic T cell epitopes in a conserved region of the human immunodeficiency virus type 1 envelope glycoprotein: definition of minimum epitopes and analysis of the effects of sequence variation," *J. Exp. Med.* 175:961-971.
Kafri et al. (1997). *Nat. Genet.* 1997, 17:abstract.
Kang et al., (1991). "Evidence for non-V3-specific neutralizing antibodies that interfere with gp120/CD4 binding in human immunodeficiency virus 1-infected humans" *PNAS USA* 88:6171-6175.
Katz, R. A. and Skalka, A. M., (1994). "The Retroviral Enzymes," *Annual Review of Biochemistry* 63:133-173.
Keefer, et al., (1996). "Safety and Immunogenicity of Env 2-3, a Human Immunodeficiency Virus Type 1 Candidate Vaccine, in Combination with a Novel Adjuvant, MTP-PE/MF59. NIALD AIDS Vaccine Evaluation Group," *AIDS Res Hum Retroviruses.* 12(8):683-693.
Kent, et al. (2000). "A recombinant avipoxvirus HIV-1 vaccine expressing interferon-gamma is safe and immunogenic in macaques," *Vaccine* 18:2250-2256.
Kirnbauer et al., (1993). "Efficient Self-assembly of Human Papillomavirus Type 16 L 1 and L1-L2 into Virus-Like Particles," *J. Virol.* 67:6929-6936.
Klenerman et al. (1998). "Original Antigenic Sin Impairs Cytotoxic T Lymphocyte Responses to Viruses Bearing Variant Epitopes," *Nature* 394(6692):482-485.
Koff and Schultz, (1996). "Progress and Challenges Toward and AIDS Vaccine: Brother, Can You Spare a Paradigm?" *J. Clinical Immunology* 16(3):127-133.
Koff et al., (1988). "Development and Testing of AIDS Vaccines," *Science* 241:426-432.
Kohl et al., (1988). "Active Human Immunodeficiency Virus Protease Is Required for Viral Infectivity," *PNAS USA* 85:4686-4690.
Kohlstaedt, L. A. et al., (1992). "Crystal Structure at 3.5 A Resolution of HIV-I Reverse Transcriptase Complexed with an Inhibitor," *Science* 256(5065):1783-1790.
Kolaskar et al. (1990). "A semi-empirical method for prediction of antigenic determinants on protein antigens." *FEBS Lett.* 276:172-174.
Koup et al., (1994). "Temporal Association of Cellular Immune Responses with the Initial Control of Viremia in Primary Human Immunodeficiency Virus Type 1 Syndrome," *J Virol.* 68(7):4650-4655.
Kovacs et al., (1995). "Increases in CD4 T Lymphocytes with Intermittent Courses of Interleukin-2 in Patients with Human Immunodeficiency Virus Infection," *New England J. Med.* 332(9):567-575.
Kovacs et al., (1996). "Controlled Trial of Interleukin-2 Infusions in Patients Infected with the Human Immunodeficiency Virus," *N Engl J Med.* 335(18):1350-1356.
Krausslich et al., (1988). "Processing of in Vitro-synthesized Gag Precursor Proteins of Human Immunodeficiency Virus (HIV) Type 1 by HIV Proteinase Generated in *Escherichia coli," J. Virol.* 62:4393-4397.
Kreuter J., et al., (1978). "Mode of Action of Immunological Adjuvants: Some Physicochemical Factors Influencing the Effectivity of Polyacrylic Adjuvants," *Infect Immun.* 19(2):667-675.
Krug, M. S. and Berger, S. L., (1991). "Reverse Transcriptase from Human Immunodeficiency Virus: a Single Template-primer Binding Site Serves Two Physically Separable Catalytic Functions," *Biochemistry* 30(44):10614-10623.
Kuby, J, (1994). "Vaccines," in *Immunology*, 2nd Edition, WH Freeman and Company, pp. 469-471.
Kwong et al., (1998). "Structure of an HIV gp120 envelope glycoprotein in complex with the CD4 receptor and a neutralizing human antibody" *Nature* 393:648-659.
Lai et al. (1995). *DNA and Cell Biology* 14:643-651.
Lalvani A. et al., (1997). "Rapid effector Function in CD8 + Memory T Cells," *J. Exp. Med.* 186:859-865.
Lasky et al., (1987). "Delineation of a Region of the Human Immunodeficiency Virus Type 1 gp 120 Glycoprotein Critical for Interaction with the CD4 Receptor," *Cell*50(6):975-985.
Lee et al., (2000). "A single point mutation in HIV-1 V3100p alters the immunogenic properties of rgp120," *Arch Virol.* 145(10):2087-2103.
Levitus et al., (1999). "Main features of DNA-based immunization vectors," *Brazilian Journal of Medical and Biological Research* 32:147-153.
Levy et al., (1984). "Isolation of Lymphocytopathic Retroviruses from San Francisco Patients with AIDS," *Science* 225:840-842.
Littman et al., (1987). "Unusual Intron in the Immunoglobulin Domain of the Newly Isolated Murine CD4 (L3T4) Gene," *Nature* 325(6103):453-455.
Liu, Y., et al., (2006). "Selection on the human immunodeficiency virus type 1 proteome following primary infection," *J. Virol.* 80(19):9519-9529.
Looney et al., (1988). "Type-restricted Neutralization of Molecular Clones of Human Immunodeficiency Virus," *Science* 241:357-359.
Lu et al., (1998). "Immunogenicity of DNA vaccines expressing human immunodeficiency virus type 1 envelope glycoprotein with and without deletions in the V1/2 and V3 regions" *AIDS Res. Hum. Retroviruses* 14(2):151-155.
Maddon et al., (1985). "The Isolation and Nucleotide Sequence of a Cdna Encoding the T Cell Surface Protein T4: a New Member of the Immunoglobulin Gene Family," *Cell* 42(1):93-104.
Maksyutov & Zagrebelnaya, (1993). "ADEPT: a computer program for prediction of protein antigenic determinants," *Comput. Appl. Biosci.* 9(3):291-297.
Malgnan, S., et al. (1998). "Crystal Structures of the Catalytic Domain of HIV-1 Integrase Free and Complexed with its Metal Cofactor: High Level of Similarity of the Active Site with Other Viral Integrases," *Journal of Molecular Biology* 282(2):359-368.
Mammano et al., (1994). "Role of the major homology region of human immunodeficiency virus type 1 in virion morphogenesis" *J. Virol.* 68(8):4927-4936.
Manca et al. (1996). "Antigenicity of HIV derived T Helper Determinants in the Context of Carrier Recombinant Proteins Effect on T Helper Cell Repertoire Selection," *Eur J Immunology* 26(10):2461-2469.
Mascola et al., (1994). "Two antigenically distinct subtypes of human immunodeficiency virus type 1: viral genotype predicts neutralization serotype" *J. Infect. Dis.* 169:48-54.
Matsushita et al., (1988). "Characterization of a human immunodeficiency virus neutralizing monoclonal antibody and mapping of the neutralizing epitope" *J. Virol.* 62:2107-2144.
Matthews (1986). "Restricted neutralization of divergent human T-lymphotropic virus type III isolates by antibodies to the major envelope glycoprotein," *PNAS USA* 83:9709-9713.
Mazumder, A., et al., (1996). "Effects of nucleotide analogues on human immunodeficiency virus type 1 integrase," *Molecular Pharmacology* 49(4):621-628.
Mazza et al., (1992). "Recombinant Interleukin-2 (Ril-2) in Acquired Immune Deficiency Syndrome (AIDS): Preliminary Report in Patients with Lymphoma Associated with HIV Infection," *Eur J Haematol.* 49(1): 1-6.
McCluskie et al. (1999). "Route and method of delivery of DNA vaccine influence immune responses in mice and non-human primates," *Mol Med* 5(5):287-300.
McCornack et al., (1997). "HIV Protease Substrate Conformation: Modulation by Cyclophilin A," *FEBS Letts* 414:84-88.
McDougal et al., (1986). "Binding of the human retrovirus HTLV-III/LAV/ARV/HIV to the CD4 (T4) molecule: conformation dependence, epitope mapping, antibody inhibition, and potential for idiotypic mimicry" *J. Immunol.* 137:2937-2944.
Mcheyzer-Williams, M.G. et al, (1996). "Enumeration and Characterization of Memory Cells in the Th Compartment," *Immunol. Rev.* 150:5-21.
McLain, L., et al., (2001). "Different effects of a single amino acid substitution on three adjacent epitopes in the gp41 C-terminal tall of a neutralizing antibody escape mutant of human immunodeficiency virus type 1," *Arch. Virol.* 146:157-166.
McMichael, A.J. and O'Callaghan, C.A., (1998). "A New Look at T Cells," *J. Exp. Med.* 187(9)1367-1371.
Meister et al., (1995). "Two novel T cell epitope prediction algorithms based on MHC-binding motifs; comparison of predicted and published epitopes from *Mycobacterium tubereculosis* and HIV protein sequences," *Vaccine* 13(6):581-591.
Modrow et al., (1987). "Computer-assisted Analysis of Envelope Protein Sequences of Seven Human Immunodeficiency Virus Isolates: Prediction of Antigenic Epitopes in Conserved and Variable Regions," *J. Virol.* .61(2):570-578.
Montagnier et al., (1984). "Human T-Cell Leukemia Viruses: The Family of Human T-Lymphotropic Retroviruses: Their Role in Malignancies and Association with AIDS," Gallo, Essex & Gross, eds., pp. 363-379.
Montefiori et al., (1999). "Toward an HIV type 1 vaccine that generates potent, broadly cross-reactive neutralizing antibodies" *AIDS Res. Hum. Retroviruses* 15(8):689-698.
Moore et al. (1995). *Vaccine* 13:1741-1749.
Myers et al., (1991). "Human Retroviruses and AIDS," published by the Los Alamos National Laboratory, Los Alamos, NM, , pp. I-A-48 to I-A-56 and 11-77 to 11-88.
Nara et al., (1988). "Purified envelope glycoproteins from human immunodeficiency virus type 1 variants induce individual, type-specific neutralizing antibodies" *J. Virol.* 62:2622-2628.
Nathanson et al. (2000). "Biological Considerations in the Development of a Human Immunodeficiency Virus Vaccine," *J Infect Dis* 182(2):579-589.
Ngo et al. (1994). "The Folding Protein Problem and Tertiary Structure Protein", *Computational complexity, protein structure prediction, and the levinthal paradox*, pp. 492-494.
Novitsky et al., (1999). "Molecular Cloning and Phylogenetic Analysis of Human Immunodeficiency Virus Type 1 Subtype C: a Set of 23 Full-Length Clones from Botswana," *J. Virol.* 73(5):4427-4432.
Nowak and Bangham, (1996). "Population Dynamics of Immune Responses to Persistent Viruses," *Science* 272(5258):74-79.
Odile et al., (Jul. 19-24, 1992). "Anti-HIV Active Immunization, Evidence for Persistent Cell Mediated Immunity after a 2 Year Follow Up," *Eighth International Conference on AIDS/III STD World Congress*, Amsterdam, The Netherlands, Abstract No. MOB 0024.
Okuda et al., (1995). "Induction of Potent Humoral and Cell-mediated Immune Responses Following Direct Injection of DNA Encoding the HIV Type 1 Env and Rev gene Products," *AIDS Res Hum Retroviruses.* 11(8):933-943.
Palaniappan, C. et al., (1997). "Mutations Within the Primer Grip Region of HIV-1 Reverse Transcriptase Result in Loss of RNase H Function," *Journal of Biological Chemistry* 272(17):11157-11164.
Palker et al., (1988). "Type-specific neutralization of the human immunodeficiency virus with antibodies to env-encoded synthetic peptides" *PNAS USA* 85:1932-1936.
Pantaleo, G., and R. A. Koup, (2004). "Correlates of immune protection in HIV-1 infection: what we know, what we don't know, what we should know," *Nat. Med.* 10(8):806-810.
Park et al., (1991). "Overexpression of the Gag-pol Precursor From Human Immunodeficiency Virus Type 1 Proviral Genomes Results in Efficient Proteolytic Processing in The Absence of Virion Production," *J. Virol.* 65:5111.
Patel et al., (1995). "Insights into DNA Polymerization Mechanisms from Structure and Function Analysis of HIV-1 Reverse Transcriptase," *Biochemistry* 34:5351-5363.
Peng et al., (1997). "Enhancement or inhibition of HIV-1 replication by intracellular expression of sense or antisense RNA targeted at different intermediates of reverse transcription" *AIDS* 11:587-595.
Perelson, et al., (1997). "Decay Characteristics of Hiv-I-infected Compartments During Combination Therapy," *Nature* 387(6629):188-191.
Persson, et al. (1998). "Modifications of HIV-1 Retrovirus-like Particles to Enhance Safety and Immunogenicity," *Biologicals* 26:255-265.
Popovic et al., (1984). "Detection, Isolation, and Continuous Production of Cytopathic Retroviruses (HTLV-III) from Patients with AIDS and Pre-AIDS," *Science* 224:497-500.
Prince, HM, (1998). "Gene transfer: review of methods and applications," *Pathology* 30:335-347.
Putney et al., (1986). "HTLV-III/LAV-neutralizing antibodies to an *E. coli*-produced fragment of the virus envelope" *Science* 234:1392-1395.
Pyle et al., (1989). "Immune Response to Immunostimulatory Complexes (ISCOMs) Prepared from Human Immunodeficiency Virus Type 1 (HIV-1) or the HIV-1 External Envelope Glycoprotein (gp 120)," *Vaccine* 7(5):465-473.
Ratner et al., (1985). "Complete nucleotide sequence of the AIDS virus, HTLV-III" *Nature* 313:277-284.
Redfield and Birx, (1992). "Hiv-specific Vaccine Therapy: Concepts, Status, and Future Directions," *AIDS Res Hum Retroviruses* 8(6):1051-1058.
Reicin, A.S. et al., (1995). "Linker Insertion Mutations in the Human Immunodeficiency Virus Type 1 Gag Gene: Effects on Virion Particle Assembly, Release, and Infectivity," *J. Virol.* 69(2):642-650.
Richter, J et al., (2001). "Clinical Gene Therapy in Hematology: Past and Future," *International Journal of Hematology* 73:162-169.
Robert-Guroff et al., (1985). "HTLV-III-neutralizing antibodies in patients with AIDS and AIDS related complex" *Nature* (London) 316:72-74.
Roberts et al., (1996). "Prediction of HIV Peptide Epitopes by a Noval Algorithm," *AIDS Res. Hum. Retroviruses* 12(7):593-610.
Robey, et al., (1986). "Prospect for Prevention of Human Immunodeficiency Virus Infection: Purified 120-kDa Envelope Glycoprotein Induces Neutralizing Antibody," *Proc Natl Acad Sci USA* 83(18):7023-7027.
Rodgers, D. W. et al., (1995). "The Structure of Unliganded Reverse Transcriptase from the Human Immunodeficiency Virus Type 1," *Proc Natl Acad Sci USA* 92(4):1222-1226.
Romano, G et al., (2000). "Latest Developments in gene Transfer Technology: Achievements, Perspectives, and Controversies over Therapeutic Applications," *Stem Cells* 18:19-39.
Rusche et al., (1988). "Antibodies that inhibit fusion of human immunodeficiency virus-infected cells bind a 24-amino acid sequence of the viral envelope, gp120" *PNAS USA* 85:3198-3202.
Russell et al. (1994). *Journal of Molecular Biology*, 244:332-350.
Saag and Kuritzkes, (1996). "Strategies for Continuing Antiretroviral Therapy," *Intl AIDS Society USA* 4(2):16-19.
Saag, et al., (1988). "Extensive Variation of Human Immunodeficiency Virus Type-1 in vivo," *Nature* 334:440-444.
Salk et al., (1987). "Prospects for the Control of AIDS by Immunizing Seropositive Individuals," *Nature* 327(6122):473-476.
Sanchez-Pescador et al., (1985). "Nucleotide sequence and expression of an AIDS-associated retrovirus (ARV-2)" *Science* 227(4686):484-492.
Schernthaner, et al., (1988). "Endosperm-specific Activity of a Zein Gene Promoter in Transgenic Tobacco Plants," *The EMBO J.* 7:1249-1259.
Schneider et al. (Jul. 1997). "Inactivation of the human immunodeficiency virus type 1 inhibitory elements allows Rev-independent expression of Gag and Gag/protease and particle formation." *J Virol.* 71(7):4892-4903.
Schulhafer et al., (1989). "Acquired Immunodeficiency Syndrome: Molecular Biology and its Therapeutic Intervention (review)," In Vivo 1(2):61-78.
Schwartz, et al. (1992) "Mutational inactivation of an inhibitory sequence in human immunodeficiency virus type 1 results in Rev-independent gag expression," *J Virol.* 66(12):7176-7182.
Sheng N. and Dennis, D., (1993) "Active Site Labeling of HIV-1 Reverse Transcriptase," *Biochemistry* 32(18):4938-4942.
Smith et al., (1987). "Blocking of HIV-1 infectivity by a soluble, secreted form of the CD4 antigen," *Science* 238(4834): 1704-1707.
Spence R. A., et al., (1995). "Mechanism of Inhibition of HIV-1 Reverse Transcriptase by Nonnucleoside Inhibitors," *Science* 267(5200):988-993.
Srinivasan et al., (1987). "Molecular Characterization of Human Immunodeficiency Virus from Zaire: Nucleotide Sequence Analysis Identifies Conserved and Variable Domalns in the Envelope Gene," *Gene* 52:71-82.

Stamatatos et al., (1998). "Effect of major deletions in the V1 and V2 loops of a macrophage-tropic HIV type 1 isolate on viral envelope structure, cell entry, and replication" *AIDS Res. Hum. Retroviruses* 14(13):1129-1139.
Stamatatos et al., (1998). "The ability of an oligomeric human immunodeficiency virus type 1 (HIV-1) envelope antigen to elicit neutralizing antibodies against primary HIV•1 isolates is improved following partial deletion of the second hypervariable region" *J. Virol.* 72(10):7840-7845.
Starcich et al., (1986). "Identification and Characterization of Conserved and Variable Regions in the Envelope Gene of HTLV-III/LAV, the Retrovirus of AIDS," *Cell* 45:637-648.
*Stedman's Medical Dictionary*, 26th Edition, Williams & Wilkins, 1995, pp. 852-853.
Steimer et al., (1987). "Genetically Engineered Human Immunodeficiency Envelope Glycoprotein Gp120 Produced in Yeast Is the Target of Neutralizing Antibodies," *Vaccines* 87: 236-241.
Sternberg et al., (1987). "Prediction of Antigenic Determinants and Secondary Structures of the Major AIDS Virus Proteins," *FEBS Letters* 218(2):231-237.
Thali et al., (1993). "Characterization of conserved human immunodeficiency virus type 1 gp120 neutralization epitopes exposed upon gp120-CD4 binding" *J. Virol.* 67(7):3978-3988.
Tindle et al., (1994). "Chimeric Hepatitis B Core Antigen Particles Containing B- and Th-epitopes of Human Papillomavirus Type 16 E7 Protein Induce Specific Antibody and T-helper Responses in Immunised Mice," *Virology* 200:547-557.
Trkola et al., (1995). "Cross-clade neutralization of primary isolates of human immunodeficiency virus type 1 by human monoclonal antibodies and tetrameric CD4-IgG" *J. Virol.* 69(11):6609-6617.
Vacca et al., (1994). "L-735,524: an Orally Bioavailable Human Immunodeficiency Virus Type 1 Protease Inhibitor," *Proc Natl Acad Sci USA* 91(9):4096-4100.
Van Tendeloo et al., (2001). "Gene therapy: principles and applications to hematopoietic cells," *Leukemia* 15:523-544.
Verma et al. (1997). "Gene Therapy-Promises, Problems and Prospects," *Nature* 389(6648):239-242.
Verschoor, (1999). "Comparison of immunity generated by nucleic acid, MF59 and iscom-formulated HIV-1 Gp120 vaccines in rhesus macaques," *Medical Primatology* 28(4/5):Abstract #37.
Vilmer et al., (1984). "Isolation of New Lymphotropic Retrovirus from Two Siblings with Haemophilia B, One with AIDS," *The Lancet* 1:753.
Wagner et al., (1994). "Assembly and Extracellular Release of Chimeric HIV-1 PR55gag Retrovirus-like Particles," *Virology* 200:162-175.
Wagner et al., (1996). "Construction, Expression, and Immunogenicity of Chimeric HIV-1 Virus-like Particles," *Virology* 220:128-140.
Wagner R., et al., (1992) "Studies on Processing, Particle Formation, and Immunogenicity of the HIV-1 gag Gene Product: a Possible Component of a HIV Vaccine," *Arch Virol.* 127:117-137.
Wakefield, J. K. et al., (1992). "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome," *J Virol.* 66(11):6806-6812.
Wan et al., (1996). "Autoprocessing: an Essential Step for the Activation of HIV-1 Protease," *Biochem. J.* 316:569-573.
Wang C. et al., (1998). "Analysis of Minimal Human Immunodeficiency Virus Type 1 Gag Coding Sequences Capable of Virus-like Particle Assembly and Release," *J Virol* 72(10):7950-7959.
Wang et al., (1994). "Assembly of HIV GAG-B-galactosidase fusion proteins into virus particles" *Virology* 200:524-534.
Wang et al., (1995). "Induction of Humoral and Cellular Immune Responses to the Human Immuno-deficiency Type 1 Virus in Non-human Primates by in Vivo DNA Inoculation," *Virology* 211(1):102-112.
Watkins, B. A., et al., (1993). "Immune escape by human immunodeficiency virus type 1 from neutralizing antibodies: evidence for multiple pathways," *J. Virol.* 67(12):7493-7500.
Weiss et al., (1985). "Neutralization of human T-Lymphotropic virus type III by sera of AIDS and AIDS-risk patients" *Nature* (London) 316:69-72.
Weiss et al., (1986). "Variable and conserved neutralization antigens of human immunodeficiency virus" *Nature* (London) 324:572-575.
Welling et al., (1985). "Prediction of sequential antigenic regions in proteins," *FEBS Lett.* 188:215-18.
Wells et al. (1997). *Journal of Leukocyte Biology* 31(5)545-550.
Williamson, et al. (2000). "Designing HIV-I Subtype C Vaccines for South Africa," *South African Journal of Science*, 96:318-324.
Wu X., et al., (1995). "Targeting foreign proteins to human immunodeficiency virus particles via fusion with Vpr and Vpx," *J. Virol.* 69(6):3389-3398.
Wyatt et al., (1995). "Involvement of the V1N2 variable loop structure in the exposure of human immunodeficiency virus type 1 gp120 epitopes induced by receptor binding" *J. Virol.* 69(9):5723-5733.
Wyatt et al., (1998). "The antigenic structure of the HIV gp120 envelope glycoprotein" *Nature* 393:705-711.
Yeni et al., (1993). "Antiretroviral and Immune-based Therapies: Update," *AIDS* 2(Suppl 1):S173-S184.
Yenofsky et al., (1990). "A Mutant Neomycin Phosphotransferase II Gene Reduces the Resistance of Transformants to Antibiotic Selection Pressure," *Proc. Natl. Acad. Sci. USA* 87:3435-3439.
Yourno et al., (1988). "Nucleotide Sequence Analysis of the Env Gene of a New Zairian Isolate of HIV-I," *AIDS Res Hum Retroviruses* 4(3):165-173.
Zagury et al., (1992). "One-year Follow-up of Vaccine Therapy in HIV-infected Immune-deficient Individuals: a New Strategy," *J. AIDS* 5:676-681.
Zagury et al., (Jun. 16-21, 1991). "Progress Report IV on AIDS Vaccine in Human: Phase I Clinical Trial in HIV Infected Patients," *VII International Conference on AIDS*, Florence, Abstract No. M.A. 67.
Zhang Y., et al., (1998). "Analysis of the Assembly Function of the Human Immunodeficiency Virus Type 1 Gag Protein Nucleocapsid Domain," *J Virol* 72(3)1782-1789.
Zhu et al., (1993). "Genotypic and phenotypic characterization of HIV-1 patients with primary infection," *Science* 261:1179-1181.
zur Megede et al., (2000). "Increased Expression and Immunogenicity of Sequence-modified Human Immunodeficiency Virus Type 1 Gag Gene," *J Virol.* 74(6):2628-2635.
zur Megede et al., (2006). "Evaluation of human immunodeficiency type 1 subtype C gag, pol, and gagpol DNA and alphavirus replicon vaccines," *Vaccine* 24:2755-2763.
zur Megede et al., (Jun. 2003). "Expression and Immunogenicity of Sequence-modified Human Immunodeficiency Virus Type 1 Subtype B pol and gagpol DNA Vaccines," *J Virol.* 77(11):6197-6207.
Kalinna BH (1997), "DNA vaccines for parasitic infections," Immuno Cell Bio 75(4):370-375.
United States Office Action mailed May 9, 2012, for U.S. Appl. No. 13/099,219, filed May 2, 2011, 10 pages.
United States Office Action mailed Jun. 5, 2012 U.S. Appl. No. 12/620,511, filed Nov. 17, 2009, 15 pages.
United States Notice of allowance mailed Dec. 20, 2010, for U.S. Appl. No. 12/215,189, filed Jun. 25, 2008, 6 pages.
United States Notice of Allowance mailed Aug. 23, 2010, for U.S. Appl. No. 12/215,189, filed Jun. 25, 2008, 7 pages.
United States Notice of Allowance mailed May 4, 2010, for U.S. Appl. No. 12/215,189 filed Jun. 25, 2008, 8 pages.
Response to United States Office Action mailed Feb. 23, 2010, for U.S. Appl. No. 12/215,189, filed Jun. 25, 2008, 9 pages.
United States Office Action mailed Jan. 27, 2010, for U.S. Appl. No. 12/215,189, filed Jun. 25, 2008, 7 pages.
United States Notice of Abandonment mailed Oct. 4, 2010, for U.S. Appl. No. 09/475,704, filed Dec. 30, 1999, 1 page.
United States Notice of allowance mailed Jun. 17, 2010, for U.S. Appl. No. 09/475,704, filed Dec. 30, 1999, 5 pages.
Response to United States Office Action mailed Mar. 16, 2010, for U.S. Appl. No. 09/475,704, filed Dec. 30, 1999, 5 pages.
United States Office Action mailed Sep. 15, 2009, for U.S. Appl. No. 09/475,704, filed Dec. 30, 1999, 16 pages.
Response to United States Office Ation mailed Jun. 30, 2009, for U.S. Appl. No. 09/475,704, filed Dec. 30, 1999, 10 pages.

Response to United States Office Action mailed Apr. 9, 2009, for U.S. Appl. No. 09/475,704, filed Dec. 30, 1999, 10 pages.
United States Office Action mailed Jan. 16, 2009, for U.S. Appl. No. 09/475,704, filed Dec. 30, 1999, 6 pages.
Response to United States Office Action Mailed Nov. 10, 2006, for U.S. Appl. No. 09/475,704, filed Dec. 30, 1999, 9 pages.
United States Office Action mailed Aug. 12, 2008, for U.S. Appl. No. 09/475,704, filed Dec. 30, 1999, 12 pages.
Response to United States Office Action mailed Jun. 25, 2008, for U.S. Appl. No. 09/475,704, filed Dec. 30, 1999, 8 pages.
United States Office Action mailed Apr. 25, 2008, for U.S. Appl. No. 09/475,704, filed Dec. 30, 1999, 7 pages.
Response to United States Office Ation mailed Jan. 23, 2008, for U.S. Appl. No. 09/475,704, filed Dec. 30, 1999, 12 pages.
United States Office Action mailed Aug. 23, 2007, for U.S. Appl. No. 09/475,704, filed Dec. 30, 1999, 14 pages.
Response to United States Office Action mailed Jun. 13, 2007, for U.S. Appl. No. 09/475,704, filed Dec. 30, 1999, 11 pages.
United States Advisory Action mailed Dec. 15, 2005, for U.S. Appl. No. 09/475,704, filed Dec. 30, 1999, 3 pages.
Resoponse to United States Office Ation mailed Nov. 16, 2006, for U.S. Appl. No. 09/475,704, filed Dec. 30, 1999, 18 pages.
United States Office ation mailed aug. 7, 2006, for U.S. Appl. No. 09/475,704, filed Dec. 30, 1999, 24 pages.
Response to United States Office Action mailed May 16, 2006, for U.S. Appl. No. 09/475,704, filed Dec. 30, 1999, 26 pages.
United States Office Ation mailed Nov. 16, 2005, for U.S. Appl. No. 09/475,704, filed Dec. 30, 1999, 32 pages.
Response to United States Office Action mailed Aug. 22, 2005, for U.S. Appl. No. 09/475,704, filed Dec. 30, 1999, 6 pages.
United states Office Action mailed May 31, 2005, for U.S. Appl. No. 09/475,704, filed Dec. 30, 1999, 32 pages.
Response to United States Office Action mailed Feb. 17, 2005, for U.S. Appl. No. 09/475,704, filed Dec. 30, 1999, 16 pages.
Response to United States Office Action mailed Nov. 1, 2004, for U.S. Appl. No. 09/475,704, filed Dec. 30, 1999, 18 pages.
United States Office Action mailed Jul. 30, 2004, for U.S. Appl. No. 09/475,704, filed Dec. 30, 1999, 39 pages.
United States Advisory Action mailed Feb. 4, 2004, for U.S. Appl. No. 09/475,704, filed Dec. 30, 1999, 3 pages.
Response to United States Office Action mailed Jan. 20, 2004, for U.S. Appl. No. 09/475,704, filed Dec. 30, 1999, 24 pages.
United States Office Action mailed Nov. 17, 2003, for U.S. Appl. No. 09/475,704, filed Dec. 30, 1999, 25 pages.
Resoponse to United States Office Action mailed aug. 26, 2003, for U.S. Appl. No. 09/475,704, filed Dec. 30, 1999, 20 pages.
United States Office Action mailed Feb. 26, 2003, for U.S. Appl. No. 09/475,704, filed Dec. 30, 1999, 16 pages.
Response to United States Office Action mailed Dec. 17, 2002, for U.S. Appl. No. 09/475,704, filed Dec. 30, 1999, 20 pages.
United States Office Action mailed Jul. 18, 2002, for U.S. Appl. No. 09/475704, filed Dec. 30, 1999, 25 pages.
Response to United States Office Action mailed Mar. 13, 2002, for U.S. Appl. No. 09/475,704 filed Dec. 30, 1999, 20 pages.
United states Office action mailed Sep. 13, 2001, for U.S. Appl. No. 09/475,704, filed Dec. 30, 1999, 21 pages.
United States Notice of Allowance mailed Jun. 30, 2009, for U.S. Appl. No. 09/599,575, filed Jul. 5, 2001, 8 pages.
Response to United States Office Action mailed Apr. 8, 2009, for U.S. Appl. No. 09/899,575, Jul. 5, 2001, 10 pages.
United States Office Action mailed Jan. 8, 2009, for U.S. Appl. No. 09/899,575, filed Jul. 5, 2001, 10 pages.
Response to United States Office Ation mailed Sep. 29, 2008, for U.S. Appl. No. 09/899,575, filed Jul. 5, 2001, 24 pages.
United States Office Action mailed Apr. 1, 2006, for U.S. Appl. No. 09/899,575, filed Jul. 5, 2001, 20 pages.
Response to United States Office Action mailed Dec. 6, 2007, for U.S. Appl. No. 09/899,575, filed Jul 5, 2001, 6 pages.
United States Office Action mailed Oct. 19, 2007, for U.S. Appl. No. 09/899,575, filed Jul. 5, 2001, 4 pages.
Response to United States Office Action mailed Jul. 23, 2007, for U.S. Appl. No. 09/899,575, filed Jul. 5, 2001, 10 pages.
United States Office Action mailed Jan. 24, 2007, for U.S. Appl. No. 09/899,575, filed Jul. 5, 2001, 6 pages.
Response to United States Office Action mailed Oct. 23, 2006, for U.S. Appl. No. 09/899,575, filed Jul. 5, 2001, 15 pages.
Response to United States Office Action mailed Oct. 4, 2006, for U.S. Appl. No. 09/899,575, filed Jul. 5, 2001, 10 pages.
United States Office Action mailed Apr. 4, 2006, for U.S. Appl. No. 09/899,575, filed Jul. 5, 2001, 9 pages.
Supplemental Response to United States Office Action mailed Aug. 31, 2005, for U.S. Appl. No. 09/899,575, filed Jul. 5, 2001, 29 pages.
Response to United States Office Action mailed Aug. 30, 2005, for U.S. Appl. No. 09/899,575, filed Jul. 5, 2001, 5 pages.
United States Office Action mailed Jun. 2, 2005, for U.S. Appl. No. 09/899,575, filed Jul. 5, 2001, 11 pages.
United States Notice of Allowance mailed Dec. 27, 2010, for U.S. Appl. No. 09/610,313, filed Jul. 5, 2000, 12 pages.
Response to United States Office Action mailed Dec. 8, 2010, for U.S. Appl. No. 09/610,313, filed Jul. 5, 2000, 3 pages.
United States Office Action mailed Sep. 8, 2010, for U.S. Appl. No. 09/610,313, filed Jul. 5, 2000, 7 pages.
Response to United States Office Action mailed Jun. 23, 2010, for U.S. Appl. No. 09/610,313, filed Jul. 5, 2000, 10 pages.
United States Office Action mailed Mar. 29, 2010, for U.S. Appl. No. 09/6610,313, filed Jul. 5, 2000, 6 pages.
Arguments Accompanying United States Appeal Brief Request mailed Jan. 12, 2010, for U.S. Appl. No. 09/610,313, filed Jul. 5, 2000, 5 pages.
United States Office Action mailed Oct. 14, 2009, for U.S. Appl. No. 09/610,313, filed Jul. 5, 2000, 8 pages.
Response to United States Office Action mailed Jun. 22, 2009, for U.S. Appl. No. 09/610,313, filed Jul. 5, 2000, 11 pages.
United States Office Action mailed Jan. 23, 2009, for U.S. Appl. No. 09/610,313, filed Jul. 5, 2000, 9 pages.
Response to United States Office Action mailed Oct. 23, 2006, for U.S. Appl. No. 09/610,313, filed Jul. 5, 2000, 7 pages.
Response to United States Office Action mailed Mar. 19, 2008, for U.S. Appl. No. 09/610,313, filed Jul. 5, 2000, 7 pages.
United States Office Action mailed Dec. 31, 2007, for U.S. Appl. No. 09/610,313, filed Jul. 5, 2000, 14 pages.
Response to United States Office Action mailed Oct. 8, 2007, for U.S. Appl. No. 09/610,313, filed Jul. 5, 2000, 8 pages.
United States Advisory Action mailed Mar. 21, 2007, for U.S. Appl. No. 09/610,313, filed Jul. 5, 2000, 4 pages.
Response to United States Office Action mailed Mar. 5, 2007, for U.S. Appl. No. 09/610,313, filed Jul. 5, 2000, 18 pages.
United States Office Action mailed Oct. 5, 2006, for U.S. Appl. No. 09/610,313, filed Jul. 5, 2000, 19 pages.
Response to United States Office Action mailed Jul. 17, 2006, for U.S. Appl. No. 09/610,313, filed Jul. 5, 2000, 10 pages.
United States Office Action mailed Feb. 15, 2006, for U.S. Appl. No. 09/610,313, filed Jul. 5, 2000, 20 pages.
Response to United States Office Action mailed Dec. 9, 2005, for U.S. Appl. No. 09/610,313, filed Jul. 5, 2000, 12 pages.
United States Office Action mailed Aug. 9, 2005, for U.S. Appl. No. 09/610,313, filed Jul. 5, 2000, 26 pages.
United States Advisory Action mailed Oct. 25, 2004, for U.S. Appl. No. 09/610,313, filed Jul. 5, 2000, 3 pages.
Response to United States Office Action mailed Oct. 14, 2004, for U.S. Appl. No. 09/610,313, filed Jul. 5, 2000, 12 pages.
United States Office Action mailed Jun. 14, 2004, for U.S. Appl. No. 09/610,313, filed Jul. 5, 2000, 26 pages.
Response to United States Office Action mailed Mar. 26, 2004, for U.S. Appl. No. 09/610,313, filed Jul. 5, 2000, 22 pages.
United States Office Action mailed Nov. 28, 2003, for U.S. Appl. No. 09/610,313, filed Jul. 5, 2000, 18 pages.
Response to United States Office Action mailed Sep. 4, 2003, for U.S. Appl. No. 09/610,313, filed Jul. 5, 2000, 22 pages.
United States Office Action mailed Mar. 4, 2003, for U.S. Appl. No. 09/610,313, filed Jul. 5, 2000, 18 pages.
Response to United States Office Action mailed Dec. 18, 2002, for U.S. Appl. No. 09/610,313, filed Jul. 5, 2000, 9 pages.
United States Advisory Action mailed Nov. 6, 2002, for U.S. Appl. No. 09/610,313, filed Jul. 5, 2000, 3 pages.

Response to United States Office Action mailed Oct. 18, 2002, for U.S. Appl. No. 09/610,313, filed Jul. 5, 2000, 15 pages.
United States Office Action mailed Jun. 18, 2002, for U.S. Appl. No. 09/610,313, filed Jul. 5, 2000, 23 pages.
Response to United States Office Action mailed Mar. 21, 2002, for U.S. Appl. No. 09/610,313, filed Jul. 5, 2000, 19 pages.
United States Office Action mailed Sep. 21, 2001, for U.S. Appl. No. 09/610,313, filed Jul. 5, 2000, 24 pages.

Gag_AF110965_BW_mod
ATGGGCGCCCGCGCCAGCATCCTGCGCGGCGGCAAGCTGGACGCCTGGGAGCGCATCCGCC
TGCGCCCCGGCGGCAAGAAGTGCTACATGATGAAGCACCTGGTGTGGGCCAGCCGCGAGCT
GGAGAAGTTCGCCCTGAACCCCGGCCTGCTGGAGACCAGCGAGGGCTGCAAGCAGATCATC
CGCCAGCTGCACCCCGCCCTGCAGACCGGCAGCGAGGAGCTGAAGAGCCTGTTCAACACCG
TGGCCACCCTGTACTGCGTGCACGAGAAGATCGAGGTCCGCGACACCAAGGAGGCCCTGGA
CAAGATCGAGGAGGAGCAGAACAAGTGCCAGCAGAAGATCCAGCAGGCCGAGGCCGCCGAC
AAGGGCAAGGTGAGCCAGAACTACCCCATCGTGCAGAACCTGCAGGGCCAGATGGTGCACC
AGGCCATCAGCCCCCGCACCCTGAACGCCTGGGTGAAGGTGATCGAGGAGAAGGCCTTCAG
CCCCGAGGTGATCCCCATGTTCACCGCCCTGAGCGAGGGCGCCACCCCCCAGGACCTGAAC
ACGATGTTGAACACCGTGGGCGGCCACCAGGCCGCCATGCAGATGCTGAAGGACACCATCA
ACGAGGAGGCCGCCGAGTGGGACCGCGTGCACCCCGTGCACGCCGGCCCCATCGCCCCCGG
CCAGATGCGCGAGCCCCGCGGCAGCGACATCGCCGGCACCACCAGCACCCTGCAGGAGCAG
ATCGCCTGGATGACCAGCAACCCCCCCATCCCCGTGGGCGACATCTACAAGCGGTGGATCA
TCCTGGGCCTGAACAAGATCGTGCGGATGTACAGCCCCGTGAGCATCCTGGACATCAAGCA
GGGCCCCAAGGAGCCCTTCCGCGACTACGTGGACCGCTTCTTCAAGACCCTGCGCGCCGAG
CAGAGCACCCAGGAGGTGAAGAACTGGATGACCGACACCCTGCTGGTGCAGAACGCCAACC
CCGACTGCAAGACCATCCTGCGCGCTCTCGGCCCCGGCGCCAGCCTGGAGGAGATGATGAC
CGCCTGCCAGGGCGTGGGCGGCCCCAGCCACAAGGCCCGCGTGCTGGCCGAGGCGATGAGC
CAGGCCAACACCAGCGTGATGATGCAGAAGAGCAACTTCAAGGGCCCCCGGCGCATCGTCA
AGTGCTTCAACTGCGGCAAGGAGGGCCACATCGCCCGCAACTGCCGCGCCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAGCC
GCCCCGAGCCCACCGCCCCCCCCGCCGAGAGCTTCCGCTTCGAGGAGACCACCCCCGGCCA
GAAGCAGGAGAGCAAGGACCGCGAGACCCTGACCAGCCTGAAGAGCCTGTTCGGCAACGAC
CCCCTGAGCCAGTAA

FIG. 1

Gag_AF110967_BW_mod
ATGGGCGCCCGCGCCAGCATCCTGCGCGGCGAGAAGCTGGACAAGTGGGAGAAGATCCGCC
TGCGCCCCGGCGGCAAGAAGCACTACATGCTGAAGCACCTGGTGTGGGCCAGCCGCGAGCT
GGAGGGCTTCGCCCTGAACCCCGGCCTGCTGGAGACCGCCGAGGGCTGCAAGCAGATCATG
AAGCAGCTGCAGCCCGCCCTGCAGACCGGCACCGAGGAGCTGCGCAGCCTGTACAACACCG
TGGCCACCCTGTACTGCGTGCACGCCGGCATCGAGGTCCGCGACACCAAGGAGGCCCTGGA
CAAGATCGAGGAGGAGCAGAACAAGTCCCAGCAGAAGACCCAGCAGGCCAAGGAGGCCGAC
GGCAAGGTGAGCCAGAACTACCCCATCGTGCAGAACCTGCAGGGCCAGATGGTGCACCAGG
CCATCAGCCCCCGCACCCTGAACGCCTGGGTGAAGGTGATCGAGGAGAAGGCCTTCAGCCC
CGAGGTGATCCCCATGTTCACCGCCCTGAGCGAGGGCGCCACCCCCCAGGACCTGAACACG
ATGTTGAACACCGTGGGCGGCCACCAGGCCGCCATGCAGATGCTGAAGGACACCATCAACG
AGGAGGCCGCCGAGTGGGACCGCCTGCACCCCGTGCAGGCCGGCCCCGTGGCCCCCGGCCA
GATGCGCGACCCCCGCGGCAGCGACATCGCCGGCGCCACCAGCACCCTGCAGGAGCAGATC
GCCTGGATGACCAGCAACCCCCCCGTGCCCGTGGGCGACATCTACAAGCGGTGGATCATCC
TGGGCCTGAACAAGATCGTGCGGATGTACAGCCCCGTGAGCATCCTGGACATCCGCCAGGG
CCCCAAGGAGCCCTTCCGCGACTACGTGGACCGCTTCTTCAAGACCCTGCGCGCCGAGCAG
GCCACCCAGGACGTGAAGAACTGGATGACCGAGACCCTGCTGGTGCAGAACGCCAACCCCG
ACTGCAAGACCATCCTGCGCGCTCTCGGCCCCGGCGCCACCCTGGAGGAGATGATGACCGC
CTGCCAGGGCGTGGGCGGCCCCGGCCACAAGGCCCGCGTGCTGGCCGAGGCGATGAGCCAG
GCCAACAGCGTGAACATCATGATGCAGAAGAGCAACTTCAAGGGCCCCCGGCGCAACGTCA
AGTGCTTCAACTGCGGCAAGGAGGGCCACATCGCCAAGAACTGCCGCGCCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAACC
GCAGCGAGCCCGCCGCCCCCACCGTGCCCACCGCCCCCCCCGCCGAGAGCTTCCGCTTCGA
GGAGACCACCCCCGCCCCCAAGCAGGAGCCCAAGGACCGCGAGCCCTACCGCGAGCCCCTG
ACCGCCCTGCGCAGCCTGTTCGGCAGCGGCCCCCTGAGCCAGTAA

FIG. 2

Env_AF110968_C_BW_opt

```
--> signal peptide (1-81)
ATGCGCGTGATGGGCATCCTGAAGAACTACCAGCAGTGGTGGATGTGGGGCATCCTGGGCTTCTGGATGCTGATCA
    \/--> gp120/140/160 (82)
TCAGCAGCGTGGTGGGCAACCTGTGGGTGACCGTGTACTACGGCGTGCCCGTGTGGAAGGAGGCCAAGACCACCCT
GTTCTGCACCAGCGACGCCAAGGCCTACGAGACCGAGGTGCACAACGTGTGGGCCACCCACGCCTGCGTGCCCACC
GACCCCAACCCCCAGGAGATCGTGCTGGAGAACGTGACCGAGAACTTCAACATGTGGAAGAACGACATGGTGGACC
AGATGCACGAGGACATCATCAGCCTGTGGGACCAGAGCCTGAAGCCCTGCGTGAAGCTGACCCCCCTGTGCGTGAC
CCTGAAGTGCCGCAACGTGAACGCCACCAACAACATCAACAGCATGATCGACAACAGCAACAAGGGCGAGATGAAG
AACTGCAGCTTCAACGTGACCACCGAGCTGCGCGACCGCAAGCAGGAGGTGCACGCCCTGTTCTACCGCCTGGACG
TGGTGCCCCTGCAGGGCAACAACAGCAACGAGTACCGCCTGATCAACTGCAACACCAGCGCCATCACCCAGGCCTG
CCCCAAGGTGAGCTTCGACCCCATCCCCATCCACTACTGCACCCCCGCCGGCTACGCCATCCTGAAGTGCAACAAC
CAGACCTTCAACGGCACCGGCCCCTGCAACAACGTGAGCAGCGTGCAGTGCGCCCACGGCATCAAGCCCGTGGTGA
GCACCCAGCTGCTGCTGAACGGCAGCCTGGCCAAGGGCGAGATCATCATCCGCAGCGAGAACCTGGCCAACAACGC
CAAGATCATCATCGTGCAGCTGAACAAGCCCGTGAAGATCGTGTGCGTGCGCCCCAACAACAACACCCGCAAGAGC
GTGCGCATCGGCCCCGGCCAGACCTTCTACGCCACCGGCGAGATCATCGGCGACATCCGCCAGGCCTACTGCATCA
TCAACAAGACCGAGTGGAACAGCACCCTGCAGGGCGTGAGCAAGAAGCTGGAGGAGCACTTCAGCAAGAAGGCCAT
CAAGTTCGAGCCCAGCAGCGGCGGCGACCTGGAGATCACCACCCACAGCTTCAACTGCCGCGGCGAGTTCTTCTAC
TGCGACACCAGCCAGCTGTTCAACAGCACCTACAGCCCCAGCTTCAACGGCACCGAGAACAAGCTGAACGGCACCA
TCACCATCACCTGCCGCATCAAGCAGATCATCAACATGTGGCAGAAGGTGGGCCGCGCCATGTACGCCCCCCCCAT
CGCCGGCAACCTGACCTGCGAGAGCAACATCACCGGCCTGCTGCTGACCCGCGACGGCGGCAAGACCGGCCCCAAC
GACACCGAGATCTTCCGCCCCGGCGGCGGCGACATGCGCGACAACTGGCGCAACGAGCTGTACAAGTACAAGGTGG
                                                        gp120(1512)<--\/-->(1513)gp41
TGGAGATCAAGCCCCTGGGCGTGGCCCCCACCGAGGCCAAGCGCCGCGTGGTGGAGCGCGAGAAGCGCGCCGTGGG
CATCGGCGCCGTGTTCCTGGGCTTCCTGGGCGCCGCCGGCAGCACCATGGGCGCCGCCAGCATCACCCTGACCGTG
CAGGCCCGCCTGCTGCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGACCCGCATCCTGGCCGTGGAGCGCTACCTGAAGGACCA
GCAGCTGCTGGGCATCTGGGGCTGCAGCGGCAAGCTGATCTGCACCACCGCCGTGCCCTGGAACAGCAGCTGGAGC
AACCGCAGCCACGACGAGATCTGGGACAACATGACCTGGATGCAGTGGGACCGCGAGATCAACAACTACACCGACA
CCATCTACCGCCTGCTGGAGGAGAGCCAGAACCAGCAGGAGAAGAACGAGAAGGACCTGCTGGCCCTGGACAGCTG
                                   gp140(2025)<--\/
GCAGAACCTGTGGAACTGGTTCAGCATCACCAACTGGCTGTGGTACATCAAGATCTTCATCATGATCGTGGGCGGC
CTGATCGGCCTGCGCATCATCTTCGCCGTGCTGAGCATCGTGAACCGCGTGCGCCAGGGCTACAGCCCCCTGCCCT
TCCAGACCCTGACCCCCAACCCCCGCGAGCCCGACCGCCTGGGCCGCATCGAGGAGGAGGGCGGCGAGCAGGACCG
CGGCCGCAGCATCCGCCTGGTGAGCGGCTTCCTGGCCCTGGCCTGGGACGACCTGCGCAGCCTGTGCCTGTTCAGC
TACCACCGCCTGCGCGACTTCATCCTGATCGCCGCCCGCGTGCTGGAGCTGCTGGGCCAGCGCGGCTGGGAGGCCC
TGAAGTACCTGGGCAGCCTGGTGCAGTACTGGGGCCTGGAGCTGAAGAAGAGCGCCATCAGCCTGCTGGACACCAT
CGCCATCGCCGTGGCCGAGGGCACCGACCGCATCATCGAGTTCATCCAGCGCATCTGCCGCGCCATCCGCAACATC
                  gp160, gp41(2547)<--\
CCCCGCCGCATCCGCCAGGGCTTCGAGGCCGCCCTGCAGTAA
```

FIG. 3

Env_AF110975_C_BW_opt

--> signal peptide (1-72) \/-->
ATGCGCGTGCGCGGCATCCTGCGCAGCTGGCAGCAGTGGTGGATCTGGGGCATCCTGGGCTTCTGGATCTGCAGCG
gp120/140/160 (72)
GCCTGGGCAACCTGTGGGTGACCGTGTACGACGGCGTGCCCGTGTGGCGCGAGGCCAGCACCACCCTGTTCTGCGC
CAGCGACGCCAAGGCCTACGAGAAGGAGGTGCACAACGTGTGGGCCACCCACGCCTGCGTGCCCACCGACCCCAAC
CCCCAGGAGATCGAGCTGGACAACGTGACCGAGAACTTCAACATGTGGAAGAACGACATGGTGGACCAGATGCACG
AGGACATCATCAGCCTGTGGGACCAGAGCCTGAAGCCCCGCGTGAAGCTGACCCCCCTGTGCGTGACCCTGAAGTG
CACCAACTACAGCACCAACTACAGCAACACCATGAACGCCACCAGCTACAACAACAACACCACCGAGGAGATCAAG
AACTGCACCTTCAACATGACCACCGAGCTGCGCGACAAGAAGCAGCAGGTGTACGCCCTGTTCTACAAGCTGGACA
TCGTGCCCCTGAACAGCAACAGCAGCGAGTACCGCCTGATCAACTGCAACACCAGCGCCATCACCCAGGCCTGCCC
CAAGGTGAGCTTCGACCCCATCCCCATCCACTACTGCGCCCCCGCCGGCTACGCCATCCTGAAGTGCAAGAACAAC
ACCAGCAACGGCACCGGCCCCTGCCAGAACGTGAGCACCGTGCAGTGCACCCACGGCATCAAGCCCGTGGTGAGCA
CCCCCCTGCTGCTGAACGGCAGCCTGGCCGAGGGCGGCGAGATCATCATCCGCAGCAAGAACCTGAGCAACAACGC
CTACACCATCATCGTGCACCTGAACGACAGCGTGGAGATCGTGTGCACCCGCCCCAACAACAACACCCGCAAGGGC
ATCCGCATCGGCCCCGGCCAGACCTTCTACGCCACCGAGAACATCATCGGCGACATCCGCCAGGCCCACTGCAACA
TCAGCGCCGGCGAGTGGAACAAGGCCGTGCAGCGCGTGAGCGCCAAGCTGCGCGAGCACTTCCCCAACAAGACCAT
CGAGTTCCAGCCCAGCAGCGGCGGCGACCTGGAGATCACCACCCACAGCTTCAACTGCCGCGGCGAGTTCTTCTAC
TGCAACACCAGCAAGCTGTTCAACAGCAGCTACAACGGCACCAGCTACCGCGGCACCGAGAGCAACAGCAGCATCA
TCACCCTGCCCTGCCGCATCAAGCAGATCATCGACATGTGGCAGAAGGTGGGCCGCGCCATCTACGCCCCCCCCAT
CGAGGGCAACATCACCTGCAGCAGCAGCATCACCGGCCTGCTGCTGGCCCGCGACGGCGGCCTGGACAACATCACC
ACCGAGATCTTCCGCCCCCAGGGCGGCGACATGAAGGACAACTGGCGCAACGAGCTGTACAAGTACAAGGTGGTGG
gp120 (1509)<--\/-->(1510) gp41
AGATCAAGCCCCTGGGCGTGGCCCCCACCGAGGCCAAGCGCCGCGTGGTGGAGCGCGAGAAGCGCGCCGTGGGCAT
CGGCGCCGTGATCTTCGGCTTCCTGGGCGCCGCCGGCAGCAACATGGGCGCCGCCAGCATCACCCTGACCGCCCAG
GCCCGCCAGCTGCTGAGCGGCATCGTGCAGCAGCAGAGCAACCTGCTGCGCGCCATCGAGGCCCAGCAGCACATGC
TGCAGCTGACCGTGTGGGGCATCAAGCAGCTGCAGGCCCGCGTGCTGGCCATCGAGCGCTACCTGAAGGACCAGCA
GCTGCTGGGCATCTGGGGCTGCAGCGGCAAGCTGATCTGCACCACCACCGTGCCCTGGAACAGCAGCTGGAGCAAC
AAGACCCAGGGCGAGATCTGGGAGAACATGACCTGGATGCAGTGGGACAAGGAGATCAGCAACTACACCGGCATCA
TCTACCGCCTGCTGGAGGAGAGCCAGAACCAGCAGGAGCAGAACGAGAAGGACCTGCTGGCCCTGGACAGCCGCAA
gp140 (2022)<--\/
CAACCTGTGGAGCTGGTTCAACATCAGCAACTGGCTGTGGTACATCAAGATCTTCATCATGATCGTGGGCGGCCTG
ATCGGCCTGCGCATCATCTTCGCCGTGCTGAGCATCGTGAACCGCGTGCGCCAGGGCTACAGCCCCCTGAGCTTCC
AGACCCTGACCCCCAACCCCCGCGGCCTGGACCGCCTGGGCCGCATCGAGGAGGAGGGCGGCGAGCAGGACCGCGA
CCGCAGCATCCGCCTGGTGCAGGGCTTCCTGGCCCTGGCCTGGGACGACCTGCGCAGCCTGTGCCTGTTCAGCTAC
CACCGCCTGCGCGACCTGATCCTGGTGACCGCCCGCGTGGTGGAGCTGCTGGGCCGCAGCAGCCCCCGCGGCCTGC
AGCGCGGCTGGGAGGCCCTGAAGTACCTGGGCAGCCTGGTGCAGTACTGGGGCCTGGAGCTGAAGAAGAGCGCCAC
CAGCCTGCTGGACAGCATCGCCATCGCCGTGGCCGAGGGCACCGACCGCATCATCGAGGTGATCCAGCGCATCTAC
gp160, gp41 (2565)<--\
CGCGCCTTCTGCAACATCCCCCGCCGCGTGCGCCAGGGCTTCGAGGCCGCCCTGCAGTAA

FIG. 4

Gag_AF110965_BW_opt

ATGGGCGCCCGCGCCAGCATCCTGCGCGGCGGCAAGCTGGACGCCTGGGAGCGCATCCGCCTGCGCCCCGG

CGGCAAGAAGTGCTACATGATGAAGCACCTGGTGTGGGCCAGCCGCGAGCTGGAGAAGTTCGCCCTGAACC

CCGGCCTGCTGGAGACCAGCGAGGGCTGCAAGCAGATCATCCGCCAGCTGCACCCCGCCCTGCAGACCGGC

AGCGAGGAGCTGAAGAGCCTGTTCAACACCGTGGCCACCCTGTACTGCGTGCACGAGAAGATCGAGGTGCG
C

CGACACCAAGGAGGCCCTGGACAAGATCGAGGAGGAGCAGAACAAGAGCCAGCAGAAGATCCAGCAGGCCG

AGGCCGCCGACAAGGGCAAGGTGAGCCAGAACTACCCCATCGTGCAGAACCTGCAGGGCCAGATGGTGCAC

CAGGCCATCAGCCCCCGCACCCTGAACGCCTGGGTGAAGGTGATCGAGGAGAAGGCCTTCAGCCCCGAGGT

GATCCCCATGTTCACCGCCCTGAGCGAGGGCGCCACCCCCCAGGACCTGAACACCATGCTGAACACCGTGG
G T

GCGGCCACCAGGCCGCCATGCAGATGCTGAAGGACACCATCAACGAGGAGGCCGCCGAGTGGGACCGCGTG

CACCCCGTGCACGCCGGCCCCATCGCCCCCGGCCAGATGCGCGAGCCCCGCGGCAGCGACATCGCCGGCAC

CACCAGCACCCTGCAGGAGCAGATCGCCTGGATGACCAGCAACCCCCCCATCCCCGTGGGCGACATCTACA

AGCGCTGGATCATCCTGGGCCTGAACAAGATCGTGCGCATGTACAGCCCCGTGAGCATCCTGGACATCAAG
G G

CAGGGCCCCAAGGAGCCCTTCCGCGACTACGTGGACCGCTTCTTCAAGACCCTGCGCGCCGAGCAGAGCAC

CCAGGAGGTGAAGAACTGGATGACCGACACCCTGCTGGTGCAGAACGCCAACCCCGACTGCAAGACCATCC

TGCGCGCCCTGGGCCCCGGCGCCAGCCTGGAGGAGATGATGACCGCCTGCCAGGGCGTGGGCGGCCCCAGC
T C

CACAAGGCCCGCGTGCTGGCCGAGGCCATGAGCCAGGCCAACACCAGCGTGATGATGCAGAAGAGCAACTT
G

CAAGGGCCCCCGCCGCATCGTGAAGTGCTTCAACTGCGGCAAGGAGGGCCACATCGCCCGCAACTGCCGCG
G C

CCCCCCGCAAGAAGGGCTGCTGGAAGTGCGGCAAGGAGGGCCACCAGATGAAGGACTGCACCGAGCGCCAG

GCCAACTTCCTGGGCAAGATCTGGCCCAGCCACAAGGGCCGCCCCGGCAACTTCCTGCAGAGCCGCCCCGA

GCCCACCGCCCCCCCCGCCGAGAGCTTCCGCTTCGAGGAGACCACCCCCGGCCAGAAGCAGGAGAGCAAGG

ACCGCGAGACCCTGACCAGCCTGAAGAGCCTGTTCGGCAACGACCCCCTGAGCCAGTAA

FIG. 5

Gag_AF110967_BW_opt

ATGGGCGCCCGCGCCAGCATCCTGCGCGGCGAGAAGCTGGACAAGTGGGAGAAGATCCGCCTGCGCCCCGG

CGGCAAGAAGCACTACATGCTGAAGCACCTGGTGTGGGCCAGCCGCGAGCTGGAGGGCTTCGCCCTGAACC

CCGGCCTGCTGGAGACCGCCGAGGGCTGCAAGCAGATCATGAAGCAGCTGCAGCCCGCCCTGCAGACCGGC

ACCGAGGAGCTGCGCAGCCTGTACAACACCGTGGCCACCCTGTACTGCGTGCACGCCGGCATCGAGGTGCG
C

CGACACCAAGGAGGCCCTGGACAAGATCGAGGAGGAGCAGAACAAGAGCCAGCAGAAGACCCAGCAGGCCA
TC

AGGAGGCCGACGGCAAGGTGAGCCAGAACTACCCCATCGTGCAGAACCTGCAGGGCCAGATGGTGCACCAG

GCCATCAGCCCCCGCACCCTGAACGCCTGGGTGAAGGTGATCGAGGAGAAGGCCTTCAGCCCCGAGGTGAT

CCCCATGTTCACCGCCCTGAGCGAGGGCGCCACCCCCCAGGACCTGAACACCATGCTGAACACCGTGGGCG
G T

GCCACCAGGCCGCCATGCAGATGCTGAAGGACACCATCAACGAGGAGGCCGCCGAGTGGGACCGCCTGCAC

CCCGTGCAGGCCGGCCCCGTGGCCCCCGGCCAGATGCGCGACCCCCGCGGCAGCGACATCGCCGGCGCCAC

CAGCACCCTGCAGGAGCAGATCGCCTGGATGACCAGCAACCCCCCCGTGCCCGTGGGCGACATCTACAAGC

GCTGGATCATCCTGGGCCTGAACAAGATCGTGCGCATGTACAGCCCCGTGAGCATCCTGGACATCCGCCAG
G G

GGCCCCAAGGAGCCCTTCCGCGACTACGTGGACCGCTTCTTCAAGACCCTGCGCGCCGAGCAGGCCACCCA

GGACGTGAAGAACTGGATGACCGAGACCCTGCTGGTGCAGAACGCCAACCCCGACTGCAAGACCATCCTGC

GCGCCCTGGGCCCCGGCGCCACCCTGGAGGAGATGATGACCGCCTGCCAGGGCGTGGGCGGCCCCGGCCAC
T C

AAGGCCCGCGTGCTGGCCGAGGCCATGAGCCAGGCCAACAGCGTGAACATCATGATGCAGAAGAGCAACTT
G

CAAGGGCCCCCGCCGCAACGTGAAGTGCTTCAACTGCGGCAAGGAGGGCCACATCGCCAAGAACTGCCGCG
G C

CCCCCCGCAAGAAGGGCTGCTGGAAGTGCGGCAAGGAGGGCCACCAGATGAAGGACTGCACCGAGCGCCAG

GCCAACTTCCTGGGCAAGATCTGGCCCAGCCACAAGGGCCGCCCCGGCAACTTCCTGCAGAACCGCAGCGA

GCCCGCCGCCCCCACCGTGCCCACCGCCCCCCCGCCGAGAGCTTCCGCTTCGAGGAGACCACCCCCGCCC

CCAAGCAGGAGCCCAAGGACCGCGAGCCCTACCGCGAGCCCCTGACCGCCCTGCGCAGCCTGTTCGGCAGC

GGCCCCCTGAGCCAGTAA

FIG. 6

SEQUENCE LISTING

<160> NUMBER OF SEQ ID NOS: 30

<210> SEQ ID NO 1
<211> LENGTH: 60
<212> TYPE: DNA
<213> ORGANISM: Human immunodeficiency virus

<400> SEQUENCE: 1
gacatcaagc agggccccaa ggagcccttc cgcgactacg tggaccgctt cttcaagacc 60

<210> SEQ ID NO 2
<211> LENGTH: 60
<212> TYPE: DNA
<213> ORGANISM: Human immunodeficiency virus

<400> SEQUENCE: 2
gacatccgcc agggccccaa ggagcccttc cgcgactacg tggaccgctt cttcaagacc 60

<210> SEQ ID NO 3
<211> LENGTH: 1479
<212> TYPE: DNA
<213> ORGANISM: Artificial Sequence
<220> FEATURE:
<223> OTHER INFORMATION: synthetic Gag of HIV strain AF110965

<400> SEQUENCE: 3
atgggcgccc gcgccagcat cctgcgcggc ggcaagctgg acgcctggga gcgcatccgc 60
ctgcgccccg gcggcaagaa gtgctacatg atgaagcacc tggtgtgggc cagccgcgag 120
ctggagaagt tcgccctgaa ccccggcctg ctggagacca gcgagggctg caagcagatc 180
atccgccagc tgcaccccgc cctgcagacc ggcagcgagg agctgaagag cctgttcaac 240
accgtggcca ccctgtactg cgtgcacgag aagatcgagg tccgcgacac caaggaggcc 300
ctggacaaga tcgaggagga gcagaacaag tgccagcaga agatccagca ggccgaggcc 360
gccgacaagg gcaaggtgag ccagaactac cccatcgtgc agaacctgca gggccagatg 420
gtgcaccagg ccatcagccc ccgcaccctg aacgcctggg tgaaggtgat cgaggagaag 480
gccttcagcc ccgaggtgat ccccatgttc accgccctga gcgagggcgc caccccccag 540
gacctgaaca cgatgttgaa caccgtgggc ggccaccagg ccgccatgca gatgctgaag 600
gacaccatca acgaggaggc cgccgagtgg gaccgcgtgc accccgtgca cgccggcccc 660
atcgcccccg gccagatgcg cgagccccgc ggcagcgaca tcgccggcac caccagcacc 720
ctgcaggagc agatcgcctg gatgaccagc aacccccccca tccccgtggg cgacatctac 780
aagcggtgga tcatcctggg cctgaacaag atcgtgcgga tgtacagccc cgtgagcatc 840
ctggacatca agcagggccc caaggagccc ttccgcgact acgtggaccg cttcttcaag 900
accctgcgcg ccgagcagag cacccaggag gtgaagaact ggatgaccga caccctgctg 960
gtgcagaacg ccaaccccga ctgcaagacc atcctgcgcg ctctcggccc cggcgccagc 1020
ctggaggaga tgatgaccgc ctgccagggc gtgggcggcc ccagccacaa ggcccgcgtg 1080
ctggccgagg cgatgagcca ggccaacacc agcgtgatga tgcagaagag caacttcaag 1140
ggcccccggc gcatcgtcaa gtgcttcaac tgcggcaagg agggccacat cgcccgcaac 1200
tgccgcgccc cccgcaagaa gggctgctgg aagtgcggca aggagggcca ccagatgaag 1260
gactgcaccg agcgccaggc caacttcctg ggcaagatct ggcccagcca caagggccgc 1320
cccggcaact tcctgcagag ccgccccgag cccaccgccc cccccgccga gagcttccgc 1380

```
ttcgaggaga ccaccccgg ccagaagcag gagagcaagg accgcgagac cctgaccagc   1440
ctgaagagcc tgttcggcaa cgaccccctg agccagtaa                         1479

<210> SEQ ID NO 4
<211> LENGTH: 1509
<212> TYPE: DNA
<213> ORGANISM: Artificial Sequence
<220> FEATURE:
<223> OTHER INFORMATION: synthetic Gag of HIV strain AF110967

<400> SEQUENCE: 4
atgggcgccc gcgccagcat cctgcgcggc gagaagctgg acaagtggga gaagatccgc     60
ctgcgccccg gcggcaagaa gcactacatg ctgaagcacc tggtgtgggc cagccgcgag    120
ctggagggct tcgccctgaa ccccggcctg ctggagaccg ccgagggctg caagcagatc    180
atgaagcagc tgcagcccgc cctgcagacc ggcaccgagg agctgcgcag cctgtacaac    240
accgtggcca ccctgtactg cgtgcacgcc ggcatcgagg tccgcgacac caaggaggcc    300
ctggacaaga tcgaggagga gcagaacaag tcccagcaga agacccagca ggccaaggag    360
gccgacggca aggtgagcca gaactacccc atcgtgcaga acctgcaggg ccagatggtg    420
caccaggcca tcagcccccg caccctgaac gcctgggtga aggtgatcga ggagaaggcc    480
ttcagccccg aggtgatccc catgttcacc gccctgagcg agggcgccac cccccaggac    540
ctgaacacga tgttgaacac cgtgggcggc caccaggccg ccatgcagat gctgaaggac    600
accatcaacg aggaggccgc cgagtgggac cgcctgcacc ccgtgcaggc cggccccgtg    660
gcccccggcc agatgcgcga cccccgcggc agcgacatcg ccggcgccac cagcaccctg    720
caggagcaga tcgcctggat gaccagcaac ccccccgtgc ccgtgggcga catctacaag    780
cggtggatca tcctgggcct gaacaagatc gtgcggatgt acagccccgt gagcatcctg    840
gacatccgcc agggccccaa ggagcccttc cgcgactacg tggaccgctt cttcaagacc    900
ctgcgcgccg agcaggccac ccaggacgtg aagaactgga tgaccgagac cctgctggtg    960
cagaacgcca accccgactg caagaccatc ctgcgcgctc tcggccccgg cgccaccctg   1020
gaggagatga tgaccgcctg ccagggcgtg ggcggccccg gccacaaggc ccgcgtgctg   1080
gccgaggcga tgagccaggc caacagcgtg aacatcatga tgcagaagag caacttcaag   1140
ggcccccggc gcaacgtcaa gtgcttcaac tgcggcaagg agggccacat cgccaagaac   1200
tgccgcgccc cccgcaagaa gggctgctgg aagtgcggca aggagggcca ccagatgaag   1260
gactgcaccg agcgccaggc caacttcctg ggcaagatct ggcccagcca caagggccgc   1320
cccggcaact tcctgcagaa ccgcagcgag cccgccgccc ccaccgtgcc caccgccccc   1380
cccgccgaga gcttccgctt cgaggagacc acccccgccc ccaagcagga gcccaaggac   1440
cgcgagccct accgcgagcc cctgaccgcc ctgcgcagcc tgttcggcag cggccccctg   1500
agccagtaa                                                           1509

<210> SEQ ID NO 5
<211> LENGTH: 141
<212> TYPE: DNA
<213> ORGANISM: Artificial Sequence
<220> FEATURE:
<223> OTHER INFORMATION: Env common region of HIV strain AF110968

<400> SEQUENCE: 5
accatcacca tcacctgccg catcaagcag atcatcaaca tgtggcagaa ggtgggccgc     60
gccatgtacg ccccccccat cgccggcaac ctgacctgcg agagcaacat caccggcctg    120
```

ctgctgaccc gcgacggcgg c 141

<210> SEQ ID NO 6
<211> LENGTH: 1431
<212> TYPE: DNA
<213> ORGANISM: Artificial Sequence
<220> FEATURE:
<223> OTHER INFORMATION: synthetic gp120 coding region of HIV strain AF110968

<400> SEQUENCE: 6
agcgtggtgg gcaacctgtg ggtgaccgtg tactacggcg tgcccgtgtg gaaggaggcc 60
aagaccaccc tgttctgcac cagcgacgcc aaggcctacg agaccgaggt gcacaacgtg 120
tgggccaccc acgcctgcgt gcccaccgac cccaaccccc aggagatcgt gctggagaac 180
gtgaccgaga acttcaacat gtggaagaac gacatggtgg accagatgca cgaggacatc 240
atcagcctgt gggaccagag cctgaagccc tgcgtgaagc tgacccccct gtgcgtgacc 300
ctgaagtgcc gcaacgtgaa cgccaccaac aacatcaaca gcatgatcga caacagcaac 360
aagggcgaga tgaagaactg cagcttcaac gtgaccaccg agctgcgcga ccgcaagcag 420
gaggtgcacg ccctgttcta ccgcctggac gtggtgcccc tgcagggcaa caacagcaac 480
gagtaccgcc tgatcaactg caacaccagc gccatcaccc aggcctgccc caaggtgagc 540
ttcgacccca tccccatcca ctactgcacc cccgccggct acgccatcct gaagtgcaac 600
aaccagacct tcaacggcac cggcccctgc aacaacgtga gcagcgtgca gtgcgcccac 660
ggcatcaagc ccgtggtgag cacccagctg ctgctgaacg gcagcctggc caagggcgag 720
atcatcatcc gcagcgagaa cctggccaac aacgccaaga tcatcatcgt gcagctgaac 780
aagcccgtga agatcgtgtg cgtgcgcccc aacaacaaca cccgcaagag cgtgcgcatc 840
ggccccggcc agaccttcta cgccaccggc gagatcatcg gcgacatccg ccaggcctac 900
tgcatcatca acaagaccga gtggaacagc accctgcagg gcgtgagcaa gaagctggag 960
gagcacttca gcaagaaggc catcaagttc gagcccagca gcggcggcga cctggagatc 1020
accacccaca gcttcaactg ccgcggcgag ttcttctact gcgacaccag ccagctgttc 1080
aacagcacct acagccccag cttcaacggc accgagaaca agctgaacgg caccatcacc 1140
atcacctgcc gcatcaagca gatcatcaac atgtggcaga aggtgggccg cgccatgtac 1200
gcccccccca tcgccggcaa cctgacctgc gagagcaaca tcaccggcct gctgctgacc 1260
cgcgacggcg gcaagaccgg ccccaacgac accgagatct tccgccccgg cggcggcgac 1320
atgcgcgaca actggcgcaa cgagctgtac aagtacaagg tggtggagat caagcccctg 1380
ggcgtggccc ccaccgaggc caagcgccgc gtggtggagc gcgagaagcg c 1431

<210> SEQ ID NO 7
<211> LENGTH: 1944
<212> TYPE: DNA
<213> ORGANISM: Artificial Sequence
<220> FEATURE:
<223> OTHER INFORMATION: synthetic gp140 coding region of HIV strain AF110968

<400> SEQUENCE: 7
agcgtggtgg gcaacctgtg ggtgaccgtg tactacggcg tgcccgtgtg gaaggaggcc 60
aagaccaccc tgttctgcac cagcgacgcc aaggcctacg agaccgaggt gcacaacgtg 120
tgggccaccc acgcctgcgt gcccaccgac cccaaccccc aggagatcgt gctggagaac 180
gtgaccgaga acttcaacat gtggaagaac gacatggtgg accagatgca cgaggacatc 240

```
atcagcctgt gggaccagag cctgaagccc tgcgtgaagc tgacccccct gtgcgtgacc    300

ctgaagtgcc gcaacgtgaa cgccaccaac aacatcaaca gcatgatcga caacagcaac    360

aagggcgaga tgaagaactg cagcttcaac gtgaccaccg agctgcgcga ccgcaagcag    420

gaggtgcacg ccctgttcta ccgcctggac gtggtgcccc tgcagggcaa caacagcaac    480

gagtaccgcc tgatcaactg caacaccagc gccatcaccc aggcctgccc caaggtgagc    540

ttcgacccca tccccatcca ctactgcacc cccgccggct acgccatcct gaagtgcaac    600

aaccagacct tcaacggcac cggcccctgc aacaacgtga gcagcgtgca gtgcgcccac    660

ggcatcaagc ccgtggtgag cacccagctg ctgctgaacg gcagcctggc caagggcgag    720

atcatcatcc gcagcgagaa cctggccaac aacgccaaga tcatcatcgt gcagctgaac    780

aagcccgtga agatcgtgtg cgtgcgcccc aacaacaaca cccgcaagag cgtgcgcatc    840

ggccccggcc agaccttcta cgccaccggc gagatcatcg gcgacatccg ccaggcctac    900

tgcatcatca acaagaccga gtggaacagc accctgcagg gcgtgagcaa gaagctggag    960

gagcacttca gcaagaaggc catcaagttc gagcccagca gcggcggcga cctggagatc   1020

accacccaca gcttcaactg ccgcggcgag ttcttctact gcgacaccag ccagctgttc   1080

aacagcacct acagccccag cttcaacggc accgagaaca agctgaacgg caccatcacc   1140

atcacctgcc gcatcaagca gatcatcaac atgtggcaga aggtgggccg cgccatgtac   1200

gcccccccca tcgccggcaa cctgacctgc gagagcaaca tcaccggcct gctgctgacc   1260

cgcgacggcg gcaagaccgg ccccaacgac accgagatct tccgccccgg cggcggcgac   1320

atgcgcgaca actggcgcaa cgagctgtac aagtacaagg tggtggagat caagcccctg   1380

ggcgtggccc ccaccgaggc caagcgccgc gtggtggagc gcgagaagcg cgccgtgggc   1440

atcggcgccg tgttcctggg cttcctgggc gccgccggca gcaccatggg cgccgccagc   1500

atcaccctga ccgtgcaggc ccgcctgctg ctgagcggca tcgtgcagca gcagaacaac   1560

ctgctgcgcg ccatcgaggc ccagcagcac ctgctgcagc tgaccgtgtg gggcatcaag   1620

cagctgcaga cccgcatcct ggccgtggag cgctacctga aggaccagca gctgctgggc   1680

atctggggct gcagcggcaa gctgatctgc accaccgccg tgccctggaa cagcagctgg   1740

agcaaccgca gccacgacga gatctgggac aacatgacct ggatgcagtg ggaccgcgag   1800

atcaacaact acaccgacac catctaccgc ctgctggagg agagccagaa ccagcaggag   1860

aagaacgaga aggacctgct ggccctggac agctggcaga acctgtggaa ctggttcagc   1920

atcaccaact ggctgtggta catc                                          1944
```

<210> SEQ ID NO 8
<211> LENGTH: 2466
<212> TYPE: DNA
<213> ORGANISM: Artificial Sequence
<220> FEATURE:
<223> OTHER INFORMATION: synthetic gp160 coding region of HIV strain AF110968

<400> SEQUENCE: 8

```
agcgtggtgg gcaacctgtg ggtgaccgtg tactacggcg tgcccgtgtg gaaggaggcc     60

aagaccaccc tgttctgcac cagcgacgcc aaggcctacg agaccgaggt gcacaacgtg    120

tgggccaccc acgcctgcgt gcccaccgac cccaaccccc aggagatcgt gctggagaac    180

gtgaccgaga acttcaacat gtggaagaac gacatggtgg accagatgca cgaggacatc    240

atcagcctgt gggaccagag cctgaagccc tgcgtgaagc tgacccccct gtgcgtgacc    300

ctgaagtgcc gcaacgtgaa cgccaccaac aacatcaaca gcatgatcga caacagcaac    360
```

aagggcgaga tgaagaactg cagcttcaac gtgaccaccg agctgcgcga ccgcaagcag 420
gaggtgcacg ccctgttcta ccgcctggac gtggtgcccc tgcagggcaa caacagcaac 480
gagtaccgcc tgatcaactg caacaccagc gccatcaccc aggcctgccc caaggtgagc 540
ttcgacccca tccccatcca ctactgcacc cccgccggct acgccatcct gaagtgcaac 600
aaccagacct tcaacggcac cggcccctgc aacaacgtga gcagcgtgca gtgcgcccac 660
ggcatcaagc ccgtggtgag cacccagctg ctgctgaacg gcagcctggc caagggcgag 720
atcatcatcc gcagcgagaa cctggccaac aacgccaaga tcatcatcgt gcagctgaac 780
aagcccgtga agatcgtgtg cgtgcgcccc aacaacaaca cccgcaagag cgtgcgcatc 840
ggccccggcc agaccttcta cgccaccggc gagatcatcg gcgacatccg ccaggcctac 900
tgcatcatca acaagaccga gtggaacagc accctgcagg gcgtgagcaa gaagctggag 960
gagcacttca gcaagaaggc catcaagttc gagcccagca gcggcggcga cctggagatc 1020
accacccaca gcttcaactg ccgcggcgag ttcttctact gcgacaccag ccagctgttc 1080
aacagcacct acagccccag cttcaacggc accgagaaca agctgaacgg caccatcacc 1140
atcacctgcc gcatcaagca gatcatcaac atgtggcaga aggtgggccg cgccatgtac 1200
gcccccccca tcgccggcaa cctgacctgc gagagcaaca tcaccggcct gctgctgacc 1260
cgcgacggcg gcaagaccgg ccccaacgac accgagatct tccgccccgg cggcggcgac 1320
atgcgcgaca actggcgcaa cgagctgtac aagtacaagg tggtggagat caagcccctg 1380
ggcgtggccc ccaccgaggc caagcgccgc gtggtggagc gcgagaagcg cgccgtgggc 1440
atcggcgccg tgttcctggg cttcctgggc gccgccggca gcaccatggg cgccgccagc 1500
atcaccctga ccgtgcaggc ccgcctgctg ctgagcggca tcgtgcagca gcagaacaac 1560
ctgctgcgcg ccatcgaggc ccagcagcac ctgctgcagc tgaccgtgtg ggcatcaag 1620
cagctgcaga cccgcatcct ggccgtggag cgctacctga aggaccagca gctgctgggc 1680
atctggggct gcagcggcaa gctgatctgc accaccgccg tgccctggaa cagcagctgg 1740
agcaaccgca gccacgacga gatctgggac aacatgacct ggatgcagtg ggaccgcgag 1800
atcaacaact acaccgacac catctaccgc ctgctggagg agagccagaa ccagcaggag 1860
aagaacgaga aggacctgct ggccctggac agctggcaga acctgtggaa ctggttcagc 1920
atcaccaact ggctgtggta catcaagatc ttcatcatga tcgtgggcgg cctgatcggc 1980
ctgcgcatca tcttcgccgt gctgagcatc gtgaaccgcg tgcgccaggg ctacagcccc 2040
ctgcccttcc agaccctgac ccccaacccc cgcgagcccg accgcctggg ccgcatcgag 2100
gaggagggcg gcgagcagga ccgcggccgc agcatccgcc tggtgagcgg cttcctggcc 2160
ctggcctggg acgacctgcg cagcctgtgc ctgttcagct accaccgcct gcgcgacttc 2220
atcctgatcg ccgcccgcgt gctggagctg ctgggccagc gcggctggga ggccctgaag 2280
tacctgggca gcctggtgca gtactggggc ctggagctga agaagagcgc catcagcctg 2340
ctggacacca tcgccatcgc cgtggccgag ggcaccgacc gcatcatcga gttcatccag 2400
cgcatctgcc gcgccatccg caacatcccc cgccgcatcc gccagggctt cgaggccgcc 2460
ctgcag 2466

<210> SEQ ID NO 9
<211> LENGTH: 2547
<212> TYPE: DNA
<213> ORGANISM: Artificial Sequence
<220> FEATURE:
<223> OTHER INFORMATION: synthetic signal sequence and gp160 coding -continued region of HIV strain AF110968

<400> SEQUENCE: 9
atgcgcgtga tgggcatcct gaagaactac cagcagtggt ggatgtgggg catcctgggc 60
ttctggatgc tgatcatcag cagcgtggtg ggcaacctgt gggtgaccgt gtactacggc 120
gtgcccgtgt ggaaggaggc caagaccacc ctgttctgca ccagcgacgc caaggcctac 180
gagaccgagg tgcacaacgt gtgggccacc cacgcctgcg tgcccaccga ccccaacccc 240
caggagatcg tgctggagaa cgtgaccgag aacttcaaca tgtggaagaa cgacatggtg 300
gaccagatgc acgaggacat catcagcctg tgggaccaga gcctgaagcc ctgcgtgaag 360
ctgacccccc tgtgcgtgac cctgaagtgc cgcaacgtga acgccaccaa caacatcaac 420
agcatgatcg acaacagcaa caagggcgag atgaagaact gcagcttcaa cgtgaccacc 480
gagctgcgcg accgcaagca ggaggtgcac gccctgttct accgcctgga cgtggtgccc 540
ctgcagggca acaacagcaa cgagtaccgc ctgatcaact gcaacaccag cgccatcacc 600
caggcctgcc ccaaggtgag cttcgacccc atccccatcc actactgcac ccccgccggc 660
tacgccatcc tgaagtgcaa caaccagacc ttcaacggca ccggcccctg caacaacgtg 720
agcagcgtgc agtgcgccca cggcatcaag cccgtggtga gcacccagct gctgctgaac 780
ggcagcctgg ccaagggcga gatcatcatc cgcagcgaga acctggccaa caacgccaag 840
atcatcatcg tgcagctgaa caagcccgtg aagatcgtgt gcgtgcgccc caacaacaac 900
acccgcaaga gcgtgcgcat cggccccggc cagaccttct acgccaccgg cgagatcatc 960
ggcgacatcc gccaggccta ctgcatcatc aacaagaccg agtggaacag caccctgcag 1020
ggcgtgagca agaagctgga ggagcacttc agcaagaagg ccatcaagtt cgagcccagc 1080
agcggcggcg acctggagat caccacccac agcttcaact gccgcggcga gttcttctac 1140
tgcgacacca gccagctgtt caacagcacc tacagcccca gcttcaacgg caccgagaac 1200
aagctgaacg gcaccatcac catcacctgc cgcatcaagc agatcatcaa catgtggcag 1260
aaggtgggcc gcgccatgta cgcccccccc atcgccggca acctgacctg cgagagcaac 1320
atcaccggcc tgctgctgac ccgcgacggc ggcaagaccg gccccaacga caccgagatc 1380
ttccgccccg gcggcggcga catgcgcgac aactggcgca acgagctgta caagtacaag 1440
gtggtggaga tcaagcccct gggcgtggcc cccaccgagg ccaagcgccg cgtggtggag 1500
cgcgagaagc gcgccgtggg catcggcgcc gtgttcctgg gcttcctggg cgccgccggc 1560
agcaccatgg gcgccgccag catcaccctg accgtgcagg cccgcctgct gctgagcggc 1620
atcgtgcagc agcagaacaa cctgctgcgc gccatcgagg cccagcagca cctgctgcag 1680
ctgaccgtgt ggggcatcaa gcagctgcag acccgcatcc tggccgtgga gcgctacctg 1740
aaggaccagc agctgctggg catctggggc tgcagcggca agctgatctg caccaccgcc 1800
gtgccctgga acagcagctg gagcaaccgc agccacgacg agatctggga caacatgacc 1860
tggatgcagt gggaccgcga gatcaacaac tacaccgaca ccatctaccg cctgctggag 1920
gagagccaga accagcagga gaagaacgag aaggacctgc tggccctgga cagctggcag 1980
aacctgtgga actggttcag catcaccaac tggctgtggt acatcaagat cttcatcatg 2040
atcgtgggcg gcctgatcgg cctgcgcatc atcttcgccg tgctgagcat cgtgaaccgc 2100
gtgcgccagg gctacagccc cctgcccttc cagaccctga cccccaaccc ccgcgagccc 2160
gaccgcctgg gccgcatcga ggaggagggc ggcgagcagg accgcggccg cagcatccgc 2220
ctggtgagcg gcttcctggc cctggcctgg gacgacctgc gcagcctgtg cctgttcagc 2280

```
taccaccgcc tgcgcgactt catcctgatc gccgcccgcg tgctggagct gctgggccag   2340

cgcggctggg aggccctgaa gtacctgggc agcctggtgc agtactgggg cctggagctg   2400

aagaagagcg ccatcagcct gctggacacc atcgccatcg ccgtggccga gggcaccgac   2460

cgcatcatcg agttcatcca gcgcatctgc cgcgccatcc gcaacatccc ccgccgcatc   2520

cgccagggct tcgaggccgc cctgcag                                       2547
```

<210> SEQ ID NO 10
<211> LENGTH: 1035
<212> TYPE: DNA
<213> ORGANISM: Artificial Sequence
<220> FEATURE:
<223> OTHER INFORMATION: synthetic a gp41 coding region of HIV strain AF110968

<400> SEQUENCE: 10

```
gccgtgggca tcggcgccgt gttcctgggc ttcctgggcg ccgccggcag caccatgggc     60

gccgccagca tcaccctgac cgtgcaggcc cgcctgctgc tgagcggcat cgtgcagcag    120

cagaacaacc tgctgcgcgc catcgaggcc cagcagcacc tgctgcagct gaccgtgtgg    180

ggcatcaagc agctgcagac ccgcatcctg gccgtggagc gctacctgaa ggaccagcag    240

ctgctgggca tctggggctg cagcggcaag ctgatctgca ccaccgccgt gccctggaac    300

agcagctgga gcaaccgcag ccacgacgag atctgggaca acatgacctg gatgcagtgg    360

gaccgcgaga tcaacaacta caccgacacc atctaccgcc tgctggagga gagccagaac    420

cagcaggaga agaacgagaa ggacctgctg gccctggaca gctggcagaa cctgtggaac    480

tggttcagca tcaccaactg gctgtggtac atcaagatct tcatcatgat cgtgggcggc    540

ctgatcggcc tgcgcatcat cttcgccgtg ctgagcatcg tgaaccgcgt gcgccagggc    600

tacagccccc tgcccttcca gaccctgacc cccaaccccc gcgagcccga ccgcctgggc    660

cgcatcgagg aggagggcgg cgagcaggac cgcggccgca gcatccgcct ggtgagcggc    720

ttcctggccc tggcctggga cgacctgcgc agcctgtgcc tgttcagcta ccaccgcctg    780

cgcgacttca tcctgatcgc cgcccgcgtg ctggagctgc tgggccagcg cggctgggag    840

gccctgaagt acctgggcag cctggtgcag tactggggcc tggagctgaa gaagagcgcc    900

atcagcctgc tggacaccat cgccatcgcc gtggccgagg gcaccgaccg catcatcgag    960

ttcatccagc gcatctgccg cgccatccgc aacatccccc gccgcatccg ccagggcttc   1020

gaggccgccc tgcag                                                    1035
```

<210> SEQ ID NO 11
<211> LENGTH: 144
<212> TYPE: DNA
<213> ORGANISM: Artificial Sequence
<220> FEATURE:
<223> OTHER INFORMATION: synthetic Env common region of HIV strain AF110975

<400> SEQUENCE: 11

```
agcatcatca ccctgccctg ccgcatcaag cagatcatcg acatgtggca gaaggtgggc     60

cgcgccatct acgccccccc catcgagggc aacatcacct gcagcagcag catcaccggc    120

ctgctgctgg cccgcgacgg cggc                                           144
```

<210> SEQ ID NO 12
<211> LENGTH: 1437
<212> TYPE: DNA
<213> ORGANISM: Artificial Sequence
<220> FEATURE:

<223> OTHER INFORMATION: synthetic gp120 coding region of HIV strain
AF110975

<400> SEQUENCE: 12
agcggcctgg gcaacctgtg ggtgaccgtg tacgacggcg tgcccgtgtg gcgcgaggcc 60
agcaccaccc tgttctgcgc cagcgacgcc aaggcctacg agaaggaggt gcacaacgtg 120
tgggccaccc acgcctgcgt gcccaccgac cccaaccccc aggagatcga gctggacaac 180
gtgaccgaga acttcaacat gtggaagaac gacatggtgg accagatgca cgaggacatc 240
atcagcctgt gggaccagag cctgaagccc cgcgtgaagc tgacccccct gtgcgtgacc 300
ctgaagtgca ccaactacag caccaactac agcaacacca tgaacgccac cagctacaac 360
aacaacacca ccgaggagat caagaactgc accttcaaca tgaccaccga gctgcgcgac 420
aagaagcagc aggtgtacgc cctgttctac aagctggaca tcgtgcccct gaacagcaac 480
agcagcgagt accgcctgat caactgcaac accagcgcca tcacccaggc ctgccccaag 540
gtgagcttcg accccatccc catccactac tgcgcccccg ccggctacgc catcctgaag 600
tgcaagaaca acaccagcaa cggcaccggc ccctgccaga acgtgagcac cgtgcagtgc 660
acccacggca tcaagcccgt ggtgagcacc cccctgctgc tgaacggcag cctggccgag 720
ggcggcgaga tcatcatccg cagcaagaac ctgagcaaca acgcctacac catcatcgtg 780
cacctgaacg acagcgtgga gatcgtgtgc acccgcccca acaacaacac ccgcaagggc 840
atccgcatcg gccccggcca gaccttctac gccaccgaga acatcatcgg cgacatccgc 900
caggcccact gcaacatcag cgccggcgag tggaacaagg ccgtgcagcg cgtgagcgcc 960
aagctgcgcg agcacttccc caacaagacc atcgagttcc agcccagcag cggcggcgac 1020
ctggagatca ccacccacag cttcaactgc cgcggcgagt tcttctactg caacaccagc 1080
aagctgttca acagcagcta caacggcacc agctaccgcg gcaccgagag caacagcagc 1140
atcatcaccc tgccctgccg catcaagcag atcatcgaca tgtggcagaa ggtgggccgc 1200
gccatctacg cccccccat cgagggcaac atcacctgca gcagcagcat caccggcctg 1260
ctgctggccc gcgacggcgg cctggacaac atcaccaccg agatcttccg cccccagggc 1320
ggcgacatga aggacaactg gcgcaacgag ctgtacaagt acaaggtggt ggagatcaag 1380
cccctgggcg tggcccccac cgaggccaag cgccgcgtgg tggagcgcga gaagcgc 1437

<210> SEQ ID NO 13
<211> LENGTH: 1950
<212> TYPE: DNA
<213> ORGANISM: Artificial Sequence
<220> FEATURE:
<223> OTHER INFORMATION: synthetic gp140 coding region of HIV strain
AF110975

<400> SEQUENCE: 13
agcggcctgg gcaacctgtg ggtgaccgtg tacgacggcg tgcccgtgtg gcgcgaggcc 60
agcaccaccc tgttctgcgc cagcgacgcc aaggcctacg agaaggaggt gcacaacgtg 120
tgggccaccc acgcctgcgt gcccaccgac cccaaccccc aggagatcga gctggacaac 180
gtgaccgaga acttcaacat gtggaagaac gacatggtgg accagatgca cgaggacatc 240
atcagcctgt gggaccagag cctgaagccc cgcgtgaagc tgacccccct gtgcgtgacc 300
ctgaagtgca ccaactacag caccaactac agcaacacca tgaacgccac cagctacaac 360
aacaacacca ccgaggagat caagaactgc accttcaaca tgaccaccga gctgcgcgac 420
aagaagcagc aggtgtacgc cctgttctac aagctggaca tcgtgcccct gaacagcaac 480

```
agcagcgagt accgcctgat caactgcaac accagcgcca tcacccaggc ctgccccaag    540

gtgagcttcg accccatccc catccactac tgcgcccccg ccggctacgc catcctgaag    600

tgcaagaaca acaccagcaa cggcaccggc ccctgccaga acgtgagcac cgtgcagtgc    660

acccacggca tcaagcccgt ggtgagcacc cccctgctgc tgaacggcag cctggccgag    720

ggcggcgaga tcatcatccg cagcaagaac ctgagcaaca acgcctacac catcatcgtg    780

cacctgaacg acagcgtgga gatcgtgtgc acccgcccca acaacaacac ccgcaagggc    840

atccgcatcg gccccggcca gaccttctac gccaccgaga acatcatcgg cgacatccgc    900

caggcccact gcaacatcag cgccggcgag tggaacaagg ccgtgcagcg cgtgagcgcc    960

aagctgcgcg agcacttccc caacaagacc atcgagttcc agcccagcag cggcggcgac   1020

ctggagatca ccacccacag cttcaactgc cgcggcgagt tcttctactg caacaccagc   1080

aagctgttca acagcagcta caacggcacc agctaccgcg gcaccgagag caacagcagc   1140

atcatcaccc tgccctgccg catcaagcag atcatcgaca tgtggcagaa ggtgggccgc   1200

gccatctacg cccccccat cgagggcaac atcacctgca gcagcagcat caccggcctg   1260

ctgctggccc gcgacggcgg cctggacaac atcaccaccg agatcttccg cccccagggc   1320

ggcgacatga aggacaactg gcgcaacgag ctgtacaagt acaaggtggt ggagatcaag   1380

cccctgggcg tggcccccac cgaggccaag cgccgcgtgg tggagcgcga gaagcgcgcc   1440

gtgggcatcg gcgccgtgat cttcggcttc ctgggcgccg ccggcagcaa catgggcgcc   1500

gccagcatca ccctgaccgc ccaggcccgc cagctgctga gcggcatcgt gcagcagcag   1560

agcaacctgc tgcgcgccat cgaggcccag cagcacatgc tgcagctgac cgtgtggggc   1620

atcaagcagc tgcaggcccg cgtgctggcc atcgagcgct acctgaagga ccagcagctg   1680

ctgggcatct ggggctgcag cggcaagctg atctgcacca ccaccgtgcc ctggaacagc   1740

agctggagca acaagaccca gggcgagatc tgggagaaca tgacctggat gcagtgggac   1800

aaggagatca gcaactacac cggcatcatc taccgcctgc tggaggagag ccagaaccag   1860

caggagcaga acgagaagga cctgctggcc ctggacagcc gcaacaacct gtggagctgg   1920

ttcaacatca gcaactggct gtggtacatc                                    1950


<210> SEQ ID NO 14
<211> LENGTH: 2493
<212> TYPE: DNA
<213> ORGANISM: Artificial Sequence
<220> FEATURE:
<223> OTHER INFORMATION: synthetic gp160 coding region of HIV strain
      AF110975

<400> SEQUENCE: 14

agcggcctgg gcaacctgtg ggtgaccgtg tacgacggcg tgcccgtgtg gcgcgaggcc     60

agcaccaccc tgttctgcgc cagcgacgcc aaggcctacg agaaggaggt gcacaacgtg    120

tgggccaccc acgcctgcgt gcccaccgac cccaaccccc aggagatcga gctggacaac    180

gtgaccgaga acttcaacat gtggaagaac gacatggtgg accagatgca cgaggacatc    240

atcagcctgt gggaccagag cctgaagccc cgcgtgaagc tgacccccct gtgcgtgacc    300

ctgaagtgca ccaactacag caccaactac agcaacacca tgaacgccac cagctacaac    360

aacaacacca ccgaggagat caagaactgc accttcaaca tgaccaccga gctgcgcgac    420

aagaagcagc aggtgtacgc cctgttctac aagctggaca tcgtgcccct gaacagcaac    480

agcagcgagt accgcctgat caactgcaac accagcgcca tcacccaggc ctgccccaag    540

gtgagcttcg accccatccc catccactac tgcgcccccg ccggctacgc catcctgaag    600
```

tgcaagaaca acaccagcaa cggcaccggc ccctgccaga acgtgagcac cgtgcagtgc 660
acccacggca tcaagcccgt ggtgagcacc cccctgctgc tgaacggcag cctggccgag 720
ggcggcgaga tcatcatccg cagcaagaac ctgagcaaca acgcctacac catcatcgtg 780
cacctgaacg acagcgtgga gatcgtgtgc acccgcccca acaacaacac ccgcaagggc 840
atccgcatcg gccccggcca gaccttctac gccaccgaga acatcatcgg cgacatccgc 900
caggcccact gcaacatcag cgccggcgag tggaacaagg ccgtgcagcg cgtgagcgcc 960
aagctgcgcg agcacttccc caacaagacc atcgagttcc agcccagcag cggcggcgac 1020
ctggagatca ccacccacag cttcaactgc cgcggcgagt tcttctactg caacaccagc 1080
aagctgttca acagcagcta caacggcacc agctaccgcg gcaccgagag caacagcagc 1140
atcatcaccc tgccctgccg catcaagcag atcatcgaca tgtggcagaa ggtgggccgc 1200
gccatctacg cccccccccat cgagggcaac atcacctgca gcagcagcat caccggcctg 1260
ctgctggccc gcgacggcgg cctggacaac atcaccaccg agatcttccg cccccagggc 1320
ggcgacatga aggacaactg gcgcaacgag ctgtacaagt acaaggtggt ggagatcaag 1380
cccctgggcg tggcccccac cgaggccaag cgccgcgtgg tggagcgcga gaagcgcgcc 1440
gtgggcatcg gcgccgtgat cttcggcttc ctgggcgccg ccggcagcaa catgggcgcc 1500
gccagcatca ccctgaccgc ccaggcccgc cagctgctga gcggcatcgt gcagcagcag 1560
agcaacctgc tgcgcgccat cgaggcccag cagcacatgc tgcagctgac cgtgtggggc 1620
atcaagcagc tgcaggcccg cgtgctggcc atcgagcgct acctgaagga ccagcagctg 1680
ctgggcatct ggggctgcag cggcaagctg atctgcacca ccaccgtgcc ctggaacagc 1740
agctggagca acaagaccca gggcgagatc tgggagaaca tgacctggat gcagtgggac 1800
aaggagatca gcaactacac cggcatcatc taccgcctgc tggaggagag ccagaaccag 1860
caggagcaga acgagaagga cctgctggcc ctggacagcc gcaacaacct gtggagctgg 1920
ttcaacatca gcaactggct gtggtacatc aagatcttca tcatgatcgt gggcggcctg 1980
atcggcctgc gcatcatctt cgccgtgctg agcatcgtga accgcgtgcg ccagggctac 2040 agcccccctga gcttccagac cctgaccccc aacccccgcg gcctggaccg cctgggccgc 2100
atcgaggagg agggcggcga gcaggaccgc gaccgcagca tccgcctggt gcagggcttc 2160
ctggccctgg cctgggacga cctgcgcagc ctgtgcctgt tcagctacca ccgcctgcgc 2220
gacctgatcc tggtgaccgc ccgcgtggtg gagctgctgg gccgcagcag cccccgcggc 2280
ctgcagcgcg gctgggaggc cctgaagtac ctgggcagcc tggtgcagta ctggggcctg 2340
gagctgaaga agagcgccac cagcctgctg gacagcatcg ccatcgccgt ggccgagggc 2400
accgaccgca tcatcgaggt gatccagcgc atctaccgcg ccttctgcaa catcccccgc 2460
cgcgtgcgcc agggcttcga ggccgccctg cag 2493

<210> SEQ ID NO 15
<211> LENGTH: 2565
<212> TYPE: DNA
<213> ORGANISM: Artificial Sequence
<220> FEATURE:
<223> OTHER INFORMATION: synthetic signal sequence and gp160 coding region of HIV strain AF110975

<400> SEQUENCE: 15
atgcgcgtgc gcggcatcct gcgcagctgg cagcagtggt ggatctgggg catcctgggc 60
ttctggatct gcagcggcct gggcaacctg tgggtgaccg tgtacgacgg cgtgcccgtg 120

-continued

```
tggcgcgagg ccagcaccac cctgttctgc gccagcgacg ccaaggccta cgagaaggag    180
gtgcacaacg tgtgggccac ccacgcctgc gtgcccaccg accccaaccc ccaggagatc    240
gagctggaca acgtgaccga gaacttcaac atgtggaaga acgacatggt ggaccagatg    300
cacgaggaca tcatcagcct gtgggaccag agcctgaagc cccgcgtgaa gctgaccccc    360
ctgtgcgtga ccctgaagtg caccaactac agcaccaact acagcaacac catgaacgcc    420
accagctaca acaacaacac caccgaggag atcaagaact gcaccttcaa catgaccacc    480
gagctgcgcg acaagaagca gcaggtgtac gccctgttct acaagctgga catcgtgccc    540
ctgaacagca acagcagcga gtaccgcctg atcaactgca acaccagcgc catcacccag    600
gcctgcccca aggtgagctt cgaccccatc cccatccact actgcgcccc cgccggctac    660
gccatcctga agtgcaagaa caacaccagc aacggcaccg gcccctgcca gaacgtgagc    720
accgtgcagt gcacccacgg catcaagccc gtggtgagca ccccccctgct gctgaacggc    780
agcctggccg agggcggcga gatcatcatc cgcagcaaga acctgagcaa caacgcctac    840
accatcatcg tgcacctgaa cgacagcgtg gagatcgtgt gcacccgccc caacaacaac    900
acccgcaagg gcatccgcat cggccccggc cagaccttct acgccaccga gaacatcatc    960
ggcgacatcc gccaggccca ctgcaacatc agcgccggcg agtggaacaa ggccgtgcag   1020
cgcgtgagcg ccaagctgcg cgagcacttc cccaacaaga ccatcgagtt ccagcccagc   1080
agcggcggcg acctggagat caccacccac agcttcaact gccgcggcga gttcttctac   1140
tgcaacacca gcaagctgtt caacagcagc tacaacggca ccagctaccg cggcaccgag   1200
agcaacagca gcatcatcac cctgccctgc cgcatcaagc agatcatcga catgtggcag   1260
aaggtgggcc gcgccatcta cgcccccccc atcgagggca acatcacctg cagcagcagc   1320
atcaccggcc tgctgctggc ccgcgacggc ggcctggaca acatcaccac cgagatcttc   1380
cgcccccagg gcggcgacat gaaggacaac tggcgcaacg agctgtacaa gtacaaggtg   1440
gtggagatca agcccctggg cgtggccccc accgaggcca agcgccgcgt ggtggagcgc   1500
gagaagcgcg ccgtgggcat cggcgccgtg atcttcggct tcctgggcgc cgccggcagc   1560
aacatgggcg ccgccagcat caccctgacc gcccaggccc gccagctgct gagcggcatc   1620
gtgcagcagc agagcaacct gctgcgcgcc atcgaggccc agcagcacat gctgcagctg   1680
accgtgtggg gcatcaagca gctgcaggcc cgcgtgctgg ccatcgagcg ctacctgaag   1740
gaccagcagc tgctgggcat ctggggctgc agcggcaagc tgatctgcac caccaccgtg   1800
ccctggaaca gcagctggag caacaagacc cagggcgaga tctgggagaa catgacctgg   1860
atgcagtggg acaaggagat cagcaactac accggcatca tctaccgcct gctggaggag   1920
agccagaacc agcaggagca gaacgagaag gacctgctgg ccctggacag ccgcaacaac   1980
ctgtggagct ggttcaacat cagcaactgg ctgtggtaca tcaagatctt catcatgatc   2040
gtgggcggcc tgatcggcct gcgcatcatc ttcgccgtgc tgagcatcgt gaaccgcgtg   2100
cgccagggct acagcccccct gagcttccag accctgaccc ccaaccccccg cggcctggac   2160
cgcctgggcc gcatcgagga ggagggcggc gagcaggacc gcgaccgcag catccgcctg   2220
gtgcagggct tcctggccct ggcctgggac gacctgcgca gcctgtgcct gttcagctac   2280
caccgcctgc gcgacctgat cctggtgacc gcccgcgtgg tggagctgct gggccgcagc   2340
agcccccgcg gcctgcagcg cggctgggag gccctgaagt acctgggcag cctggtgcag   2400
tactggggcc tggagctgaa gaagagcgcc accagcctgc tggacagcat cgccatcgcc   2460
gtggccgagg gcaccgaccg catcatcgag gtgatccagc gcatctaccg cgccttctgc   2520
```

aacatccccc gccgcgtgcg ccagggcttc gaggccgccc tgcag 2565

<210> SEQ ID NO 16
<211> LENGTH: 1056
<212> TYPE: DNA
<213> ORGANISM: Artificial Sequence
<220> FEATURE:
<223> OTHER INFORMATION: synthetic a gp41 coding region of HIV strain AF110975

<400> SEQUENCE: 16
gccgtgggca tcggcgccgt gatcttcggc ttcctgggcg ccgccggcag caacatgggc 60
gccgccagca tcaccctgac cgcccaggcc cgccagctgc tgagcggcat cgtgcagcag 120
cagagcaacc tgctgcgcgc catcgaggcc cagcagcaca tgctgcagct gaccgtgtgg 180
ggcatcaagc agctgcaggc ccgcgtgctg gccatcgagc gctacctgaa ggaccagcag 240
ctgctgggca tctggggctg cagcggcaag ctgatctgca ccaccaccgt gccctggaac 300
agcagctgga gcaacaagac ccagggcgag atctgggaga acatgacctg gatgcagtgg 360
gacaaggaga tcagcaacta caccggcatc atctaccgcc tgctggagga gagccagaac 420
cagcaggagc agaacgagaa ggacctgctg gccctggaca gccgcaacaa cctgtggagc 480
tggttcaaca tcagcaactg gctgtggtac atcaagatct tcatcatgat cgtgggcggc 540
ctgatcggcc tgcgcatcat cttcgccgtg ctgagcatcg tgaaccgcgt gcgccagggc 600
tacagccccc tgagcttcca gaccctgacc cccaaccccc gcggcctgga ccgcctgggc 660
cgcatcgagg aggagggcgg cgagcaggac cgcgaccgca gcatccgcct ggtgcagggc 720
ttcctggccc tggcctggga cgacctgcgc agcctgtgcc tgttcagcta ccaccgcctg 780
cgcgacctga tcctggtgac cgcccgcgtg gtggagctgc tgggccgcag cagcccccgc 840
ggcctgcagc gcggctggga ggccctgaag tacctgggca gcctggtgca gtactggggc 900
ctggagctga agaagagcgc caccagcctg ctggacagca tcgccatcgc cgtggccgag 960
ggcaccgacc gcatcatcga ggtgatccag cgcatctacc gcgccttctg caacatcccc 1020
cgccgcgtgc gccagggctt cgaggccgcc ctgcag 1056

<210> SEQ ID NO 17
<211> LENGTH: 492
<212> TYPE: PRT
<213> ORGANISM: Human immunodeficiency virus

<400> SEQUENCE: 17

Met Gly Ala Arg Ala Ser Ile Leu Arg Gly Gly Lys Leu Asp Ala Trp
1 5 10 15

Glu Arg Ile Arg Leu Arg Pro Gly Gly Lys Lys Cys Tyr Met Met Lys
20 25 30

His Leu Val Trp Ala Ser Arg Glu Leu Glu Lys Phe Ala Leu Asn Pro
35 40 45

Gly Leu Leu Glu Thr Ser Glu Gly Cys Lys Gln Ile Ile Arg Gln Leu
50 55 60

His Pro Ala Leu Gln Thr Gly Ser Glu Glu Leu Lys Ser Leu Phe Asn
65 70 75 80

Thr Val Ala Thr Leu Tyr Cys Val His Glu Lys Ile Glu Val Arg Asp
85 90 95

Thr Lys Glu Ala Leu Asp Lys Ile Glu Glu Glu Gln Asn Lys Cys Gln
100 105 110

Gln Lys Ile Gln Gln Ala Glu Ala Ala Asp Lys Gly Lys Val Ser Gln
115 120 125

```
Asn Tyr Pro Ile Val Gln Asn Leu Gln Gly Gln Met Val His Gln Ala
    130                 135                 140

Ile Ser Pro Arg Thr Leu Asn Ala Trp Val Lys Val Ile Glu Glu Lys
145                 150                 155                 160

Ala Phe Ser Pro Glu Val Ile Pro Met Phe Thr Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Asp Thr Ile Asn Glu Glu Ala Ala
        195                 200                 205

Glu Trp Asp Arg Val His Pro Val His Ala Gly Pro Ile Ala Pro Gly
    210                 215                 220

Gln Met Arg Glu Pro Arg Gly Ser Asp Ile Ala Gly Thr Thr Ser Thr
225                 230                 235                 240

Leu Gln Glu Gln Ile Ala Trp Met Thr Ser Asn Pro Pro Ile Pro Val
                245                 250                 255

Gly Asp Ile Tyr Lys Arg Trp Ile Ile Leu Gly Leu Asn Lys Ile Val
            260                 265                 270

Arg Met Tyr Ser Pro Val Ser Ile Leu Asp Ile Lys Gln Gly Pro Lys
        275                 280                 285

Glu Pro Phe Arg Asp Tyr Val Asp Arg Phe Phe Lys Thr Leu Arg Ala
    290                 295                 300

Glu Gln Ser Thr Gln Glu Val Lys Asn Trp Met Thr Asp Thr Leu Leu
305                 310                 315                 320

Val Gln Asn Ala Asn Pro Asp Cys Lys Thr Ile Leu Arg Ala Leu Gly
                325                 330                 335

Pro Gly Ala Ser Leu Glu Glu Met Met Thr Ala Cys Gln Gly Val Gly
            340                 345                 350

Gly Pro Ser His Lys Ala Arg Val Leu Ala Glu Ala Met Ser Gln Ala
        355                 360                 365

Asn Thr Ser Val Met Met Gln Lys Ser Asn Phe Lys Gly Pro Arg Arg
    370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Ser Arg
        435                 440                 445

Pro Glu Pro Thr Ala Pro Pro Ala Glu Ser Phe Arg Phe Glu Glu Thr
    450                 455                 460

Thr Pro Gly Gln Lys Gln Glu Ser Lys Asp Arg Glu Thr Leu Thr Ser
465                 470                 475                 480

Leu Lys Ser Leu Phe Gly Asn Asp Pro Leu Ser Gln
                485                 490
```

<210> SEQ ID NO 18
<211> LENGTH: 81
<212> TYPE: DNA
<213> ORGANISM: Artificial Sequence
<220> FEATURE:
<223> OTHER INFORMATION: synthetic signal sequence of HIV strain AF110968

<400> SEQUENCE: 18
atgcgcgtga tgggcatcct gaagaactac cagcagtggt ggatgtgggg catcctgggc 60
ttctggatgc tgatcatcag c 81

<210> SEQ ID NO 19
<211> LENGTH: 72
<212> TYPE: DNA
<213> ORGANISM: Artificial Sequence
<220> FEATURE:
<223> OTHER INFORMATION: synthetic signal sequence of HIV strain AF110975

<400> SEQUENCE: 19
atgcgcgtgc gcggcatcct gcgcagctgg cagcagtggt ggatctgggg catcctgggc 60
ttctggatct gc 72

<210> SEQ ID NO 20
<211> LENGTH: 1479
<212> TYPE: DNA
<213> ORGANISM: Artificial Sequence
<220> FEATURE:
<223> OTHER INFORMATION: synthetic Gag coding sequence of HIV strain AF110965

<400> SEQUENCE: 20
atgggcgccc gcgccagcat cctgcgcggc ggcaagctgg acgcctggga gcgcatccgc 60
ctgcgccccg gcggcaagaa gtgctacatg atgaagcacc tggtgtgggc cagccgcgag 120
ctggagaagt tcgccctgaa ccccggcctg ctggagacca gcgagggctg caagcagatc 180
atccgccagc tgcaccccgc cctgcagacc ggcagcgagg agctgaagag cctgttcaac 240
accgtggcca ccctgtactg cgtgcacgag aagatcgagg tgcgcgacac caaggaggcc 300
ctggacaaga tcgaggagga gcagaacaag tgccagcaga agatccagca ggccgaggcc 360
gccgacaagg gcaaggtgag ccagaactac cccatcgtgc agaacctgca gggccagatg 420
gtgcaccagg ccatcagccc ccgcaccctg aacgcctggg tgaaggtgat cgaggagaag 480
gccttcagcc ccgaggtgat ccccatgttc accgccctga gcgagggcgc caccccccag 540
gacctgaaca ccatgctgaa caccgtgggc ggccaccagg ccgccatgca gatgctgaag 600
gacaccatca acgaggaggc cgccgagtgg gaccgcgtgc accccgtgca cgccggcccc 660
atcgcccccg gccagatgcg cgagccccgc ggcagcgaca tcgccggcac caccagcacc 720
ctgcaggagc agatcgcctg gatgaccagc aacccccca tccccgtggg cgacatctac 780
aagcgctgga tcatcctggg cctgaacaag atcgtgcgca tgtacagccc cgtgagcatc 840
ctggacatca agcagggccc caaggagccc ttccgcgact acgtggaccg cttcttcaag 900
accctgcgcg ccgagcagag cacccaggag gtgaagaact ggatgaccga caccctgctg 960
gtgcagaacg ccaaccccga ctgcaagacc atcctgcgcg ccctgggccc cggcgccagc 1020
ctggaggaga tgatgaccgc ctgccagggc gtgggcggcc ccagccacaa ggcccgcgtg 1080
ctggccgagg ccatgagcca ggccaacacc agcgtgatga tgcagaagag caacttcaag 1140
ggcccccgcc gcatcgtgaa gtgcttcaac tgcggcaagg agggccacat cgcccgcaac 1200
tgccgcgccc cccgcaagaa gggctgctgg aagtgcggca aggagggcca ccagatgaag 1260
gactgcaccg agcgccaggc caacttcctg ggcaagatct ggcccagcca caagggccgc 1320
cccggcaact tcctgcagag ccgccccgag cccaccgccc cccccgccga gagcttccgc 1380
ttcgaggaga ccacccccgg ccagaagcag gagagcaagg accgcgagac cctgaccagc 1440
ctgaagagcc tgttcggcaa cgacccccctg agccagtaa 1479

<210> SEQ ID NO 21
<211> LENGTH: 1509
<212> TYPE: DNA
<213> ORGANISM: Artificial Sequence
<220> FEATURE:
<223> OTHER INFORMATION: synthetic Gag coding sequence of HIV strain AF110967

<400> SEQUENCE: 21

```
atgggcgccc gcgccagcat cctgcgcggc gagaagctgg acaagtggga gaagatccgc      60
ctgcgccccg gcggcaagaa gcactacatg ctgaagcacc tggtgtgggc cagccgcgag     120
ctggagggct tcgccctgaa ccccggcctg ctggagaccg ccgagggctg caagcagatc     180
atgaagcagc tgcagcccgc cctgcagacc ggcaccgagg agctgcgcag cctgtacaac     240
accgtggcca ccctgtactg cgtgcacgcc ggcatcgagg tgcgcgacac caaggaggcc     300
ctggacaaga tcgaggagga gcagaacaag agccagcaga agacccagca ggccaaggag     360
gccgacggca aggtgagcca gaactacccc atcgtgcaga acctgcaggg ccagatggtg     420
caccaggcca tcagcccccg caccctgaac gcctgggtga aggtgatcga ggagaaggcc     480
ttcagccccg aggtgatccc catgttcacc gccctgagcg agggcgccac cccccaggac     540
ctgaacacca tgctgaacac cgtgggcggc caccaggccg ccatgcagat gctgaaggac     600
accatcaacg aggaggccgc cgagtgggac cgcctgcacc ccgtgcaggc cggccccgtg     660
gcccccggcc agatgcgcga cccccgcggc agcgacatcg ccggcgccac cagcaccctg     720
caggagcaga tcgcctggat gaccagcaac ccccccgtgc ccgtgggcga catctacaag     780
cgctggatca tcctgggcct gaacaagatc gtgcgcatgt acagccccgt gagcatcctg     840
gacatccgcc agggccccaa ggagcccttc cgcgactacg tggaccgctt cttcaagacc     900
ctgcgcgccg agcaggccac ccaggacgtg aagaactgga tgaccgagac cctgctggtg     960
cagaacgcca accccgactg caagaccatc ctgcgcgccc tgggccccgg cgccaccctg    1020
gaggagatga tgaccgcctg ccagggcgtg ggcggccccg gccacaaggc ccgcgtgctg    1080
gccgaggcca tgagccaggc caacagcgtg aacatcatga tgcagaagag caacttcaag    1140
ggcccccgcc gcaacgtgaa gtgcttcaac tgcggcaagg agggccacat cgccaagaac    1200
tgccgcgccc cccgcaagaa gggctgctgg aagtgcggca aggagggcca ccagatgaag    1260
gactgcaccg agcgccaggc caacttcctg ggcaagatct ggcccagcca caagggccgc    1320
cccggcaact tcctgcagaa ccgcagcgag cccgccgccc ccaccgtgcc caccgccccc    1380
cccgccgaga gcttccgctt cgaggagacc acccccgccc ccaagcagga gcccaaggac    1440
cgcgagccct accgcgagcc cctgaccgcc ctgcgcagcc tgttcggcag cggcccccctg   1500
agccagtaa                                                           1509
```

<210> SEQ ID NO 22
<211> LENGTH: 502
<212> TYPE: PRT
<213> ORGANISM: Human immunodeficiency virus

<400> SEQUENCE: 22

```
Met Gly Ala Arg Ala Ser Ile Leu Arg Gly Glu Lys Leu Asp Lys Trp
 1               5                  10                  15

Glu Lys Ile Arg Leu Arg Pro Gly Gly Lys Lys His Tyr Met Leu Lys
            20                  25                  30

His Leu Val Trp Ala Ser Arg Glu Leu Glu Gly Phe Ala Leu Asn Pro
        35                  40                  45
```

```
Gly Leu Leu Glu Thr Ala Glu Gly Cys Lys Gln Ile Met Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val Gln Ala Gly Pro Val Ala Pro Gly Gln
    210                 215                 220

Met Arg Asp Pro Arg Gly Ser Asp Ile Ala Gly Ala Thr Ser Thr Leu
225                 230                 235                 240

Gln Glu Gln Ile Ala Trp Met Thr Ser Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Glu Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365

Ser Val Asn Ile Met Met Gln Lys Ser Asn Phe Lys Gly Pro Arg Arg
    370                 375                 380

Asn Val Lys Cys Phe Asn Cys Gly Lys Glu Gly His Ile Ala Lys Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
        435                 440                 445

Ser Glu Pro Ala Ala Pro Thr Val Pro Thr Ala Pro Pro Ala Glu Ser
    450                 455                 460

Phe Arg Phe Glu Glu Thr Thr Pro Ala Pro Lys Gln Glu Pro Lys Asp
```

```
465                 470                 475                 480

Arg Glu Pro Tyr Arg Glu Pro Leu Thr Ala Leu Arg Ser Leu Phe Gly
                485                 490                 495

Ser Gly Pro Leu Ser Gln
            500


<210> SEQ ID NO 23
<211> LENGTH: 849
<212> TYPE: PRT
<213> ORGANISM: Human immunodeficiency virus

<400> SEQUENCE: 23

Met Arg Val Met Gly Ile Leu Lys Asn Tyr Gln Gln Trp Trp Met Trp
 1               5                  10                  15

Gly Ile Leu Gly Phe Trp Met Leu Ile Ile Ser Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Thr Ser Asp Ala Lys Ala Tyr Glu Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Lys Cys Arg Asn Val Asn Ala Thr Asn Asn Ile Asn Ser Met Ile Asp
    130                 135                 140

Asn Ser Asn Lys Gly Glu Met Lys Asn Cys Ser Phe Asn Val Thr Thr
145                 150                 155                 160

Glu Leu Arg Asp Arg Lys Gln Glu Val His Ala Leu Phe Tyr Arg Leu
                165                 170                 175

Asp Val Val Pro Leu Gln Gly Asn Asn Ser Asn Glu Tyr Arg Leu Ile
            180                 185                 190

Asn Cys Asn Thr Ser Ala Ile Thr Gln Ala Cys Pro Lys Val Ser Phe
        195                 200                 205

Asp Pro Ile Pro Ile His Tyr Cys Thr Pro Ala Gly Tyr Ala Ile Leu
    210                 215                 220

Lys Cys Asn Asn Gln Thr Phe Asn Gly Thr Gly Pro Cys Asn Asn Val
225                 230                 235                 240

Ser Ser Val Gln Cys Ala His Gly Ile Lys Pro Val Val Ser Thr Gln
                245                 250                 255

Leu Leu Leu Asn Gly Ser Leu Ala Lys Gly Glu Ile Ile Ile Arg Ser
            260                 265                 270

Glu Asn Leu Ala Asn Asn Ala Lys Ile Ile Ile Val Gln Leu Asn Lys
        275                 280                 285

Pro Val Lys Ile Val Cys Val Arg Pro Asn Asn Asn Thr Arg Lys Ser
    290                 295                 300

Val Arg Ile Gly Pro Gly Gln Thr Phe Tyr Ala Thr Gly Glu Ile Ile
305                 310                 315                 320

Gly Asp Ile Arg Gln Ala Tyr Cys Ile Ile Asn Lys Thr Glu Trp Asn
                325                 330                 335

Ser Thr Leu Gln Gly Val Ser Lys Lys Leu Glu Glu His Phe Ser Lys
```

```
            340                 345                 350

Lys Ala Ile Lys Phe Glu Pro Ser Ser Gly Gly Asp Leu Glu Ile Thr
        355                 360                 365

Thr His Ser Phe Asn Cys Arg Gly Glu Phe Phe Tyr Cys Asp Thr Ser
    370                 375                 380

Gln Leu Phe Asn Ser Thr Tyr Ser Pro Ser Phe Asn Gly Thr Glu Asn
385                 390                 395                 400

Lys Leu Asn Gly Thr Ile Thr Ile Thr Cys Arg Ile Lys Gln Ile Ile
                405                 410                 415

Asn Met Trp Gln Lys Val Gly Arg Ala Met Tyr Ala Pro Pro Ile Ala
            420                 425                 430

Gly Asn Leu Thr Cys Glu Ser Asn Ile Thr Gly Leu Leu Leu Thr Arg
        435                 440                 445

Asp Gly Gly Lys Thr Gly Pro Asn Asp Thr Glu Ile Phe Arg Pro Gly
    450                 455                 460

Gly Gly Asp Met Arg Asp Asn Trp Arg Asn Glu Leu Tyr Lys Tyr Lys
465                 470                 475                 480

Val Val Glu Ile Lys Pro Leu Gly Val Ala Pro Thr Glu Ala Lys Arg
                485                 490                 495

Arg Val Val Glu Arg Glu Lys Arg Ala Val Gly Ile Gly Ala Val Phe
            500                 505                 510

Leu Gly Phe Leu Gly Ala Ala Gly Ser Thr Met Gly Ala Ala Ser Ile
        515                 520                 525

Thr Leu Thr Val Gln Ala Arg Leu Leu Leu Ser Gly Ile Val Gln Gln
    530                 535                 540

Gln Asn Asn Leu Leu Arg Ala Ile Glu Ala Gln Gln His Leu Leu Gln
545                 550                 555                 560

Leu Thr Val Trp Gly Ile Lys Gln Leu Gln Thr Arg Ile Leu Ala Val
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Ala Val Pro Trp Asn Ser Ser Trp Ser
        595                 600                 605

Asn Arg Ser His Asp Glu Ile Trp Asp Asn Met Thr Trp Met Gln Trp
    610                 615                 620

Asp Arg Glu Ile Asn Asn Tyr Thr Asp Thr Ile Tyr Arg Leu Leu Glu
625                 630                 635                 640

Glu Ser Gln Asn Gln Gln Glu Lys Asn Glu Lys Asp Leu Leu Ala Leu
                645                 650                 655

Asp Ser Trp Gln Asn Leu Trp Asn Trp Phe Ser Ile Thr Asn Trp Leu
            660                 665                 670

Trp Tyr Ile Lys Ile Phe Ile Met Ile Val Gly Gly Leu Ile Gly Leu
        675                 680                 685

Arg Ile Ile Phe Ala Val Leu Ser Ile Val Asn Arg Val Arg Gln Gly
    690                 695                 700

Tyr Ser Pro Leu Pro Phe Gln Thr Leu Thr Pro Asn Pro Arg Glu Pro
705                 710                 715                 720

Asp Arg Leu Gly Arg Ile Glu Glu Glu Gly Gly Glu Gln Asp Arg Gly
                725                 730                 735

Arg Ser Ile Arg Leu Val Ser Gly Phe Leu Ala Leu Ala Trp Asp Asp
            740                 745                 750

Leu Arg Ser Leu Cys Leu Phe Ser Tyr His Arg Leu Arg Asp Phe Ile
        755                 760                 765
```

```
Leu Ile Ala Ala Arg Val Leu Glu Leu Leu Gly Gln Arg Gly Trp Glu
    770                 775                 780

Ala Leu Lys Tyr Leu Gly Ser Leu Val Gln Tyr Trp Gly Leu Glu Leu
785                 790                 795                 800

Lys Lys Ser Ala Ile Ser Leu Leu Asp Thr Ile Ala Ile Ala Val Ala
                805                 810                 815

Glu Gly Thr Asp Arg Ile Ile Glu Phe Ile Gln Arg Ile Cys Arg Ala
            820                 825                 830

Ile Arg Asn Ile Pro Arg Arg Ile Arg Gln Gly Phe Glu Ala Ala Leu
        835                 840                 845

Gln


<210> SEQ ID NO 24
<211> LENGTH: 855
<212> TYPE: PRT
<213> ORGANISM: Human immunodeficiency virus

<400> SEQUENCE: 24

Met Arg Val Arg Gly Ile Leu Arg Ser Trp Gln Gln Trp Trp Ile Trp
 1               5                  10                  15

Gly Ile Leu Gly Phe Trp Ile Cys Ser Gly Leu Gly Asn Leu Trp Val
            20                  25                  30

Thr Val Tyr Asp Gly Val Pro Val Trp Arg Glu Ala Ser Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Ile
65                  70                  75                  80

Glu Leu Asp Asn Val Thr Glu Asn Phe Asn Met Trp Lys Asn Asp Met
                85                  90                  95

Val Asp Gln Met His Glu Asp Ile Ile Ser Leu Trp Asp Gln Ser Leu
            100                 105                 110

Lys Pro Arg Val Lys Leu Thr Pro Leu Cys Val Thr Leu Lys Cys Thr
        115                 120                 125

Asn Tyr Ser Thr Asn Tyr Ser Asn Thr Met Asn Ala Thr Ser Tyr Asn
    130                 135                 140

Asn Asn Thr Thr Glu Glu Ile Lys Asn Cys Thr Phe Asn Met Thr Thr
145                 150                 155                 160

Glu Leu Arg Asp Lys Lys Gln Gln Val Tyr Ala Leu Phe Tyr Lys Leu
                165                 170                 175

Asp Ile Val Pro Leu Asn Ser Asn Ser Ser Glu Tyr Arg Leu Ile Asn
            180                 185                 190

Cys Asn Thr Ser Ala Ile Thr Gln Ala Cys Pro Lys Val Ser Phe Asp
        195                 200                 205

Pro Ile Pro Ile His Tyr Cys Ala Pro Ala Gly Tyr Ala Ile Leu Lys
    210                 215                 220

Cys Lys Asn Asn Thr Ser Asn Gly Thr Gly Pro Cys Gln Asn Val Ser
225                 230                 235                 240

Thr Val Gln Cys Thr His Gly Ile Lys Pro Val Val Ser Thr Pro Leu
                245                 250                 255

Leu Leu Asn Gly Ser Leu Ala Glu Gly Gly Glu Ile Ile Ile Arg Ser
            260                 265                 270

Lys Asn Leu Ser Asn Asn Ala Tyr Thr Ile Ile Val His Leu Asn Asp
        275                 280                 285

Ser Val Glu Ile Val Cys Thr Arg Pro Asn Asn Asn Thr Arg Lys Gly
```

-continued

```
    290                 295                 300

Ile Arg Ile Gly Pro Gly Gln Thr Phe Tyr Ala Thr Glu Asn Ile Ile
305                 310                 315                 320

Gly Asp Ile Arg Gln Ala His Cys Asn Ile Ser Ala Gly Glu Trp Asn
                325                 330                 335

Lys Ala Val Gln Arg Val Ser Ala Lys Leu Arg Glu His Phe Pro Asn
            340                 345                 350

Lys Thr Ile Glu Phe Gln Pro Ser Ser Gly Gly Asp Leu Glu Ile Thr
        355                 360                 365

Thr His Ser Phe Asn Cys Arg Gly Glu Phe Phe Tyr Cys Asn Thr Ser
    370                 375                 380

Lys Leu Phe Asn Ser Ser Tyr Asn Gly Thr Ser Tyr Arg Gly Thr Glu
385                 390                 395                 400

Ser Asn Ser Ser Ile Ile Thr Leu Pro Cys Arg Ile Lys Gln Ile Ile
                405                 410                 415

Asp Met Trp Gln Lys Val Gly Arg Ala Ile Tyr Ala Pro Pro Ile Glu
            420                 425                 430

Gly Asn Ile Thr Cys Ser Ser Ser Ile Thr Gly Leu Leu Leu Ala Arg
        435                 440                 445

Asp Gly Gly Leu Asp Asn Ile Thr Thr Glu Ile Phe Arg Pro Gln Gly
    450                 455                 460

Gly Asp Met Lys Asp Asn Trp Arg Asn Glu Leu Tyr Lys Tyr Lys Val
465                 470                 475                 480

Val Glu Ile Lys Pro Leu Gly Val Ala Pro Thr Glu Ala Lys Arg Arg
                485                 490                 495

Val Val Glu Arg Glu Lys Arg Ala Val Gly Ile Gly Ala Val Ile Phe
            500                 505                 510

Gly Phe Leu Gly Ala Ala Gly Ser Asn Met Gly Ala Ala Ser Ile Thr
        515                 520                 525

Leu Thr Ala Gln Ala Arg Gln Leu Leu Ser Gly Ile Val Gln Gln Gln
    530                 535                 540

Ser Asn Leu Leu Arg Ala Ile Glu Ala Gln Gln His Met Leu Gln Leu
545                 550                 555                 560

Thr Val Trp Gly Ile Lys Gln Leu Gln Ala Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
        595                 600                 605

Lys Thr Gln Gly Glu Ile Trp Glu Asn Met Thr Trp Met Gln Trp Asp
    610                 615                 620

Lys Glu Ile Ser Asn Tyr Thr Gly Ile Ile Tyr Arg Leu Leu Glu Glu
625                 630                 635                 640

Ser Gln Asn Gln Gln Glu Gln Asn Glu Lys Asp Leu Leu Ala Leu Asp
                645                 650                 655

Ser Arg Asn Asn Leu Trp Ser Trp Phe Asn Ile Ser Asn Trp Leu Trp
            660                 665                 670

Tyr Ile Lys Ile Phe Ile Met Ile Val Gly Gly Leu Ile Gly Leu Arg
        675                 680                 685

Ile Ile Phe Ala Val Leu Ser Ile Val Asn Arg Val Arg Gln Gly Tyr
    690                 695                 700

Ser Pro Leu Ser Phe Gln Thr Leu Thr Pro Asn Pro Arg Gly Leu Asp
705                 710                 715                 720
```

```
Arg Leu Gly Arg Ile Glu Glu Glu Gly Gly Glu Gln Asp Arg Asp Arg
                725                 730                 735

Ser Ile Arg Leu Val Gln Gly Phe Leu Ala Leu Ala Trp Asp Asp Leu
            740                 745                 750

Arg Ser Leu Cys Leu Phe Ser Tyr His Arg Leu Arg Asp Leu Ile Leu
        755                 760                 765

Val Thr Ala Arg Val Val Glu Leu Leu Gly Arg Ser Ser Pro Arg Gly
    770                 775                 780

Leu Gln Arg Gly Trp Glu Ala Leu Lys Tyr Leu Gly Ser Leu Val Gln
785                 790                 795                 800

Tyr Trp Gly Leu Glu Leu Lys Lys Ser Ala Thr Ser Leu Leu Asp Ser
                805                 810                 815

Ile Ala Ile Ala Val Ala Glu Gly Thr Asp Arg Ile Ile Glu Val Ile
            820                 825                 830

Gln Arg Ile Tyr Arg Ala Phe Cys Asn Ile Pro Arg Arg Val Arg Gln
        835                 840                 845

Gly Phe Glu Ala Ala Leu Gln
    850                 855


<210> SEQ ID NO 25
<211> LENGTH: 20
<212> TYPE: PRT
<213> ORGANISM: Human immunodeficiency virus

<400> SEQUENCE: 25

Asp Ile Lys Gln Gly Pro Lys Glu Pro Phe Arg Asp Tyr Val Asp Arg
 1               5                  10                  15

Phe Phe Lys Thr
            20


<210> SEQ ID NO 26
<211> LENGTH: 60
<212> TYPE: DNA
<213> ORGANISM: Human immunodeficiency virus

<400> SEQUENCE: 26

gacataaaac aaggaccaaa agagcccttt agagactatg tagaccggtt ctttaaaacc     60


<210> SEQ ID NO 27
<211> LENGTH: 20
<212> TYPE: PRT
<213> ORGANISM: Human immunodeficiency virus

<400> SEQUENCE: 27

Asp Ile Arg Gln Gly Pro Lys Glu Pro Phe Arg Asp Tyr Val Asp Arg
 1               5                  10                  15

Phe Phe Lys Thr
            20


<210> SEQ ID NO 28
<211> LENGTH: 47
<212> TYPE: PRT
<213> ORGANISM: Human immunodeficiency virus

<400> SEQUENCE: 28

Thr Ile Thr Ile Thr Cys Arg Ile Lys Gln Ile Ile Asn Met Trp Gln
 1               5                  10                  15

Lys Val Gly Arg Ala Met Tyr Ala Pro Pro Ile Ala Gly Asn Leu Thr
            20                  25                  30

Cys Glu Ser Asn Ile Thr Gly Leu Leu Leu Thr Arg Asp Gly Gly
```

-continued

```
        35                  40                  45


<210> SEQ ID NO 29
<211> LENGTH: 48
<212> TYPE: PRT
<213> ORGANISM: Human immunodeficiency virus

<400> SEQUENCE: 29

Ser Ile Ile Thr Leu Pro Cys Arg Ile Lys Gln Ile Ile Asp Met Trp
 1               5                  10                  15

Gln Lys Val Gly Arg Ala Ile Tyr Ala Pro Pro Ile Glu Gly Asn Ile
            20                  25                  30

Thr Cys Ser Ser Ser Ile Thr Gly Leu Leu Leu Ala Arg Asp Gly Gly
        35                  40                  45


<210> SEQ ID NO 30
<211> LENGTH: 4
<212> TYPE: PRT
<213> ORGANISM: Human immunodeficiency virus

<400> SEQUENCE: 30

Gly Gly Gly Ser
 1
```

POLYNUCLEOTIDES ENCODING ANTIGENIC HIV TYPE C POLYPEPTIDES, POLYPEPTIDES AND USES THEREOF

CROSS-REFERENCE TO RELATED APPLICATIONS

This application is a Continuation of U.S. patent application Ser. No. 12/215,189, (Now U.S. Pat. No. 7,943,375) with a filing date of Jun. 25, 2008, which is a Continuation of U.S. patent application Ser. No. 09/475,704, filed Dec. 30, 1999, which claims priority to U.S. Provisional Patent Applications Nos. 60/114,495, filed Dec. 31, 1998 and 60/152,195, filed Sep. 1, 1999, all of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002118003SEQLISTING.txt, date recorded: May 13, 2011, size: 57 KB).

TECHNICAL FIELD

Polynucleotides encoding antigenic Type C HIV Gag-containing polypeptides and/or Env-containing polypeptides are described, as are uses of these polynucleotides and polypeptide products in immunogenic compositions.

BACKGROUND OF THE INVENTION

Acquired immune deficiency syndrome (AIDS) is recognized as one of the greatest health threats facing modern medicine. There is, as yet, no cure for this disease. In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225:840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2 See, e.g., Guyader et al. (1987) Nature 326:662-669; Brun-Vezinet et al. (1986) Science 233: 343-346; Clavel et al. (1986) Nature 324:691-695.

A great deal of information has been gathered about the HIV virus, however, to date an effective vaccine has not been identified. Several targets for vaccine development have been examined including the env and Gag gene products encoded by HIV. Gag gene products include, but are not limited to, Gag-polymerase and Gag-protease. Env gene products include, but are not limited to, monomeric gp120 polypeptides, oligomeric gp140 polypeptides and gp160 polypeptides.

Haas, et al., (*Current Biology* 6(3):315-324, 1996) suggested that selective codon usage by HIV-1 appeared to account for a substantial fraction of the inefficiency of viral protein synthesis. Andre, et al., (*J. Virol.* 72(2):1497-1503, 1998) described an increased immune response elicited by DNA vaccination employing a synthetic gp120 sequence with optimized codon usage. Schneider, et al., (*J. Virol.* 71(7): 4892-4903, 1997) discuss inactivation of inhibitory (or instability) elements (INS) located within the coding sequences of the Gag and Gag-protease coding sequences.

The Gag proteins of HIV-1 are necessary for the assembly of virus-like particles. HIV-1 Gag proteins are involved in many stages of the life cycle of the virus including, assembly, virion maturation after particle release, and early post-entry steps in virus replication. The roles, of HIV-1 Gag proteins are numerous and complex (Freed, E. O., *Virology* 251:1-15, 1998).

Wolf, et al., (PCT International Application, WO 96/30523, published 3 Oct. 1996; European Patent Application, Publication No. 0 449 116 A1, published 2 Oct. 1991) have described the use of altered pr55 Gag of HIV-1 to act as a non-infectious retroviral-like particulate carrier, in particular, for the presentation of immunologically important epitopes. Wang, et al., (*Virology* 200:524-534, 1994) describe a system to study assembly of HIV Gag-β-galactosidase fusion proteins into virions. They describe the construction of sequences encoding HIV Gag-β-galactosidase fusion proteins, the expression of such sequences in the presence of HIV Gag proteins, and assembly of these proteins into virus particles:

Shiver, et al., (PCT International Application, WO 98/34640, published 13 Aug. 1998) described altering HIV-1 (CAM1) Gag coding sequences to produce synthetic DNA molecules encoding HIV Gag and modifications of HIV Gag. The codons of the synthetic molecules were codons preferred by a projected host cell.

Recently, use of HIV Env polypeptides in immunogenic compositions has been described. (see, U.S. Pat. No. 5,846,546 to Hurwitz et al., issued Dec. 8, 1998, describing immunogenic compositions comprising a mixture of at least four different recombinant virus that each express a different HIV env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HIV-1 isolate containing the sequence GPGR. There remains a need for antigenic HIV polypeptides, particularly Type C isolates.

SUMMARY OF THE INVENTION

The present invention relates to improved expression of HIV Type C Gag-containing polypeptides and production of virus-like particles, as well as, Env-containing polypeptides.

One aspect of the present invention relates to expression cassettes and polynucleotides contained therein. In one embodiment, an expression cassette comprises a polynucleotide sequence encoding a polypeptide including an HIV Gag-containing polypeptide, wherein the polynucleotide sequence encoding the Gag polypeptide comprises a sequence having at least about 85%, preferably about 90%, more preferably about 95%, and most preferably about 98% sequence identity to the sequences taught in the present specification. The polynucleotide sequences encoding Gag-containing polypeptides include, but are not limited to, the following polynucleotides: nucleotides 844-903 of FIG. 1 (a Gag major homology region) (SEQ ID NO:1); nucleotides 841-900 of FIG. 2 (a Gag major homology region) (SEQ ID NO:2); the sequence presented as FIG. 1 (SEQ ID NO:3); and the sequence presented as FIG. 2 (SEQ ID NO:4). The polynucleotides encoding the Gag-containing polypeptides of the present invention may also include sequences encoding additional polypeptides. Such additional polynucleotides encoding polypeptides may include, for example, coding sequences for other HIV proteins, such as, polynucleotide sequences encoding an HIV protease polypeptide, and polynucleotide sequences encoding an HIV polymerase polypeptide. In one embodiment, the sequence encoding the HIV polymerase polypeptide can be modified by deletions of coding regions corresponding to reverse transcriptase and integrase. Such deletions in the polymerase polypeptide can also be made such that the polynucleotide sequence preserves T-helper cell and CTL epitopes. Other antigens of interest may be inserted into the polymerase as well.

In another embodiment, an expression cassette comprises a polynucleotide sequence encoding a polypeptide including an HIV Env-containing polypeptide, wherein the polynucleotide sequence encoding the Env polypeptide comprises a sequence having at least about 85%, preferably about 90%, more preferably about 95%, and most preferably about 98% sequence identity to the sequences taught in the present specification. The polynucleotide sequences encoding Env-containing polypeptides include, but are not limited to, the following polynucleotides: nucleotides 1213-1353 of FIG. 3 (SEQ ID NO:5) (an Env common region); nucleotides 82-1512 of FIG. 3 (SEQ ID NO:6) (a gp120 polypeptide); nucleotides 82-2025 of FIG. 3 (SEQ ID NO:7) (a gp140 polypeptide); nucleotides 82-2547 of FIG. 3 (SEQ ID NO:8) (a gp160 polypeptide); nucleotides 1-2547 of FIG. 3 (SEQ ID NO:9) (a gp160 polypeptide with signal sequence); nucleotides 1513-2547 of FIG. 3 (SEQ ID NO:10) (a gp41 polypeptide); nucleotides 1210-1353 of FIG. 4 (SEQ ID NO:11) (an Env common region); nucleotides 73-1509 of FIG. 4 (SEQ ID NO:12) (a gp120 polypeptide); nucleotides 73-2022 of FIG. 4 (SEQ ID NO:13) (a gp140 polypeptide); nucleotides 73-2565 of FIG. 4 (SEQ ID NO:14) (a gp160 polypeptide); nucleotides 1-2565 of FIG. 4 (SEQ ID NO:15) (a gp160 polypeptide with signal sequence); and nucleotides 1510-2565 of FIG. 4 (SEQ ID NO:16) (a gp41 polypeptide).

The present invention further includes recombinant expression systems for use in selected host cells, wherein the recombinant expression systems employ one or more of the polynucleotides and expression cassettes of the present invention. In such systems, the polynucleotide sequences are operably linked to control elements compatible with expression in the selected host cell. Numerous expression control elements are known to those in the art, including, but not limited to, the following: transcription promoters, transcription enhancer elements, transcription termination signals, polyadenylation sequences, sequences for optimization of initiation of translation, and translation termination sequences. Exemplary transcription promoters include, but are not limited to those derived from CMV, CMV+intron A, SV40, RSV, HIV-Ltr, MMLV-ltr, and metallothionein.

In another aspect the invention includes cells comprising the expression cassettes of the present invention where the polynucleotide sequence (e.g., encoding an Env- and/or Gag-containing polypeptide) is operably linked to control elements compatible with expression in the selected cell. In one embodiment such cells are mammalian cells. Exemplary mammalian cells include, but are not limited to, BHK, VERO, HT1080, 293, RD, COS-7, and CHO cells. Other cells, cell types, tissue types, etc., that may be useful in the practice of the present invention include, but are not limited to, those obtained from the following: insects (e.g., *Trichoplusia ni* (Tn5) and Sf9), bacteria, yeast, plants, antigen presenting cells (e.g., macrophage, monocytes, dendritic cells, B-cells, T-cells, stem cells, and progenitor cells thereof), primary cells, immortalized cells, tumor-derived cells.

In a further aspect, the present invention includes compositions for generating an immunological response, where the composition typically comprises at least one of the expression cassettes of the present invention and may, for example, contain combinations of expression cassettes (such as one or more expression cassettes carrying a Gag-polypeptide-encoding polynucleotide and one or more expression cassettes carrying an Env-polypeptide-encoding polynucleotide). Such compositions may further contain an adjuvant or adjuvants. The compositions may also contain one or more Gag-containing polypeptides and/or one or more Env-containing polypeptides. The Gag-containing polypeptides and/or Env-containing polypeptides may correspond to the polypeptides encoded by the expression cassette(s) in the composition, or, the Gag-containing polypeptides and/or Env-containing polypeptides may be different from those encoded by the expression cassettes. An example of the polynucleotide in the expression cassette encoding the same polypeptide as is being provided in the composition is as follows: the polynucleotide in the expression cassette encodes the Gag-polypeptide of FIG. 1 (SEQ ID NO:3), and the polypeptide is the polypeptide encoded by the sequence shown in FIG. 1 (SEQ ID NO:17). An example of the polynucleotide in the expression cassette encoding a different polypeptide as is being provided in the composition is as follows: an expression cassette having a polynucleotide encoding a Gag-polymerase polypeptide, and the polypeptide provided in the composition may be a Gag and/or Gag-protease polypeptide. In compositions containing both expression cassettes (or polynucleotides of the present invention) and polypeptides, the Env and Gag expression cassettes of the present invention can be mixed and/or matched with Env-containing and Gag-containing polypeptides described herein.

In another aspect the present invention includes methods of immunization of a subject. In the method any of the above described compositions are into the subject under conditions that are compatible with expression of the expression cassette in the subject. In one embodiment, the expression cassettes (or polynucleotides of the present invention) can be introduced using a gene delivery vector. The gene delivery vector can, for example, be a non-viral vector or a viral vector. Exemplary viral vectors include, but are not limited to Sindbis-virus derived vectors, retroviral vectors, and lentiviral vectors. Compositions useful for generating an immunological response can also be delivered using a particulate carrier. Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

In a further aspect, the invention includes methods of generating an immune response in a subject, wherein the expression cassettes or polynucleotides of the present invention are expressed in a suitable cell to provide for the expression of the Env- and/or Gag-containing polypeptides encoded by the polynucleotides of the present invention. The polypeptide(s) are then isolated (e.g., substantially purified) and administered to the subject in an amount sufficient to elicit an immune response.

The invention further includes methods of generating an immune response in a subject, where cells of a subject are transfected with any of the above-described expression cassettes or polynucleotides of the present invention, under conditions that permit the expression of a selected polynucleotide and production of a polypeptide of interest (e.g., encoded by any expression cassette of the present invention). By this method an immunological response to the polypeptide is elicited in the subject. Transfection of the cells may be performed ex vivo and the transfected cells are reintroduced into the subject. Alternately, or in addition, the cells may be transfected in vivo in the subject. The immune response may be humoral and/or cell-mediated (cellular). In a further embodiment, this method may also include administration of an Env- and/or Gag-containing polypeptide before, concurrently with, and/or after introduction of the expression cassette into the subject.

Further embodiments of the present invention include purified polynucleotides. Exemplary polynucleotide sequences encoding Gag-containing polypeptides include, but are not limited to, the following polynucleotides: nucleotides 844-903 of FIG. 1 (SEQ ID NO:1) (a Gag major homology region); nucleotides 841-900 of FIG. 2 (SEQ ID NO:2) (a Gag major homology region); the sequence presented as FIG. 1 (SEQ ID NO:3); and the sequence presented as FIG. 2 (SEQ ID NO:4). Exemplary polynucleotide sequences encoding Env-containing polypeptides include, but are not limited to, the following polynucleotides: nucleotides 1213-1353 of FIG. 3 (SEQ ID NO:5) (an Env common region); nucleotides 82-1512 of FIG. 3 (SEQ ID NO:6) (a gp120 polypeptide); nucleotides 82-2025 of FIG. 3 (SEQ ID NO:7) (a gp140 polypeptide); nucleotides 82-2547 of FIG. 3 (SEQ ID NO:8) (a gp160 polypeptide); nucleotides 1-2547 of FIG. 3 (SEQ ID NO:9) (a gp160 polypeptide with signal sequence); nucleotides 1513-2547 of FIG. 3 (SEQ ID NO:10) (a gp41 polypeptide); nucleotides 1210-1353 of FIG. 4 (SEQ ID NO:11) (an Env common region); nucleotides 73-1509 of FIG. 4 (SEQ ID NO:12) (a gp120 polypeptide); nucleotides 73-2022 of FIG. 4 (SEQ ID NO:13) (a gp140 polypeptide); nucleotides 73-2565 of FIG. 4 (SEQ ID NO:14) (a gp160 polypeptide); nucleotides 1-2565 of FIG. 4 (SEQ ID NO:15) (a gp160 polypeptide with signal sequence); and nucleotides 1510-2565 of FIG. 4 (SEQ ID NO:16) (a gp41 polypeptide). The polynucleotide sequence encoding the Gag-containing and Env-containing polypeptides of the present invention typically have at least about 85%, preferably about 90%, more preferably about 95%, and most preferably about 98% sequence identity to the sequences taught herein.

The polynucleotides of the present invention can be produced by recombinant techniques, synthetic techniques, or combinations thereof.

These and other embodiments of the present invention will readily occur to those of ordinary skill in the art in view of the disclosure herein.

BRIEF DESCRIPTION OF THE FIGURES

FIG. 1 (SEQ ID NO:3) shows the nucleotide sequence of a polynucleotide encoding a synthetic Gag polypeptide. The nucleotide sequence shown was obtained by modifying type C strain AF110965 and include further modifications of INS.

FIG. 2 (SEQ ID NO: 4) shows the nucleotide sequence of a polynucleotide encoding a synthetic Gag polypeptide. The nucleotide sequence shown was obtained by modifying type C strain AF110967 and include further modifications of INS.

FIG. 3 (SEQ ID NO:9) shows the nucleotide sequence of a polynucleotide encoding a synthetic Env polypeptide. The nucleotide sequence depicts gp160 (including a signal peptide) and was obtained by modifying type C strain AF110968. The arrows indicate the positions of various regions of the polynucleotide, including the sequence encoding a signal peptide (nucleotides 1-81) (SEQ ID NO:18), a gp120 polypeptide (nucleotides 82-1512) (SEQ ID NO:6), a gp41 polypeptide (nucleotides 1513-2547) (SEQ ID NO:10), a gp140 polypeptide (nucleotides 82-2025) (SEQ ID NO:7) and a gp160 polypeptide (nucleotides 82-2547) (SEQ ID NO:8). The codons encoding the signal peptide are modified (as described herein) from the native HIV-1 signal sequence.

FIG. 4 (SEQ ID NO:15) shows the nucleotide sequence of a polynucleotide encoding a synthetic Env polypeptide. The nucleotide sequence depicts gp160 (including a signal peptide) and was obtained by modifying type C strain AF110975. The arrows indicate the positions of various regions of the polynucleotide, including the sequence encoding a signal peptide (nucleotides 1-72) (SEQ ID NO:19), a gp120 polypeptide (nucleotides 73-1509) (SEQ ID NO:12), a gp41 polypeptide (nucleotides 1510-2565) (SEQ ID NO:16), a gp140 polypeptide (nucleotides 73-2022) (SEQ ID NO:13), and a gp160 polypeptide (nucleotides 73-2565) (SEQ ID NO:14). The codons encoding the signal peptide are modified (as described herein) from the native HIV-1 signal sequence.

FIG. 5 shows the location of some remaining INS in synthetic Gag sequences derived from AF110965. The changes made to these sequences are boxed in the Figures. The top line depicts a codon optimized sequence of Gag polypeptides from the indicated strains (SEQ ID NO:20). The nucleotide(s) appearing below the line in the boxed region(s) depicts changes made to remove further INS and correspond to the sequence depicted in FIG. 1 (SEQ ID NO:3).

FIG. 6 shows the location of some remaining INS in synthetic Gag sequences derived from AF110968. The changes made to these sequences are boxed in the Figures. The top line depicts a codon optimized sequence of Gag polypeptides from the indicated strains (SEQ ID NO:21). The nucleotide(s) appearing below the line in the boxed region(s) depicts changes made to remove further INS and correspond to the sequence depicted in FIG. 2 (SEQ ID NO:4).

DETAILED DESCRIPTION OF THE INVENTION

The practice of the present invention will employ, unless otherwise indicated, conventional methods of chemistry, biochemistry; molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology,* 4th ed. (Ausubel et al. eds., 1999, John Wiley & Sons); *Molecular Biology Techniques: An Intensive Laboratory Course*, (Ream et al., eds., 1998, Academic Press); *PCR* (*Introduction to Biotechniques Series*), 2nd ed. (Newton & Graham eds., 1997, Springer Verlag).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. DEFINITIONS

In describing the present invention, the following terms will be employed, and are intended to be defined as indicated below.

"Synthetic" sequences, as used herein, refers to Gag-encoding polynucleotides whose expression has been optimized as described herein, for example, by codon substitution and inactivation of inhibitory sequences. "Wild-type" or "native" sequences, as used herein, refers to polypeptide encoding sequences that are essentially as they are found in nature, e.g., Gag and/or Env encoding sequences as found in Type C isolates, e.g., AF110965, AF110967, AF110968 or AF110975.

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, X-ray crystallography, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at; or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% sequence (including all integer values falling within these described ranges) identity to the synthetic expression cassette sequences disclosed herein (for example, to the claimed sequences or other sequences of the present invention) when the sequences of the present invention are used as the query sequence.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279-287. Examples of suicide genes are thymidine kinase of herpes simplex virus (HSV-tk), cytochrome P450 (Manome et al. (1996) *Gene Therapy* 3:513-520), human deoxycytidine kinase (Manome et al. (1996) *Nature Medicine* 2(5):567-573) and the bacterial enzyme cytosine deaminase (Dong et al. (1996) *Human Gene Therapy* 7:713-720). Cells which express these genes are rendered sensitive to the effects of the relatively nontoxic prodrugs ganciclovir (HSV-tk), cyclophosphamide (cytochrome P450 2B1), cytosine arabinoside (human dedxycytidine kinase) or 5-fluorocytosine (bacterial cytosine deaminase). Culver et al. (1992) *Science* 256:1550-1552, Huber et al. (1994) *Proc. Natl. Acad. Sci. USA* 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (I) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

"Lentiviral vector", and "recombinant lentiviral vector" refer to a nucleic acid construct which carries, and within certain embodiments, is capable of directing the expression of a nucleic acid molecule of interest. The lentiviral vector include at least, one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the retrovirus used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof.

"Lentiviral vector particle" as utilized within the present invention refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

"Packaging cell" refers to a cell which contains those elements necessary for production of infectious recombinant retrovirus which are lacking in a recombinant retroviral vector. Typically, such packaging cells contain one or more expression cassettes which are capable of expressing proteins which encode Gag, pol and env proteins.

"Producer cell" or "vector producing cell" refers to a cell which contains all elements necessary for production of recombinant retroviral vector particles.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1 Synthetic Expression Cassettes

2.1.1 Modification of HIV-1-Type C Gag and Env Nucleic Acid Coding Sequences One aspect of the present invention is the generation of HIV-1 type C Gag and Env protein coding sequences, and related sequences, having improved expression relative to the corresponding wild-type sequences.

2.1.1.1. Modification of Gag Nucleic Acid Coding Sequences

An exemplary embodiment of the present invention is illustrated herein by modifying the Gag protein wild-type sequences obtained from the AF110965 and AF110967 strains of HIV-1, subtype C. (see, for example, Korber et al. (1998) *Human Retroviruses and Aids*, Los Alamos, N. Mex.: Los Alamos National Laboratory; Novitsky et al. (1999) *J. Virol.* 73(5):4427-4432, for molecular cloning of various subtype C clones from Botswana). Gag sequence obtained from other Type C HIV-1 variants may be manipulated in similar fashion following the teachings of the present specification. Such other variants include, but are not limited to, Gag protein encoding sequences obtained from the isolates of HIV-1 Type C, for example as described in Novitsky et al., (1999), supra; Myers et al., infra; Virology, 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa. and on the World Wide Web (Internet).

First, the HIV-1 codon usage pattern was modified so that the resulting nucleic acid coding sequence was comparable to codon usage found in highly expressed human genes (Example 1). The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The Gag coding sequences were modified to be comparable to codon usage found in highly expressed human genes.

Second, there are inhibitory (or instability) elements (INS) located within the coding sequences of the Gag coding sequences. The RRE is a secondary RNA structure that interacts with the HIV encoded Rev-protein to overcome the expression down-regulating effects of the INS. To overcome the post-transcriptional activating mechanisms of RRE and Rev, the instability elements can be inactivated by introducing multiple point mutations that do not alter the reading frame of the encoded proteins. Subtype C Gag-encoding sequences having inactivated RRE sites are shown in FIGS. 1 (SEQ ID NO:3), 2 (SEQ ID NO:4), 5 (SEQ ID NO:20) and 6 (SEQ ID NO:26).

Modification of the Gag polypeptide coding sequences results in improved expression relative to the wild-type coding sequences in a number of mammalian cell lines (as well as other types of cell lines, including, but not limited to, insect cells). Further, expression of the sequences results in production of virus-like particles (VLPs) by these cell lines (see below).

2.1.1.2 Modification of Env Nucleic Acid Coding Sequences

Similarly, the present invention also includes modified Env proteins. Wild-type Env sequences are obtained from the AF110968 and AF110975 strains of HIV-1, type C. (see, for example, Novitsky et al. (1999) *J. Virol.* 73(5):4427-4432, for molecular cloning of various subtype C clones from Botswana). Env sequence obtained from other Type C HIV-1 variants may be manipulated in similar fashion following the teachings of the present specification. Such other variants include, but are not limited to, Env protein encoding sequences obtained from the isolates of HIV-1 Type C, described above.

The codon usage pattern for Env was modified as described above for Gag so that the resulting nucleic acid coding sequence was comparable to codon usage found in highly expressed human genes. Experiments can be performed in support of the present invention to show that the synthetic Env sequences were capable of higher level of protein production relative to the native Env sequences.

Modification of the Env polypeptide coding sequences results in improved expression relative to the wild-type coding sequences in a number of mammalian cell lines (as well as other types of cell lines, including, but not limited to, insect cells). Similar Env polypeptide coding sequences can be obtained, optimized and tested for improved expression from a variety of isolates, including those described above for Gag.

2.1.2 Further Modification of Sequences Including HIV-1 Gag Nucleic Acid Coding Sequences Experiments can be performed to show that similar modifications of HIV-1 Gag-protease and Gag-polymerase sequences also result in improved expression of the polyproteins, as well as, the production of VLPs formed by polypeptides produced from such modified coding sequences.

For the Gag-protease sequence, the changes in codon usage are typically restricted to the regions up to the −1 frameshift and starting again at the end of the Gag reading frame; however, regions within the frameshift translation region can be modified as well. Further, inhibitory (or instability) elements (INS) located within the coding sequences of the Gag-protease polypeptide coding sequence can be altered as well.

For the Gag-polymerase sequence, the changes in codon usage can be similar to those for the Gag-protease sequence.

In addition to polyproteins containing HIV-related sequences, the Gag encoding sequences of the present invention can be fused to other polypeptides (creating chimeric polypeptides) for which an immunogenic response is desired.

Further sequences useful in the practice of the present invention include, but are not limited to, sequences encoding further viral epitopes/antigens {including but not limited to, HCV antigens (e.g., E1, E2; Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference), HIV antigens (e.g., derived from tat, rev, nef and/or env); and sequences encoding tumor antigens/epitopes. Additional sequences are described below. Also, variations on the orientation of the Gag and other coding sequences, relative to each other, are described below.

Gag, Gag-protease, and/or Gag-polymerase polypeptide coding sequences can be obtained from Type C HIV isolates, see, e.g., Myers et al. Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory. Synthetic expression cassettes can be generated using such coding sequences as starting material by following the teachings of the present specification (e.g., see Example 1).

Further, the synthetic expression cassettes of the present invention include related Gag polypeptide coding sequences having greater than 85%, preferably greater than 90%, more preferably greater than 95%, and most preferably greater than 98% sequence identity to the synthetic expression cassette sequences disclosed herein (for example, FIGS. 1, 2, 5 and 6 (SEQ ID NOs:3, 4, 20 and 21).

The present invention also includes related Env polypeptide coding sequences having greater than 85%, preferably greater than 90%, more preferably greater than 95%, and most preferably greater than 98% sequence identity to the sequences disclosed herein (for example, FIGS. 3 and 4, SEQ ID NOs:5-17). Various coding regions are indicated in FIGS. 3 and 4, for example in FIG. 3 (AF110968), nucleotides 1-81 (SEQ ID NO:18) encode a signal peptide, nucleotides 82-1512 (SEQ ID NO:6) encode a gp120 polypeptide, nucleotides 1513 to 2547 (SEQ ID NO:10) encode a gp41 polypeptide, nucleotides 82-2025 (SEQ ID NO:7) encode a gp140 polypeptide and nucleotides 82-2547 (SEQ ID NO:8) encode a gp160 polypeptide.

2.1.3 Expression of Synthetic Sequences Encoding HIV-1 Gag or Env and Related Polypeptides Synthetic Gag- and Env-encoding sequences (expression cassettes) of the present invention can be cloned into a number of different expression vectors to evaluate levels of expression and, in the case of Gag, production of VLPs. The synthetic DNA fragments for Env and Gag can be cloned into eucaryotic expression vectors, including, a transient expression vector, CMV-promoter-based mammalian vectors, and a shuttle vector for use in baculovirus expression systems. Corresponding wild-type sequences can also be cloned into the same vectors.

These vectors can then be transfected into a several different cell types, including a variety of mammalian cell lines, (293, RD, COS-7, and CHO, cell lines available, for example, from the A.T.C.C.). The cell lines are then cultured under appropriate conditions and the levels of p24 (Gag) or, gp160 or gp120 (Env) expression in supernatants can be evaluated (Example 2). Env polypeptides include, but are not limited to, for example, native gp160, oligomeric gp140, monomeric gp120 as well as modified sequences of these polypeptides. The results of these assays demonstrate that expression of synthetic Env, Gag and Gag-protease encoding sequences are significantly higher than corresponding wild-type sequences.

Further, Western Blot analysis can be used to show that cells containing the synthetic Gag or Env expression cassette produce the expected protein at higher per-cell concentrations than cells containing the native expression cassette. The Gag and Env proteins can be seen in both cell lysates and supernatants. The levels of production are significantly higher in cell supernatants for cells transfected with the synthetic expression cassettes of the present invention.

Fractionation of the supernatants from mammalian cells transfected with the synthetic Gag or Env expression cassette can be used to show that the cassettes provide superior production of both Gag and Env proteins and, in the case of Gag, VLPs, relative to the wild-type sequences.

Efficient expression of these Gag- and/or Env-containing polypeptides in mammalian cell lines provides the following benefits: the polypeptides are free of baculovirus contaminants; production by established methods approved by the FDA; increased purity; greater yields (relative to native coding sequences); and a novel method of producing the Gag- and/or Env-containing polypeptides in CHO cells which is not feasible in the absence of the increased expression obtained using the constructs of the present invention. Exemplary Mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, and CEMX174, such cell lines are available, for example, from the A.T.C.C.).

A synthetic Gag expression cassette of the present invention will also exhibit high levels of expression and VLP production when transfected into insect cells. Synthetic Env expression cassettes also demonstrate high levels of expression in insect cells. Further, in addition to a higher total protein yield, the final product from the synthetic polypeptides consistently contains lower amounts of contaminating baculovirus proteins than the final product from the native Gag or Env.

Further, synthetic Gag and Env expression cassettes of the present invention can also be introduced into yeast vectors which, in turn, can be transformed into and efficiently expressed by yeast cells (*Saccharomyces cerevisea*; using vectors as described in Rosenberg, S, and Tekamp-Olson, P., U.S. Pat. No. RE35,749, issued, Mar. 17, 1998, herein incorporated by reference).

In addition to the mammalian and insect vectors, the synthetic expression cassettes of the present invention can be incorporated into a variety of expression vectors using selected expression control elements. Appropriate vectors and control elements for any given cell type can be selected by one having ordinary skill in the art in view of the teachings of the present specification and information known in the art about expression vectors.

For example, a synthetic Gag or Env expression cassette can be inserted into a vector which includes control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-Ltr, the mouse mammary tumor virus LTR promoter (MMLV-ltr), the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res.* (1991) 19:3979-3986).

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence (Chapman et al., *Nuc. Acids Res.* (1991) 19:3979-3986).

The desired synthetic Gag or Env polypeptide encoding sequences can be cloned into any number of commercially available vectors to generate expression of the polypeptide in an appropriate host system. These systems include, but are not limited to, the following: baculovirus expression {Reilly, P. R., et al., *Baculovirus Expression Vectors: A Laboratory Manual* (1992); Beames, et al., *Biotechniques* 11:378 (1991); Pharmingen; Clontech, Palo Alto, Calif.)}, vaccinia expression {Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., Current Protocols In Molecular Biology, John Wiley and Sons, Inc., Media Pa.; Clontech}, expression in yeast {Rosenberg, S, and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., *Yeast* 8(6):423-488 (1992); Goeddel, D. V., *Methods in Enzymology* 185 (1990); Guthrie, C., and G. R. Fink, *Methods in Enzymology* 194 (1991)}, expression in mammalian cells {Clontech; Gibco-BRL, Ground Island, N.Y.; e.g., Chinese hamster ovary (CHO) cell lines (Haynes, J., et al., *Nuc. Acid. Res.* 11:687-706 (1983); 1983, Lau, Y. F., et al., *Mol. Cell. Biol.* 4:1469-1475 (1984); Kaufman, R. J., "Selection and coamplification of heterologous genes in mammalian cells," in *Methods in Enzymology*, vol. 185, pp 537-566. Academic Press, Inc., San Diego Calif. (1991)}, and expression in plant cells {plant cloning vectors, Clontech Laboratories, Inc., Palo Alto, Calif., and Pharmacia LKB Biotechnology, Inc., Pistcataway, N.J.; Hood, E., et al., *J. Bacteriol.* 168:1291-1301 (1986); Nagel, R., et al., *FEMS Microbiol. Lett.* 67:325 (1990); An, et al., "Binary Vectors", and others in *Plant Molecular Biology Manual A*3:1-19 (1988); Miki, B. L. A., et al., pp. 249-265, and others in *Plant DNA Infectious Agents* (Hohn, T., et al., eds.) Springer-Verlag, Wien, Austria, (1987); *Plant Molecular Biology: Essential Techniques*, P. G. Jones and J. M. Sutton, New York, J. Wiley, 1997; Miglani, Gurbachan *Dictionary of Plant Genetics and Molecular Biology*, New York, Food Products Press, 1998; Henry, R. J., *Practical Applications of Plant Molecular Biology*, New York, Chapman & Hall, 1997}.

Also included in the invention is an expression vector, containing coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., *Mamm. Genome* 7(8):563-574, 1996; Kozak, M., *Biochimie* 76(9):815-821, 1994; Kozak, M., *J Cell Biol* 108(2):229-241, 1989; Kozak, M., and Shatkin, A. J., *Methods Enzymol* 60:360-375, 1979).

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic Gag- and/or Env-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffiriity chromatography can be employed using antibodies generated based on, for example, Gag or Env antigens.

Advantages of expressing the Gag- and/or Env-containing proteins of the present invention using mammalian cells include, but are not limited to, the following: well-established protocols for scale-up production; the ability to produce VLPs; cell lines are suitable to meet good manufacturing process (GMP) standards; culture conditions for mammalian cells are known in the art.

Various forms of the different embodiments of the invention, described herein, may be combined.

2.2 Production of Virus-Like Particles and Use of the Constructs of the Present Invention to Create Packaging Cell Lines The group-specific antigens (Gag) of human immunodeficiency virus type-1 (HIV-1) self-assemble into noninfectious virus-like particles (VLP) that are released from various eucaryotic cells by budding (reviewed by Freed, E. O., *Virology* 251:1-15, 1998). The synthetic expression cassettes of the present invention provide efficient means for the production of HIV-Gag virus-like particles (VLPs) using a variety of different cell types, including, but not limited to, mammalian cells.

Viral particles can be used as a matrix for the proper presentation of an antigen entrapped or associated therewith to the immune system of the host.

2.2.1 VLP Production Using the Synthetic Expression Cassettes of the Present Invention Experiments can be performed in support of the present invention to demonstrate that the synthetic expression cassettes of the present invention provide superior production of both Gag proteins and VLPs, relative to native Gag coding sequences. Further, electron microscopic evaluation of VLP production can show that free and budding immature virus particles of the expected size are produced by cells containing the synthetic expression cassettes.

Using the synthetic expression cassettes of the present invention, rather than native Gag coding sequences, for the production of virus-like particles provide several advantages. First, VLPs can be produced in enhanced quantity making isolation and purification of the VLPs easier. Second, VLPs can be produced in a variety of cell types using the synthetic expression cassettes, in particular, mammalian cell lines can be used for VLP production, for example, CHO cells. Production using CHO cells provides (i) VLP formation; (ii) correct myristylation and budding; (iii) absence of non-mamallian cell contaminants (e.g., insect viruses and/or cells); and (iv) ease of purification. The synthetic expression cassettes of the present invention are also useful for enhanced expression in cell-types other than mammalian cell lines. For example, infection of insect cells with baculovirus vectors encoding the synthetic expression cassettes results in higher levels of total Gag protein yield and higher levels of VLP production (relative to wild-type coding sequences). Further, the final product from insect cells infected with the baculovirus-Gag synthetic expression cassettes consistently contains lower amounts of contaminating insect proteins than the final product when wild-type coding sequences are used.

VLPs can spontaneously form when the particle-forming polypeptide of interest is recombinantly expressed in an appropriate host cell. Thus, the VLPs produced using the synthetic expression cassettes of the present invention are conveniently prepared using recombinant techniques. As discussed below, the Gag polypeptide encoding synthetic expression cassettes of the present invention can include other polypeptide coding sequences of interest (for example, HIV protease, HIV polymerase, HCV core; Env; synthetic Env; see, Example 1). Expression of such synthetic expression cassettes yields VLPs comprising the Gag polypeptide, as well as, the polypeptide of interest.

Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is a matter of choice. See, generally, Sambrook et al, supra. The vector is then used to transform an appropriate host cell. Suitable recombinant expression systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis; insect and yeast systems.

For example, a number of mammalian cell lines are known in the art and include immortalized cell lines available from the American Type Culture Collection (A.T.C.C.), such as, but not limited to, Chinese hamster ovary (CHO) cells, HeLa cells, baby hamster kidney (BHK) cells, monkey kidney cells (COS), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. See, e.g., Summers and Smith, *Texas Agricultural Experiment Station Bulletin No.* 1555 (1987).

Viral vectors can be used for the production of particles in eucaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, *J. Mol. Biol.* (1986) 189:113-130). The method provides for high level, transient, cytoplasmic production of large quantities of RNA and its translation product(s).

Depending on the expression system and host selected, the VLPS are produced by growing host cells transformed by an expression vector under conditions whereby the particle-forming polypeptide is expressed and VLPs can be formed. The selection of the appropriate growth conditions is within the skill of the art. If the VLPs are formed intracellularly, the cells are then disrupted, using chemical, physical or mechanical means, which lyse the cells yet keep the VLPs substantially intact. Such methods are known to those of skill in the art and are described in, e.g., *Protein Purification Applications: A Practical Approach*, (E. L. V. Harris and S. Angal, Eds., 1990).

The particles are then isolated (or substantially purified) using methods that preserve the integrity thereof, such as, by gradient centrifugation, e.g., cesium chloride (CsCl) sucrose gradients, pelleting and the like (see, e.g., Kirnbauer et al. *J. Virol*. (1993) 67:6929-6936), as well as standard purification techniques including, e.g., ion exchange and gel filtration chromatography.

VLPs produced by cells containing the synthetic expression cassettes of the present invention can be used to elicit an immune response when administered to a subject. One advantage of the present invention is that VLPs can be produced by mammalian cells carrying the synthetic expression cassettes at levels previously not possible. As discussed above, the VLPs can comprise a variety of antigens in addition to the Gag polypeptide (e.g., Gag-protease, Gag-polymerase, Env, synthetic Env, etc.). Purified VLPs, produced using the synthetic expression cassettes of the present invention, can be administered to a vertebrate subject, usually in the form of vaccine compositions. Combination vaccines may also be used, where such vaccines contain, for example, an adjuvant subunit protein (e.g., Env). Administration can take place using the VLPs formulated alone or formulated with other antigens. Further, the VLPs can be administered prior to, concurrent with, or subsequent to, delivery of the synthetic expression cassettes for DNA immunization (see below) and/or delivery of other vaccines. Also, the site of VLP administration may be the same or different as other vaccine compositions that are being administered. Gene delivery can be accomplished by a number of methods including, but are not limited to, immunization with DNA, alphavirus vectors, pox virus vectors, and vaccinia virus vectors.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 μg to about 1000 μg, more preferably about 1 μg to about 300 μg, of VLP/antigen.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res*. (1993) 10:362-368; McGee J P, et al., *J Microencapsul*. 14(2):197-210, 1997; O'Hagan D T, et al., *Vaccine* 11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli*.

Adjuvants may also be used to enhance the effectiveness of the compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) oligonucleotides or polymeric molecules encoding immunostimulatory CpG mofifs (Davis, H. L., et al., *J. Immunology* 160:870-876, 1998; Sato, Y. et al., *Science* 273:352-354, 1996) or complexes of antigens/oligonucleotides {Polymeric molecules include double and single stranded RNA and DNA, and backbone modifications thereof, for example, methylphosphonate linkages; or (7) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (8) other substances that act as immunostimulating agents to enhance the effectiveness of the composition. Further, such polymeric molecules include alternative polymer backbone structures such as, but not limited to, polyvinyl backbones (Pitha, *Biochem Biophys Acta,* 204:39, 1970a; Pitha, *Biopolymers,* 9:965, 1970b), and morpholino backbones (Summerton, J., et al., U.S. Pat. No. 5,142,047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).}; and (7) other substances that act as immunostimulating agents to enhance the effectiveness of the VLP immune-stimulating (or vaccine) composition. Alum, CpG oligonucleotides, and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(P-2'-dipalmitoyl-sn-glycero-3-huydroxyphosphoryloxy)-ethylamine (MTP-PE), etc.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner.

If prevention of disease is desired, the antigen carrying VLPs are generally administered prior to primary infection with the pathogen of interest. If treatment is desired, e.g., the reduction of symptoms or recurrences, the VLP compositions are generally administered subsequent to primary infection.

2.2.2 Using the Synthetic Expression Cassettes of the Present Invention to Create Packaging Cell Lines A number of viral based systems have been developed for use as gene transfer vectors for mammalian host cells. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo. A number of retroviral systems have been described, including, for example, the following: (U.S. Pat. No. 5,219,740; Miller et al. (1989) *BioTechniques* 7:980; Miller, A. D. (1990) *Human Gene Therapy* 1:5; Scarpa et al. (1991) *Virology* 180:849; Burns et al. (1993) *Proc. Natl. Acad. Sci. USA* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. No. 5,219,740; U.S. Pat. No. 4,405,712; U.S. Pat. No. 4,861,719; U.S. Pat. No. 4,980,289 and U.S. Pat. No. 4,777,127; in U.S. Ser. No. 07/800,921; and in Vile'(1993) *Cancer Res* 53:3860-3864; Vile (1993) *Cancer Res* 53:962-967; Ram (1993) *Cancer Res* 53:83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci USA* 81; 6349; and Miller (1990) *Human Gene Therapy* 1.

In other embodiments, gene transfer vectors can be constructed to encode a cytokine or other immunomodulatory molecule. For example, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879,227, respectively. In particular aspects of the invention, retroviral vectors expressing cytokine or immunomodulatory genes can be produced as described herein (for example, employing the packaging cell lines of the present invention) and in International Application No. PCT US 94/02951, entitled "Compositions and Methods for Cancer Immunotherapy."

Examples of suitable immunomodulatory molecules for use herein include the following: IL-1 and IL-2 (Karupiah et al. (1990) *J. Immunology* 144:290-298, Weber et al. (1987) *J. Exp. Med.* 166:1716-1733, Gansbacher et al. (1990) *J. Exp. Med.* 172:1217-1224, and U.S. Pat. No. 4,738,927); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (*Cytokine Bulletin*, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-394, Twu et al. (1989) *Proc. Natl. Acad. Sci. USA* 86:2046-2050, and Faktor et al. (1990) *Oncogene* 5:867-872); beta-interferon (Seif et al. (1991) *J. Virol.* 65:664-671); gamma-interferons (Radford et al. (1991) *The American Society of Hepatology* 20082015, Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188).

Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids containing cytokine genes or immunomodulatory genes (International Publication Nos. WO 94/02951 and WO 96/21015, both of which are incorporated by reference in their entirety) can be digested with appropriate restriction enzymes, and DNA fragments containing the particular gene of interest can be inserted into a gene transfer vector using standard molecular biology techniques. (See, e.g., Sambrook et al., supra., or Ausbel et al. (eds) *Current Protocols in Molecular Biology*, Greene Publishing and Wiley-Interscience).

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlidh (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The synthetic expression cassettes of the present invention can be employed in the construction of packaging cell lines for use with retroviral vectors.

One type of retrovirus, the murine leukemia virus, or "MLV", has been widely utilized for gene therapy applications (see generally Mann et al. (*Cell* 33:153, 1993), Cane and Mulligan (*Proc, Nat'l. Acad. Sci. USA* 81:6349, 1984), and Miller et al., *Human Gene 2lerapy* 1:5-14, 1990.

Lentiviral vectors typically, comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). Within certain embodiments, the nuclear transport element is not RRE. Within one embodiment the packaging signal is an extended packaging signal. Within other embodiments the promoter is a tissue specific promoter, or, alternatively, a promoter such as CMV. Within other embodiments, the lentiviral vector further comprises an internal ribosome entry site.

A wide variety of lentiviruses may be utilized within the context of the present invention; including for example, lentiviruses selected from the group consisting of HIV, HIV-1, HIV-2, FIV and SIV.

In one embodiment of the present invention synthetic Gag-polymerase expression cassettes are provided comprising a promoter and a sequence encoding synthetic Gag-polymerase and at least one of vpr, vpu, nef or vif, wherein the promoter is operably linked to Gag-polymerase and vpr, vpu, nef or vif.

Within yet another aspect of the invention, host cells (e.g., packaging cell lines) are provided which contain any of the expression cassettes described herein. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Packaging cell lines may further comprise a promoter and a sequence encoding tat, rev, or an envelope, wherein the promoter is operably linked to the sequence encoding tat, rev, Env or modified Env proteins. The packaging cell line may further comprise a sequence encoding any one or more of nef, vif, vpu or vpr.

In one embodiment, the expression cassette (carrying, for example, the synthetic Gag-polymerase) is stably integrated. The packaging cell line, upon introduction of a lentiviral vector, typically produces particles. The promoter regulating expression of the synthetic expression cassette may be inducible. Typically, the packaging cell line, upon introduction of a lentiviral vector, produces particles that are essentially free of replication competent virus.

Packaging cell lines are provided comprising an expression cassette which directs the expression of a synthetic Gag-polymerase gene or comprising an expression cassette which directs the expression of a synthetic Env genes described herein. (See, also, Andre, S., et al., *Journal of Virology* 72(2): 1497-1503, 1998; Haas, J., et al., *Current Biology* 6(3):315-324, 1996) for a description of other modified Env sequences). A lentiviral vector is introduced into the packaging cell line to produce a vector producing cell line.

As noted above, lentiviral vectors can be designed to carry or express a selected gene(s) or sequences of interest. Lentiviral vectors may be readily constructed from a wide variety of lentiviruses (see RNA Tumor Viruses, Second Edition, Cold Spring Harbor Laboratory, 1985). Representative examples of lentiviruses included HIV, HIV-1, HIV-2, FIV and SIV. Such lentiviruses may either be obtained from patient isolates, or, more preferably, from depositories or collections such as the American Type Culture Collection, or isolated from known sources using available techniques.

Portions of the lentiviral gene delivery vectors (or vehicles) may be derived from different viruses. For example, in a given recombinant lentiviral vector, LTRs may be derived from an HIV, a packaging signal from SW, and an origin of second strand synthesis from HrV-2. Lentiviral vector constructs may comprise a 5' lentiviral LTR, a tRNA binding site, a packaging signal, one or more heterologous sequences, an origin of second strand DNA synthesis and a 3' LTR, wherein said lentiviral vector contains a nuclear transport element that is not RRE.

Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5'LTR. Similarly, the origin of second strand DNA synthesis is, as its name implies, important for the second strand DNA synthesis of a retrovirus. This region, which is also referred to as the poly-purine tract, is located just upstream of the 3'LTR.

In addition to a 5' and 3' LTR, tRNA binding site, and origin of second strand DNA synthesis, recombinant retroviral vector constructs may also comprise a packaging signal, as well as one or more genes or coding sequences of interest. In addition, the lentiviral vectors have a nuclear transport element which, in preferred embodiments is not RRE. Representative examples of suitable nuclear transport elements include the element in Rous sarcoma virus (Ogert, et al., *J. Virol.* 70, 3834-3843, 1996), the element in Rous sarcoma virus (Liu & Mertz, *Genes & Dev.,* 9, 1766-1789, 1995) and the element in the genome of simian retrovirus type I (Zolotukhin, et al., *J. Virol.* 68, 7944-7952, 1994). Other potential elements include the elements in the histone gene (Kedes, *Annu. Rev. Biochem.* 48, 837-870, 1970), the α-interferon gene (Nagata et al., *Nature* 287, 401-408, 1980), the β-adrenergic receptor gene (Koilka, et al., *Nature* 329, 75-79, 1987), and the c-Jun gene (Hattorie, et al., *Proc. Natl. Acad. Sci. USA* 85, 9148-9152, 1988).

Recombinant lentiviral vector constructs typically lack both Gag-polymerase and Env coding sequences. Recombinant lentiviral vector typically contain less than 20, preferably 15, more preferably 10, and most preferably 8 consecutive nucleotides found in Gag-polymerase and Env genes. One advantage of the present invention is that the synthetic Gag-polymerase expression cassettes, which can be used to construct packaging cell lines for the recombinant retroviral vector constructs, have little homology to wild-type Gag-polymerase sequences and thus considerably reduce or eliminate the possibility of homologous recombination between the synthetic and wild-type sequences.

Lentiviral vectors may also include tissue-specific promoters to drive expression of one or more genes or sequences of interest.

Lentiviral vector constructs may be generated such that more than one gene of interest is expressed. This may be accomplished through the use of di- or oligo-cistronic cassettes (e.g., where the coding regions are separated by 80 nucleotides or less, see generally Levin et al., *Gene* 108:167-174, 1991), or through the use of Internal Ribosome Entry Sites ("IRES").

Packaging cell lines suitable for use with the above described recombinant retroviral vector constructs may be readily prepared given the disclosure provided herein. Briefly, the parent cell line from which the packaging cell line is derived can be selected from a variety of mammalian cell lines, including for example, 293, RD, COS-7, CHO, BHK, VERO, HT1080, and myeloma cells.

After selection of a suitable host cell for the generation of a packaging cell line, one or more expression cassettes are introduced into the cell line in order to complement or supply in trans components of the vector which have been deleted.

Representative examples of suitable expression cassettes have been described herein and include synthetic Env, synthetic Gag, synthetic Gag-protease, and synthetic Gag-polymerase expression cassettes, which comprise a promoter and a sequence encoding, e.g., Gag-polymerase and at least one of vpr, vpu, nef or vif, wherein the promoter is operably linked to Gag-polymerase and vpr, vpu, nef or vif. As described above, the native and/or modified Env coding sequences may also be utilized in these expression cassettes.

Utilizing the above-described expression cassettes, a wide variety of packaging cell lines can be generated. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Within other aspects, packaging cell lines are provided comprising a promoter and a sequence encoding tat, rev, Env, or other HIV antigens or epitopes derived therefrom, wherein the promoter is operably linked to the sequence encoding tat, rev, Env, or the HIV antigen or epitope. Within further embodiments, the packaging cell line may comprise a sequence encoding any one or more of nef, vif, vpu or vpr. For example, the packaging cell line may contain only nef, vif, vpu, or vpr alone, nef and vif, nef and vpu, nef and vpr, vif and vpu, vif and vpr, vpu and vpr, nef vif and vpu, nef vif and vpr, nef vpu and vpr, vvir vpu and vpr, or, all four of nef vif vpu and vpr.

In one embodiment, the expression cassette is stably integrated. Within another embodiment, the packaging cell line, upon introduction of a lentiviral vector, produces particles. Within further embodiments the promoter is inducible. Within certain preferred embodiments of the invention, the packaging cell line, upon introduction of a lentiviral vector, produces particles that are free of replication competent virus.

The synthetic cassettes containing optimized coding sequences are transfected into a selected cell line. Transfected cells are selected that (i) carry, typically, integrated, stable copies of the Gag, Pol, and Env coding sequences, and (ii) are expressing acceptable levels of these polypeptides (expression can be evaluated by methods known in the prior art, e.g., see Examples 1-4). The ability of the cell line to produce VLPs may also be verified.

A sequence of interest is constructed into a suitable viral vector as discussed above. This defective virus is then transfected into the packaging cell line. The packaging cell line provides the viral functions necessary for producing virus-like particles into which the defective viral genome, containing the sequence of interest, are packaged. These VLPs are then isolated and can be used, for example, in gene delivery or gene therapy.

Further, such packaging cell lines can also be used to produce VLPs alone, which can, for example, be used as adjuvants for administration with other antigens or in vaccine compositions. Also, co-expression of a selected sequence of interest encoding a polypeptide (for example, an antigen) in the packaging cell line can also result in the entrapment and/or association of the selected polypeptide in/with the VLPs.

2.3 DNA Immunization and Gene Delivery

A variety of HIV polypeptide antigens, particularly Type C HIV antigens, can be used in the practice of the present invention. HIV antigens can be included in DNA immunization constructs containing, for example, a synthetic Gag expression cassette fused in-frame to a coding sequence for the polypeptide antigen, where expression of the construct results in VLPs presenting the antigen of interest.

HIV antigens of particular interest to be used in the practice of the present invention include tat, rev, nef, vif, vpu, vpr, and other HIV antigens or epitopes derived therefrom. For example, the packaging cell line may contain only nef, and HIV-1 (also known as HTLV-III, LAV, ARV, etc.), including, but not limited to, antigens such as gp120, gp41, gp160 (both native and modified); Gag; and pol from a variety of isolates including, but not limited to, $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 strains from diverse subtypes (e.g., subtypes, A through G, and O), HIV-2 strains and diverse subtypes (e.g., HIV-$2_{UC1}$ and HIV-$2_{UC2}$). See, e.g., Myers, et al., Los Alamos Database, Los Alamos National Laboratory, Los Alamos, N. Mex.; Myers, et al., *Human Retroviruses and Aids,* 1990, Los Alamos, N. Mex.: Los Alamos National Laboratory.

To evaluate efficacy, DNA immunization using synthetic expression cassettes of the present invention can be performed, for instance as described in Example 4. Mice are immunized with both the Gag (and/or Env) synthetic expression cassette and the Gag (and/or Env) wild type expression cassette. Mouse immunizations with plasmid-DNAs will show that the synthetic expression cassettes provide a clear improvement of immunogenicity relative to the native expression cassettes. Also, the second boost immunization will induce a secondary immune response, for example, after approximately two weeks. Further, the results of CTL assays will show increased potency of synthetic Gag (and/or Env) expression cassettes for induction of cytotoxic T-lymphocyte (CTL) responses by DNA immunization.

It is readily apparent that the subject invention can be used to mount an immune response to a wide variety of antigens and hence to treat or prevent a HIV infection, particularly Type C HIV infection.

2.3.1 Delivery of the Synthetic Expression Cassettes of the Present Invention

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311; Stemmer, W. P. C., (1995) *Gene* 164:49-53.

Next, the gene sequence encoding the desired antigen can be inserted into a vector containing a synthetic Gag or synthetic Env expression cassette of the present invention. The antigen is inserted into the synthetic Gag coding sequence such that when the combined sequence is expressed it results in the production of VLPs comprising the Gag polypeptide and the antigen of interest, e.g., Env (native or modified) or other antigen derived from HIV. Insertions can be made within the coding sequence or at either end of the coding sequence (5', amino terminus of the expressed Gag polypeptide; or 3', carboxy terminus of the expressed Gag polypeptide)(Wagner, R., et al., *Arch Virol.* 127:117-137, 1992; Wagner, R., et al., *Virology* 200:162-175, 1994; Wu, X., et al., *J. Virol.* 69(6):3389-3398, 1995; Wang, C-T., et al., *Virology* 200:524-534, 1994; Chazal, N., et al., *Virology* 68(1):111-122, 1994; Griffiths, J. C., et al., *J. Virol.* 67(6):3191-3198, 1993; Reicin, A. S., et al., *J. Virol.* 69(2):642-650, 1995).

Up to 50% of the coding sequences of p55Gag can be deleted without affecting the assembly to virus-like particles and expression efficiency (Borsetti, A., et al, *J. Virol.* 72(11):9313-9317, 1998; Garnier, L., et al., *J Virol* 72(6):4667-4677, 1998; Zhang, Y., et al., *J Virol* 72(3):1782-1789, 1998; Wang, C., et al., *J Virol* 72(10): 7950-7959, 1998). In one embodiment of the present invention, immunogenicity of the high level expressing synthetic Gag expression cassettes can be increased by the insertion of different structural or non-structural HIV antigens, multiepitope cassettes, or cytokine sequences into deleted regions of Gag sequence. Such deletions may be generated following the teachings of the present invention and information available to one of ordinary skill in the art. One possible advantage of this approach, relative to using full-length sequences fused to heterologous polypeptides, can be higher expression/secretion efficiency of the expression product.

When sequences are added to the amino terminal end of Gag, the polynucletide can contain coding sequences at the 5' end that encode a signal for addition of a myristic moiety to the Gag-containing polypeptide (e.g., sequences that encode Met-Gly).

The ability of Gag-containing polypeptide constructs to form VLPs can be empirically determined following the teachings of the present specification.

Gag/antigen (e.g., Gag/Env) synthetic expression cassettes include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric antigen-coding gene sequences, encoding, e.g., multiple antigens/epitopes of interest, for example derived from more than one viral isolate.

Typically the antigen coding sequences precede or follow the synthetic coding sequence and the chimeric transcription unit will have a single open reading frame encoding both the antigen of interest and the synthetic Gag coding sequences. Alternatively, multi-cistronic cassettes (e.g., bi-cistronic cassettes) can be constructed allowing expression of multiple antigens from a single mRNA using the EMCV IRES, or the like.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic Gag/ or Env/antigen coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting $TK^-$recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Gag-polypeptide encoding expression cassette). For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, *Gene* (1994) 143:245-249; Gao et al., *Biochem. Biophys. Res. Commun.* (1994) 200:1201-1206; Gao and Huang, *Nuc. Acids Res.* (1993) 21:2867-2872; Chen et al., *Nuc. Acids Res.* (1994) 22:2114-2120; and U.S. Pat. No. 5,135,855.

A synthetic Gag- and/or Env-containing expression cassette of interest can also be delivered without a viral vector.

For example, the synthetic expression cassette can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta*. (1991) 1097: 1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Feigner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem*. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun*. (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem*. (1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein antigen(s) can also be delivered in cochleate lipid compositions similar to those described by Papahadjopoulos et al., *Biochem. Biophys. Acta*. (1975) 394: 483-491. See, also, U.S. Pat. Nos. 4,663,161 and 4,871,488.

The synthetic expression cassette of interest may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Intl Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, *Vaccine* 12:1503-1509, 1994; Bioject, Inc., Portland, Oreg.).

Recombinant vectors carrying a synthetic expression cassette of the present invention are formulated into compositions for delivery to the vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

2.3.2 Ex Vivo Delivery of the Synthetic Expression Cassettes of the Present Invention In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, $CD4^+$ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove $CD4^+$ cells), or can be isolated by the use of CD8 antibodies coupled to a solid support. CD4 lymphocytes from HIV-1 infected patients can be expanded ex vivo, before or after transduction as described by Wilson et. al. (1995) *J. Infect. Dis.* 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) *Exp. Hematol.* 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic expression cassette of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6: Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 μg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1\times10^6$ and $5\times10^6$, preferably between about $0.5\times10^6$ and $2\times10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Generation of Synthetic Expression Cassettes

A. Modification of HIV-1 Env, Gag, Gag-protease and Gag-polymerase Nucleic Acid Coding Sequences The Gag, Gag-protease, and Gag-polymerase coding sequences were selected from the Type C strains AF110965 and AF110967. The Env coding sequences were selected from Type C strains AF110968 and AF110975. These sequences were manipulated to maximize expression of their gene products.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The coding sequences were modified to be comparable to codon usage found in highly expressed human genes.

Second, there are inhibitory (or instability) elements (INS) located within the coding sequences of the Gag and Gag-protease coding sequences (Schneider R, et al., *J. Virol.* 71(7): 4892-4903, 1997). RRE is a secondary RNA structure that interacts with the HIV encoded Rev-protein to overcome the expression down-regulating effects of the INS. To overcome the post-transcriptional activating mechanisms of RRE and Rev, the instability elements are inactivated by introducing multiple point mutations that do not alter the reading frame of the encoded proteins. FIGS. 5 and 6 (SEQ ID Nos: 3, 4, 20 and 21) show the location of some remaining INS in synthetic sequences derived from strains AF110965 and AF110967. The changes made to these sequences are boxed in the Figures. In FIGS. 5 and 6, the top line depicts a codon optimized sequence of Gag polypeptides from the indicated strains. The nucleotide(s) appearing below the line in the boxed region(s) depicts changes made to further remove INS. Thus, when the changes indicated in the boxed regions are made, the resulting sequences correspond to the sequences depicted in FIGS. 1 and 2, respectively.

For the Gag-protease sequence, the changes in codon usage are restricted to the regions up to the −1 frameshift and starting again at the end of the Gag reading frame. Further, inhibitory (or instability) elements (INS) located within the coding sequences of the Gag-protease polypeptide coding sequence are altered as well. The synthetic coding sequences are assembled by methods known in the art, for example by companies such as the Midland Certified Reagent Company (Midland, Tex.).

Modification of the Gag-polymerase sequences include similar modifications as described for Gag-protease in order to preserve the frameshift region.

In one embodiment of the invention, the full length polymerase coding region of the Gag-polymerase sequence is included with the synthetic Gag or Env sequences in order to increase the number of epitopes for virus-like particles expressed by the synthetic, optimized Gag/Env expression cassette. Because synthetic HIV-1 Gag-polymerase expresses the functional enzymes reverse transcriptase (RT) and integrase (INT) (in addition to the structural proteins and protease), it is important to inactivate RT and INT functions. Several deletions or mutations in the RT and INT coding regions can be made to achieve catalytic nonfunctional enzymes with respect to their RT and INT activity. {Jay. A. Levy (Editor) (1995) *The Retroviridae*, Plenum Press, New York. ISBN 0-306-45033X. Pages 215-20; Grimison, B. and Laurence, J. (1995), *Journal Of Acquired Immune Deficiency Syndromes and Human Retrovirology* 9(1):58-68; Wakefield, J. K., et al., (1992) *Journal Of Virology* 66(11):6806-6812; Esnouf, R., et al., (1995) *Nature Structural Biology* 2(4):303-308; Maignan, S., et al., (1998) *Journal Of Molecular Biology* 282(2):359-368; Katz, R. A. and Skalka, A. M. (1994) *Annual Review Of Biochemistry* 73 (1994); Jacobo-Molina, A., et al., (1993) *Proceedings Of the National Academy Of Sciences Of the United States Of America* 90(13):6320-6324; Hickman, A. B., et al., (1994) *Journal Of Biological Chemistry* 269(46): 29279-29287; Goldgur, Y., et al., (1998) *Proceedings Of the National Academy Of Sciences Of the United States Of America* 95(16):9150-9154; Goette, M., et al., (1998) *Journal Of Biological Chemistry* 273(17):10139-10146; Gorton, J. L., et al., (1998) *Journal of Virology* 72(6):5046-5055; Engelman, A., et al., (1997) *Journal Of Virology* 71(5):3507-3514; Dyda, F., et al., *Science* 266(5193):1981-1986; Davies, J. F., et al., (1991) *Science* 252(5002):88-95; Bujacz, G., et al., (1996) *Febs Letters* 398(2-3):175-178; Beard, W. A., et al., (1996) *Journal Of Biological Chemistry* 271(21):12213-12220; Kohlstaedt, L. A., et al., (1992) *Science* 256(5065): 1783-1790; Krug, M. S, and Berger, S. L. (1991) *Biochemistry* 30(44):10614-10623; Mazumder, A., et al., (1996) *Molecular Pharmacology* 49(4):621-628; Palaniappan, C., et al., (1997) *Journal Of Biological Chemistry* 272(17):11157-11164; Rodgers, D. W., et al., (1995) *Proceedings Of the National Academy Of Sciences Of the United States Of America* 92(4):1222-1226; Sheng, N. and Dennis, D. (1993) *Biochemistry* 32(18):4938-4942; Spence, R. A., et al., (1995) *Science* 267(5200):988-993.}

Furthermore selected B- and/or T-cell epitopes can be added to the Gag-polymerase constructs within the deletions of the RT- and INT-coding sequence to replace and augment any epitopes deleted by the functional modifications of RT and INT. Alternately, selected B- and T-cell epitopes (including CTL epitopes) from RT and INT can be included in a minimal VLP formed by expression of the synthetic Gag or synthetic GagProt cassette, described above. (For descriptions of known HIV B- and T-cell epitopes see, HIV Molecular Immunology Database CTL Search Interface; Los Alamos Sequence Compendia, 1987-1997 on the Internet.)

The resulting modified coding sequences are presented as a synthetic Env expression cassette; a synthetic Gag expression cassette; a synthetic Gag-protease expression cassette; and a synthetic Gag-polymerase expression cassette. A common Gag region (Gag-common) extends from nucleotide position 844 to position 903 (SEQ ID NO:1), relative to AF110965 (or from approximately amino acid residues 282 to 301 of SEQ ID NO:17) and from nucleotide position 841 to position 900 (SEQ ID NO:2), relative to AF110967 (or from approximately amino acid residues 281 to 300 of SEQ ID NO:22). A common Env region (Env-common) extends from nucleotide position 1213 to position 1353 (SEQ ID NO:5) and amino acid positions 405 to 451 of SEQ ID NO:23, relative to AF110968 and from nucleotide position 1210 to position 1353 (SEQ ID NO:11) and amino acid positions 404-451 (SEQ ID NO:24), relative to AF110975.

The synthetic DNA fragments for Gag and Env are cloned into the following eucaryotic expression vectors: pCMVKm2, for transient expression assays and DNA immunization studies, the pCMVKm2 vector is derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site is inserted into pCMVKm2 to generate pCMV-link; pESN2dhfr and pCMVPLEdhfr, for expression in Chinese Hamster Ovary (CHO) cells; and, pAcC13, a shuttle vector for use in the Baculovirus expression system (pAcC13, is derived from pAcC12 which is described by Munemitsu S., et al., *Mol Cell Biol.* 10(11):5977-5982, 1990).

Briefly, construction of pCMVPLEdhfr was as follows.

To construct a DHFR cassette, the EMCV IRES (internal ribosome entry site) leader was PCR-amplified from pCite-4-a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser (SEQ ID NO:30) spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/Neo$_{(m2)}$. Finally the bovine growth hormone terminator from pcDNA3 (Invitrogen, Inc., Carlsbad, Calif.) was inserted downstream of the neo gene to give pET-E-DHFR/Neo$_{(m2)}$BGHt. The EMCV-dhfr/neo selectable marker cassette fragment was prepared by cleavage of pET-E-DHFR/Neo$_{(m2)}$BGHt.

The CMV enhancer/promoter plus Intron A was transferred from pCMV6a (Chapman et al., *Nuc. Acids Res.* (1991) 19:3979-3986) as a HindIII-Sal1 fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter. The vector also contained an $amp^r$ gene and an SV40 origin of replication.

B. Defining of the Major Homology Region (MHR) of HIV-1 p55Gag

The Major Homology Region (MHR) of HIV-1 p55 (Gag) is located in the p24-CA sequence of Gag. It is a conserved stretch of approximately 20 amino acids. The position in the wild type AF110965 Gag protein is from 282-301 (SEQ ID NO:25) and spans a region from 844-903 (SEQ ID NO:26) for the Gag DNA-sequence. The position in the synthetic Gag protein is also from 282-301 (SEQ ID NO:25) and spans a region from 844-903 (SEQ ID NO:1) for the synthetic Gag DNA-sequence. The position in the wild type and synthetic AF110967 Gag protein is from 281-300 (SEQ ID NO:27) and spans a region from 841-900 (SEQ ID NO:2) for the modified Gag DNA-sequence. Mutations or deletions in the MHR can severely impair particle production (Borsetti, A., et al., *J. Virol.* 72(11):9313-9317, 1998; Mammano, F., et al., *J Virol* 68(8):4927-4936, 1994).

Percent identity to this sequence can be determined, for example, using the Smith-Waterman search algorithm (Time Logic, Incline Village, Nev.), with the following exemplary parameters: weight matrix=nuc4×4hb; gap opening penalty=20, gap extension penalty=5.

C. Defining of the Common Sequence Region of HIV-1 Env

The common sequence region (CSR) of HIV-1 Env is located in the C4 sequence of Env. It is a conserved stretch of approximately 47 amino acids. The position in the wild type and synthetic AF110968 Env protein is from approximately amino acid residue 405 to 451 (SEQ ID NO:28) and spans a region from 1213 to 1353 (SEQ ID NO:5) for the Env DNA-sequence. The position in the wild type and synthetic AF110975 Env protein is from approximately amino acid residue 404 to 451 (SEQ ID NO:29) and spans a region from 1210 to 1353 (SEQ ID NO:11) for the Env DNA-sequence.

Percent identity to this sequence can be determined, for example, using the Smith-Waterman search algorithm (Time Logic, Incline Village, Nev.), with the following exemplary parameters: weight matrix=nuc4×4hb; gap opening penalty=20, gap extension penalty=5.

Various forms of the different embodiments of the invention, described herein, may be combined.

Example 2

Expression Assays for the Synthetic Coding Sequences

A. Env, Gag and Gag-Protease Coding Sequences

The wild-type Env (from AF110968 or AF110975), Gag (from AF110965 and AF110967) and Gag-protease (from AF110965 and AF110967) sequences are cloned into expression vectors having the same features as the vectors into which the synthetic Env, Gag and Gag-protease sequences are cloned.

Expression efficiencies for various vectors carrying the wild-type and synthetic Env and Gag sequences are evaluated as follows. Cells from several mammalian cell lines (293, RD, COS-7, and CHO; all obtained from the American Type Culture Collection, 10801 University Boulevard, Manassas, Va. 20110-2209) are transfected with 2 μg of DNA in transfection reagent LT1 (PanVera Corporation, 545 Science Dr., Madison, Wis.). The cells are incubated for 5 hours in reduced serum medium (Opti-MEM, Gibco-BRL, Gaithersburg, Md.). The medium is then replaced with normal medium as follows: 293 cells, IMDM, 10% fetal calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells are incubated for either 48 or 60 hours. Cell lysates are collected as described below in Example 3. Supernatants are harvested and filtered through 0.45 μm syringe filters. Supernatants are evaluated using the Coulter p24-assay (Coulter Corporation, Hialeah, Fla., US), using 96-well plates coated with a murine monoclonal antibody directed against HIV core antigen. The HIV-1 p24 antigen binds to the coated wells. Biotinylated antibodies against HIV recognize the bound p24 antigen. Conjugated strepavidin-horseradish peroxidase reacts with the biotin. Color develops from the reaction of peroxidase with TMB substrate. The reaction is terminated by addition of 4N $H_2SO_4$. The intensity of the color is directly proportional to the amount of HIV p24 antigen in a sample.

Synthetic Env, Gag and Gag-protease expression cassettes provides dramatic increases in production of their protein products, relative to the native (wild-type Type C) sequences, when expressed in a variety of cell lines.

Example 3

Western Blot Analysis of Expression

A. Env, Gag and Gag-Protease Coding Sequences

Human 293 cells are transfected as described in Example 2 with pCMV6a-based vectors containing native or synthetic Env or Gag expression cassettes. Cells are cultivated for 60 hours post-transfection. Supernatants are prepared as described. Cell lysates are prepared as follows. The cells are washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. SDS-polyacrylamide gels (pre-cast 8-16%; Novex, San Diego, Calif.) are loaded with 20 μl of supernatant or 12.5 μl of cell lysate. A protein standard is also loaded (5 μl, broad size range standard; BioRad Laboratories, Hercules, Calif.). Electrophoresis is carried out and the proteins are transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer is performed at 100 volts for 90 minutes. The membranes are exposed to HIV-1-positive human patient serum and immunostained using o-phenylenediamine dihydrochloride (OPD; Sigma).

Immunoblotting analysis shows that cells containing the synthetic Env or Gag expression cassette produce the expected protein at higher per-cell concentrations than cells containing the native expression cassette. The proteins are seen in both cell lysates and supernatants. The levels of production are significantly higher in cell supernatants for cells transfected with the synthetic expression cassettes of the present invention.

In addition, supernatants from the transfected 293 cells are fractionated on sucrose gradients. Aliquots of the supernatant are transferred to Polyclear™ ultra-centrifuge tubes (Beckman Instruments, Columbia, Md.), under-laid with a solution of 20% (wt/wt) sucrose, and subjected to 2 hours centrifugation at 28,000 rpm in a Beckman SW28 rotor. The resulting pellet is suspended in PBS and layered onto a 20-60% (wt/wt) sucrose gradient and subjected to 2 hours centrifugation at 40,000 rpm in a Beckman SW41ti rotor.

The gradient is then fractionated into approximately 10×1 ml aliquots (starting at the top, 20%-end, of the gradient). Samples are taken from fractions 1-9 and are electrophoresed on 8-16% SDS polyacrylamide gels. The supernatants from 293/synthetic Env or Gag cells give much stronger bands than supernatants from 293/native Env or Gag cells.

Example 4

In Vivo Immunogenicity of Synthetic Gag and Env Expression Cassettes

A. Immunization

To evaluate the possibly improved immunogenicity of the synthetic Gag and Env expression cassettes, a mouse study is performed. The plasmid DNA, pCMVKM2 carrying the synthetic Gag expression cassette, is diluted to the following final concentrations in a total injection volume of 100 μg, 2 μg, 0.2 μg, 0.02 and 0.002 μg. To overcome possible negative dilution effects of the diluted DNA, the total DNA concentration in each sample is brought up to 20 μg using the vector (pCMVKM2) alone. As a control, plasmid DNA of the native Gag expression cassette is handled in the same manner. Twelve groups of four to ten Balb/c mice (Charles River, Boston, Mass.) are intramuscularly immunized (50 μl per leg, intramuscular injection into the tibialis anterior) according to the schedule in Table 1.

TABLE 1

| Group | Gag or Env Expression Cassette | Concentration of Gag or Env plasmid DNA (μg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |
| 11 | Native | 20 | 0, 4 |
| 12 | Native | 2 | 0, 4 |
| 13 | Native | 0.2 | 0, 4 |
| 14 | Native | 0.02 | 0, 4 |
| 15 | Native | 0.002 | 0, 4 |
| 16 | Native | 20 | 0 |
| 17 | Native | 2 | 0 |
| 18 | Native | 0.2 | 0 |
| 19 | Native | 0.02 | |
| 20 | Native | 0.002 | 0 |

[1]= initial immunization at "week 0"

Groups 1-5 and 11-15 are bled at week 0 (before immunization), week 4, week 6, week 8, and week 12. Groups 6-20 and 16-20 are bled at week 0 (before immunization) and at week 4.

B. Humoral Immune Response

The humoral immune response is checked with an anti-HIV Gag or Env antibody ELISAs (enzyme-linked immunosorbent assays) of the mice sera 0 and 4 weeks post immunization (groups 5-12) and, in addition, 6 and 8 weeks post immunization, respectively, 2 and 4 weeks post second immunization (groups 1-4).

The antibody titers of the sera are determined by anti-Gag or anti-Env antibody ELISA. Briefly, sera from immunized mice are screened for antibodies directed against the HIV p55 Gag protein or an Env protein, e.g., gp160 or gp120. ELISA microtiter plates are coated with 0.2 μg of Gag or Env protein per well overnight and washed four times; subsequently, blocking is done with PBS-0.2% Tween (Sigma) for 2 hours. After removal of the blocking solution, 100 μl of diluted mouse serum is added. Sera are tested at 1/25 dilutions and by serial 3-fold dilutions, thereafter. Microtiter plates are washed four times and incubated with a secondary, peroxidase-coupled anti-mouse IgG antibody (Pierce, Rockford, Ill.). ELISA plates are washed and 100 μl of 3, 3', 5, 5'-tetramethyl benzidine (TMB; Pierce) is added per well. The optical density of each well is measured after 15 minutes. The titers reported are the reciprocal of the dilution of serum that gave a half-maximum optical density (O.D.).

Synthetic expression cassettes will provide a clear improvement of immunogenicity relative to the native expression cassettes.

C. Cellular Immune Response

The frequency of specific cytotoxic T-lymphocytes (CTL) is evaluated by a standard chromium release assay of peptide pulsed Balb/c mouse CD4 cells. Gag or Env expressing vaccinia virus infected CD-8 cells are used as a positive control. Briefly, spleen cells (Effector cells, E) are obtained from the BALB/c mice immunized as described above are cultured, restimulated, and assayed for CTL activity against Gag peptide-pulsed target cells as described (Doe, B., and Walker, C. M., *AIDS* 10(7):793-794, 1996). Cytotoxic activity is measured in a standard $^{51}Cr$ release assay. Target (T) cells are cultured with effector (E) cells at various E:T ratios for 4 hours and the average cpm from duplicate wells are used to calculate percent specific $^{51}Cr$ release.

Cytotoxic T-cell (CTL) activity is measured in splenocytes recovered from the mice immunized with HIV Gag or Env DNA. Effector cells from the Gag or Env DNA-immunized animals exhibit specific lysis of Gag or Env peptide-pulsed SV-BALB (MHC matched) targets cells, indicative of a CTL response. Target cells that are peptide-pulsed and derived from an MHC-unmatched mouse strain (MC57) are not lysed.

Thus, synthetic Env and Gag expression cassettes exhibit increased potency for induction of cytotoxic T-lymphocyte (CTL) responses by DNA immunization.

Example 5

DNA-immunization of Non-Human Primates Using a Synthetic Env or Gag Expression Cassette Non-human primates are immunized multiple times (e.g., weeks 0, 4, 8 and 24) intradermally, mucosally or bilaterally, intramuscular, into the quadriceps using various doses (e.g., 1-5 mg) synthetic Gag- and/or Env-containing plasmids. The animals are bled two weeks after each immunization and ELISA is performed with isolated plasma. The ELISA is performed essentially as described in Example 4 except the second antibody-conjugate is an anti-human IgG, g-chain specific, peroxidase conjugate (Sigma Chemical Co., St. Louis, Md. 63178) used at a dilution of 1:500. Fifty μg/ml yeast extract is added to the dilutions of plasma samples and antibody conjugate to reduce non-specific background due to preexisting yeast antibodies in the non-human primates.

Further, lymphoproliferative responses to antigen can also be evaluated post-immunization, indicative of induction of T-helper cell functions.

Both synthetic Env and Gag plasmid DNA is expected to be immunogenic in non-human primates.

Example 6

In Vitro Expression of Recombinant Sindbis RNA and DNA Containing the Synthetic Env and Gag Expression Cassette To evaluate the expression efficiency of the synthetic Env and Gag expression cassette in Alphavirus vectors, the selected synthetic expression cassette is subcloned into both plasmid DNA-based and recombinant vector particle-based Sindbis virus vectors. Specifically, a cDNA vector construct for in vitro transcription of Sindbis virus RNA vector replicons (pRSIN-luc; Dubensky, et al., *J. Virol.* 70:508-519, 1996) is modified to contain a PmeI site for plasmid linearization and a polylinker for insertion of heterologous genes. A polylinker is generated using two oligonucleotides that contain the sites XhoI, PmlI, ApaI, NarI, XbaI, and Nod (XPANXNF, and XPANXNR).

The plasmid pRSIN-luc (Dubensky et al., supra) is digested with XhoI and NotI to remove the luciferase gene insert, blunt-ended using Klenow and dNTPs, and purified from an agarose get using GeneCleanII (Bio101, Vista, Calif.). The oligonucleotides are annealed to each other and ligated into the plasmid. The resulting construct is digested with NotI and Sad to remove the minimal Sindbis 3'-end sequence and $A_{40}$ tract, and ligated with an approximately 0.4 kbp fragment from PKSSIN1-BV (WO 97/38087). This 0.4 kbp fragment is obtained by digestion of pKSSIN1-BV with NotI and SacI, and purification after size fractionation from an agarose gel. The fragment contains the complete Sindbis virus 3'-end, an $A_{40}$ tract and a PmeI site for linearization. This new vector construct is designated SINBVE.

The synthetic HIV Gag and Env coding sequences are obtained from the parental plasmid by digestion with EcoRI, blunt-ending with Klenow and dNTPs, purification with GeneCleanII, digestion with SalI, size fractionation on an agarose gel, and purification from the agarose gel using GeneCleanII. The synthetic Gag or Env coding fragment is ligated into the SINBVE vector that is digested with XhoI and PmtI. The resulting vector is purified using GeneCleanII and is designated SINBVGag. Vector RNA replicons may be transcribed in vitro (Dubensky et al., supra) from SINBVGag and used directly for transfection of cells. Alternatively, the replicons may be packaged into recombinant vector particles by co-transfection with defective helper RNAs or using an alphavirus packaging cell line.

The DNA-based Sindbis virus vector pDCMVSIN-beta-gal (Dubensky, et al., *J. Virol.* 70:508-519, 1996) is digested with SalI and XbaI, to remove the beta-galactosidase gene insert, and purified using GeneCleanII after agarose gel size fractionation. The HIV Gag or Env gene is inserted into the pDCMVSIN-beta-gal by digestion of SINBVGag with SalI and XhoI, purification using GeneCleanII of the Gag-containing fragment after agarose gel size fractionation, and ligation. The resulting construct is designated pDSIN-Gag, and may be used directly for in vivo administration or formulated using any of the methods described herein.

BHK and 293 cells are transfected with recombinant Sindbis RNA and DNA, respectively. The supernatants and cell lysates are tested with the Coulter capture ELISA (Example 2).

BHK cells are transfected by electroporation with recombinant Sindbis RNA.

293 cells are transfected using LT-1 (Example 2) with recombinant Sindbis DNA. Synthetic Gag- and/or Env-containing plasmids are used as positive controls. Supernatants and lysates are collected 48 h post transfection.

Gag and Env proteins can be efficiently expressed from both DNA and RNA-based Sindbis vector systems using the synthetic expression cassettes.

Example 7

In Vivo Immunogenicity of Recombinant Sindbis Replicon Vectors Containing Synthetic Gag and/or Env Expression Cassettes A. Immunization To evaluate the immunogenicity of recombinant synthetic Gag and Env expression cassettes in Sindbis replicons, a mouse study is performed. The Sindbis virus DNA vector carrying the synthetic Gag and/or Env expression cassette (Example 6), is diluted to the following final concentrations in a total injection volume of 100 μg, 20 μg, 0.2 μg, 0.02 and 0.002 μg. To overcome possible negative dilution effects of the diluted DNA, the total DNA concentration in each sample is brought up to 20 μg using the Sindbis replicon vector DNA alone. Twelve groups of four to ten Balb/c mice (Charles River, Boston, Mass.) are intramuscularly immunized (50 μl per leg, intramuscular injection into the tibialis anterior) according to the schedule in Table 2. Alternatively, Sindbis viral particles are prepared at the following doses: $10^3$ pfu, $10^5$ pfu and $10^7$ pfu in 100 μl, as shown in Table 3. Sindbis Env or Gag particle preparations are administered to mice using intramuscular and subcutaneous routes (50 μl per site).

TABLE 2

| Group | Gag or Env Expression Cassette | Concentration of Gag or Env DNA (μg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |

[1]= initial immunization at "week 0"

TABLE 3

| Group | Gag or Env sequence | Concentration of viral particle (pfu) | Immunized at time (weeks): |
|---|---|---|---|
| 1 | Synthetic | $10^3$ | 0[1], 4 |
| 2 | Synthetic | $10^5$ | 0, 4 |
| 3 | Synthetic | $10^7$ | 0, 4 |
| 8 | Synthetic | $10^3$ | 0 |
| 9 | Synthetic | $10^5$ | 0 |
| 10 | Synthetic | $10^7$ | 0 |

[1]= initial immunization at "week 0"

Groups are bled and assessment of both humoral and cellular (e.g., frequency of specific CTLs) is performed, essentially as described in Example 4.

Although preferred embodiments of the subject invention have been described in some detail, it is understood that obvious variations can be made without departing from the spirit and the scope of the invention as defined by the appended claims.

We claim:

1. An expression cassette comprising a polynucleotide sequence operably linked to a promoter, wherein the polynucleotide sequence comprises a nucleotide sequence having at least 90% sequence identity to full-length SEQ ID NO: 6 and encodes an immunogenic HIV Env polypeptide that elicits an Env-specific immune response.

2. An expression cassette comprising a polynucleotide sequence operably linked to a promoter, wherein the polynucleotide sequence comprises a nucleotide sequence having at least 90% sequence identity to full-length SEQ ID NO:12 and encodes an immunogenic HIV Env polypeptide that elicits an Env-specific immune response.

3. The expression cassette of claim 1, wherein the nucleotide sequence encoding said HIV Env polypeptide comprises SEQ ID NO:6.

4. The expression cassette of claim 2, wherein the nucleotide sequence encoding said HIV Env polypeptide consists of SEQ ID NO:12.

5. The expression cassette of claim 1 or claim 2, wherein said polynucleotide sequence further includes a nucleotide sequence encoding an HIV protease polypeptide.

6. The expression cassette of claim 1 or claim 2, wherein said polynucleotide sequence further includes a nucleotide sequence encoding an HIV polymerase polypeptide.

7. The expression cassette of claim 1 or claim 2, wherein said polynucleotide sequence further includes a nucleotide sequence encoding an HIV polymerase polypeptide, wherein the nucleotide sequence encoding the HIV polymerase polypeptide is modified by deletions of coding regions encoding reverse transcriptase and integrase.

8. The expression cassette of claim 7, wherein said polynucleotide sequence encodes a polypeptide comprising an epitope of a T-helper cell or a cytotoxic T cell (CTL).

9. A recombinant expression system for use in a selected host cell, comprising, the expression cassette of claim 1 or claim 2, and wherein said polynucleotide sequence is operably linked to control elements compatible with expression in the selected host cell.

10. The recombinant expression system of claim 9, wherein said control elements are selected from the group consisting of a transcription promoter, a transcription enhancer element, a transcription termination signal, polyadenylation sequences, sequences for optimization of initiation of translation, and translation termination sequences.

11. The recombinant expression system of claim 10, wherein said transcription promoter is selected from the group consisting of CMV, CMV+intron A, SV40, RSV, HW-Ltr, MMLV-ltr, and metallothionein.

12. An isolated cell comprising the expression cassette of claim 1 or claim 2, and wherein said polynucleotide sequence is operably linked to control elements compatible with expression in the selected cell.

13. The isolated cell of claim 12, wherein the isolated cell is a mammalian cell.

14. The isolated cell of claim 13, wherein the isolated cell is selected from the group consisting of BRK, VERO, HT1080, 293, RD, COS-7, and CHO cells.

15. The isolated cell of claim 14, wherein said isolated cell is a CHO cell.

16. The isolated cell of claim 12, wherein the isolated cell is an insect cell.

17. The isolated cell of claim 16, wherein the isolated cell is either Trichoplusia ni (Tn5) or Sf9 insect cells.

18. The isolated cell of claim 12, wherein the isolated cell is a bacterial cell.

19. The isolated cell of claim 12, wherein the isolated cell is a yeast cell.

20. The isolated cell of claim 12, wherein the isolated cell is a plant cell.

21. The isolated cell of claim 12, wherein the isolated cell is an antigen presenting cell.

22. The isolated cell of claim 21, wherein the isolated antigen presenting cell is selected from the group consisting of macrophage, monocytes, dendritic cells, B-cells, T-cells, stem cells, and progenitor cells thereof.

23. The isolated cell of claim 12, wherein the isolated cell is a primary cell.

24. The isolated cell of claim 12, wherein the isolated cell is an immortalized cell.

25. The isolated cell of claim 12, wherein the isolated cell is a tumor-derived cell.

26. A composition for generating an immunological response, comprising: the expression cassette of claim 1 or claim 2 with a pharmaceutically acceptable excipient or vehicle.

27. The composition of claim 26, further comprising an Env polypeptide.

28. The composition of claim 26, further comprising an adjuvant.

29. A method of generating an immune response in a subject, comprising, introducing the composition of claim 26 into said subject such that the expression cassette is expressed in said subject.

30. The method of claim 29, wherein said expression cassette is introduced using a gene delivery vector.

31. The method of claim 30, wherein the gene delivery vector is a non-viral vector.

32. The method of claim 30, wherein said gene delivery vector is a viral vector.

33. The method of claim 32, wherein said gene delivery vector is a Sindbis-virus derived vector.

34. The method of claim 32, wherein said gene delivery vector is a retroviral vector.

35. The method of claim 32, wherein said gene delivery vector is a lentiviral vector.

36. The method of claim 29, wherein said composition is delivered using a particulate carrier.

37. The method of claim 29, wherein said composition is coated on a gold or tungsten particle and said coated particle is delivered to said subject using a gene gun.

38. The method of claim 29, wherein said composition is encapsulated in a liposome preparation.

39. The method of claim 29, wherein said subject is a mammal.

40. The method of claim 29, wherein said mammal is a human.

41. The method of claim 29, where the method further comprises administration of an HIV polypeptide.

42. The method of claim 41, wherein administration of the polypeptide to the subject is carried out before introducing said expression cassette.

43. The method of claim 41, wherein administration of the polypeptide to the subject is carried out concurrently with introducing said expression cassette.

44. The method of claim 41, wherein administration of the polypeptide to the subject is carried out after introducing said expression cassette.

* * * * *